United States Patent
Hirai et al.

(10) Patent No.: US 9,187,063 B2
(45) Date of Patent: Nov. 17, 2015

(54) DETECTION APPARATUS AND METHOD

(75) Inventors: Hideaki Hirai, Kanagawa (JP); Izumi Itoh, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 494 days.

(21) Appl. No.: 13/549,917

(22) Filed: Jul. 16, 2012

(65) Prior Publication Data

US 2013/0027557 A1 Jan. 31, 2013

(30) Foreign Application Priority Data

Jul. 29, 2011 (JP) ................................. 2011-166609

(51) Int. Cl.
 *B60S 1/08* (2006.01)
 *G06K 9/00* (2006.01)
 *G01N 21/21* (2006.01)
 *H04N 7/18* (2006.01)

(52) U.S. Cl.
 CPC ........... *B60S 1/0844* (2013.01); *G06K 9/00791* (2013.01); *G01N 21/21* (2013.01)

(58) Field of Classification Search
 CPC .......... H04N 7/181; B60R 1/00; B60R 11/04; B60R 2300/105; B60R 2300/802; B60S 1/0844; B60Q 1/1423; G06K 9/00791
 See application file for complete search history.

(56) References Cited

U.S. PATENT DOCUMENTS

| | | | |
|---|---|---|---|
| 4,867,561 A | 9/1989 | Fujii et al. | |
| 6,313,454 B1 | 11/2001 | Bos et al. | |
| 6,353,392 B1 | 3/2002 | Schofield et al. | |
| 7,274,012 B2 | 9/2007 | Itoh et al. | |
| 7,492,990 B2 | 2/2009 | Hashiguchi et al. | |
| 7,586,084 B2 | 9/2009 | Itoh et al. | |
| 7,630,132 B2 | 12/2009 | Sangu et al. | |
| 7,697,395 B2 | 4/2010 | Hirai et al. | |
| 7,894,133 B2 | 2/2011 | Hirai et al. | |
| 8,178,010 B2 | 5/2012 | Hirai et al. | |
| 2002/0056805 A1 | 5/2002 | Bos et al. | |
| 2004/0200948 A1 | 10/2004 | Bos et al. | |

(Continued)

FOREIGN PATENT DOCUMENTS

| | | |
|---|---|---|
| EP | 1580092 A2 | 9/2005 |
| EP | 1 777 943 A1 | 4/2007 |

(Continued)

OTHER PUBLICATIONS

European Search Report mailed on Mar. 4, 2015 for European Application No. 12 17 8077.

(Continued)

*Primary Examiner* — Jefferey Harold
*Assistant Examiner* — Sean Haiem
(74) *Attorney, Agent, or Firm* — Harness, Dickey & Pierce

(57) ABSTRACT

A substance detection apparatus and method including a light source to emit light to a planar transparent member having a proximal first face and a distal second face opposite the first face, the light from the light source first striking the first face of the planar transparent member. The substance detection apparatus and method including an image capture lens, a polarization filter, an image sensor, and a substance detection processor. The light emitted from the light source is reflected at the substance present on the second face of the planar transparent member, and the image sensor receives light reflected from the substance, via the image capture lens and the polarization filter, to capture an image of the substance present on the second face of the planar transparent member.

11 Claims, 21 Drawing Sheets

(56) References Cited

U.S. PATENT DOCUMENTS

| | | |
|---|---|---|
| 2005/0195485 A1 | 9/2005 | Hirai et al. |
| 2006/0006317 A1 | 1/2006 | Itoh et al. |
| 2006/0163458 A1 | 7/2006 | Reime |
| 2006/0177098 A1* | 8/2006 | Stam ............................ 382/104 |
| 2007/0090311 A1 | 4/2007 | Pallaro |
| 2007/0127111 A1 | 6/2007 | Hashiguchi et al. |
| 2007/0217011 A1 | 9/2007 | Kiyosawa et al. |
| 2008/0106789 A1 | 5/2008 | Hirai et al. |
| 2009/0315993 A1 | 12/2009 | Hirai |
| 2010/0014073 A1 | 1/2010 | Hashiguchi et al. |
| 2010/0020401 A1 | 1/2010 | Fujimoto et al. |
| 2010/0118366 A1 | 5/2010 | Tokita et al. |
| 2010/0155977 A1 | 6/2010 | Hirai et al. |
| 2010/0208060 A1* | 8/2010 | Kobayashi et al. ........... 348/135 |
| 2011/0255390 A1 | 10/2011 | Hirai |
| 2011/0285898 A1 | 11/2011 | Kasahara et al. |
| 2012/0002280 A1 | 1/2012 | Hirai et al. |
| 2012/0268582 A1* | 10/2012 | Rothenhausler ................ 348/78 |
| 2012/0268602 A1* | 10/2012 | Hirai et al. .................... 348/148 |

FOREIGN PATENT DOCUMENTS

| | | |
|---|---|---|
| JP | 64-25036 | 1/1989 |
| JP | 2001-066246 A | 3/2001 |
| JP | 2005-195566 A | 7/2005 |
| JP | 2005-225250 A | 8/2005 |
| JP | 2005/531752 A | 10/2005 |
| JP | 2010-204059 A | 9/2010 |
| JP | 2010/223685 A | 10/2010 |

OTHER PUBLICATIONS

Japanese Patent Application No. 2011-166609 mailed Mar. 6, 2015.

* cited by examiner

FIG. 14
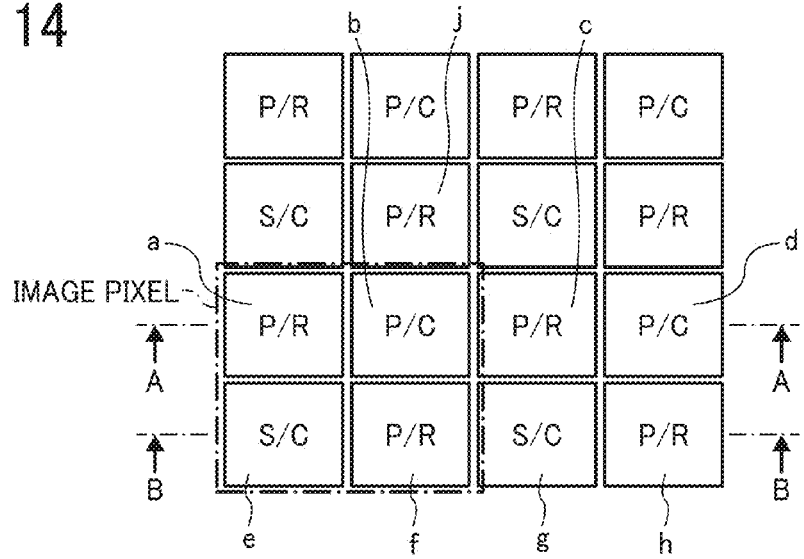
FIG. 15
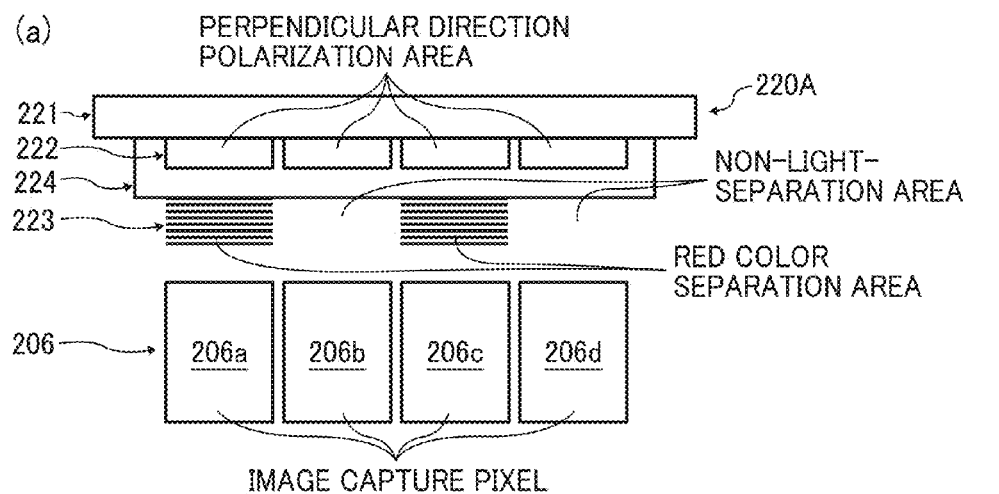
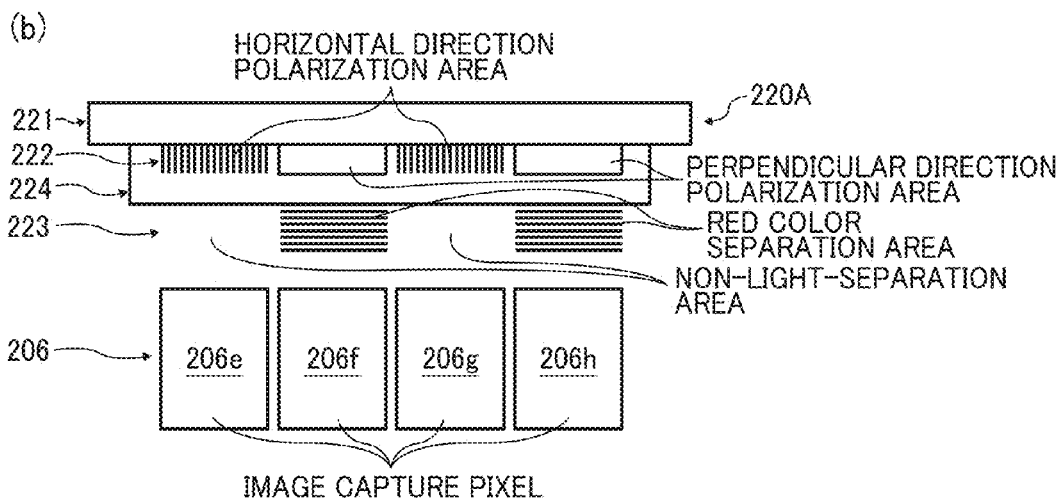

FIG. 16
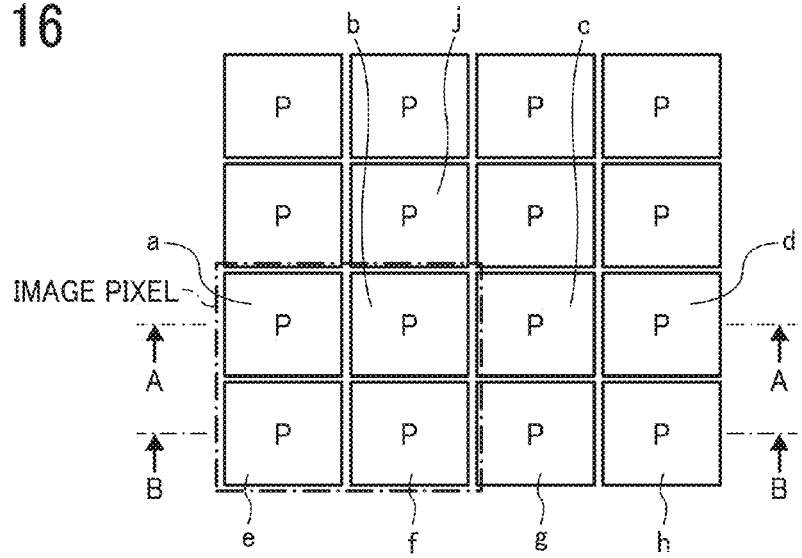
FIG. 17
(a)
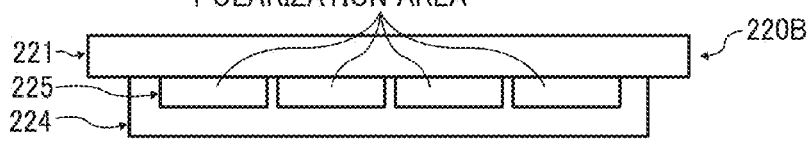
(b)
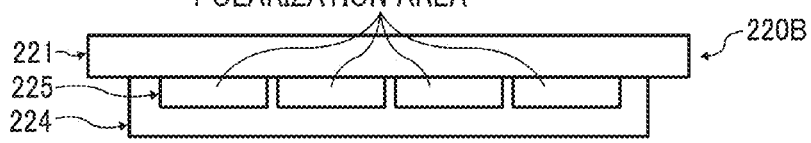
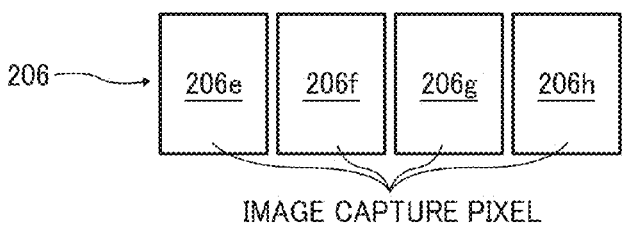

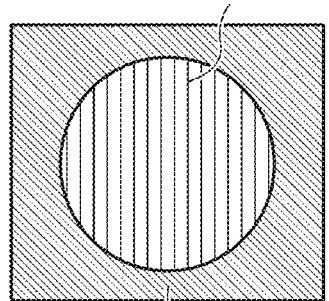

FIG. 24
WIRE GRID STRUCTURE
LIGHT-SHIELD AREA
(SOLID FILM OF ALUMINUM)

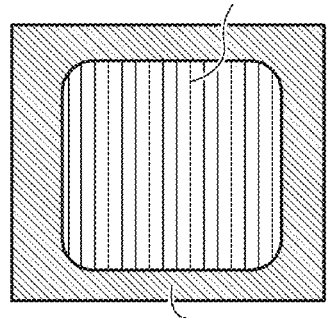

FIG. 25
WIRE GRID STRUCTURE
LIGHT-SHIELD AREA
(SOLID FILM OF ALUMINUM)

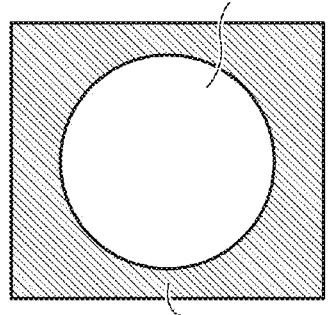

FIG. 26
APERTURE (NO WIRE GRID STRUCTURE)
LIGHT-SHIELD AREA
(SOLID FILM OF ALUMINUM)

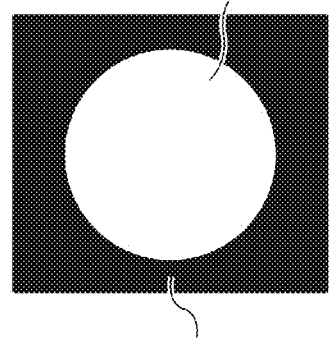

FIG. 27
APERTURE (NO WIRE GRID STRUCTURE)
LIGHT-SHIELD AREA
(SOLID FILM OF ALUMINUM)

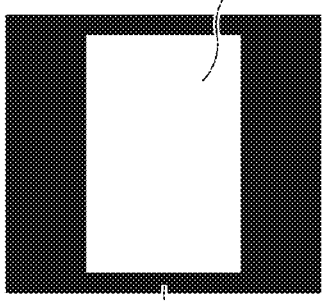

FIG. 28
APERTURE (NO WIRE GRID STRUCTURE)
LIGHT-SHIELD AREA
(SOLID FILM OF ALUMINUM)

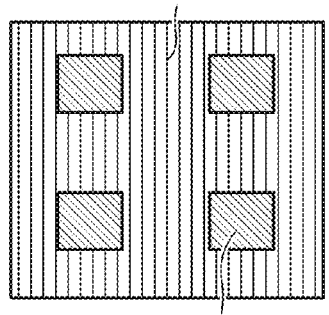

FIG. 29
WIRE GRID STRUCTURE
LIGHT-SHIELD AREA
(SOLID FILM OF ALUMINUM)

(a) WET  (b) DRY

→ HORIZONTAL POLARIZED LIGHT (Is)
--▶ PERPENDICULAR POLARIZED LIGHT (Ip)

(a) (b)

(a)   (b)

FIG. 49
(a)
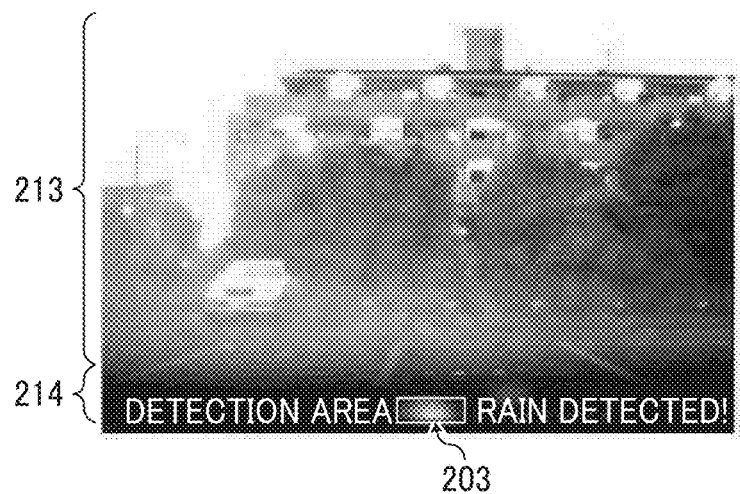
(b)

DETECTION APPARATUS AND METHOD

CROSS-REFERENCE TO RELATED APPLICATION

The present application claims priority to Japanese patent application no. 2011-166609, filed on Jul. 29, 2011, which is incorporated by reference herein in its entirety.

BACKGROUND

1. Technical Field

The present invention relates to a detection apparatus and method, in which images of an adhered substance such as raindrops on a planar transparent member such as a windshield are captured, and detection of adhered substance is conducted based on the captured images.

2. Description of the Background Art

JP-2010-204059-A discloses a raindrop detector that can identify raindrops by capturing P-polarized and S-polarized images using an image capturing device. The S-polarized images and the P-polarized images can be captured as follows: a light source disposed in a raindrop-detector-equipped vehicle emits parallel light to a windshield (i.e., transparent plane) of the detector-equipped vehicle by setting the Brewster's angle as the incidence angle, and the image capturing device receives light reflected from the windshield, by which the S-polarized images and the P-polarized images can be captured. Then, based on a difference of reflection ratio between the captured S-polarized images and the P-polarized images, it is determined whether raindrops are on the windshield.

As noted, the parallel light is emitted to the windshield by setting the Brewster's angle as the incidence angle. Under such setting, if raindrops do not adhere on an outer face of the windshield, which is an opposite face of the windshield by which the parallel light coming from the light source strikes the windshield, only the S-polarized light is reflected at the outer face of the windshield. Therefore, a difference of reflection ratio between the S-polarized images and the P-polarized images captured by the image capturing device becomes great.

In contrast, if raindrops adhere on the outer face of the windshield, the S-polarized light and also the P-polarized light are reflect at the outer face of the windshield. Therefore, a difference of reflection ratio between the S-polarized images and the P-polarized images captured by the image capturing device becomes small. The raindrop detector of JP-2010-204059-A uses takes advantage of this feature to identify an image area having a small reflection ratio as an area with a raindrop.

However, light coming from an object disposed inside the detector-equipped vehicle may regularly be reflected at an inner face of the windshield, which is a face of the windshield from which the parallel light coming from the light source enters, and may be projected on the windshield as a ghost image. Such ghost image may be captured by the image capturing device with images of raindrops on the outer face of the windshield. Such ghost image, generated by regular reflection light, has greater light intensity. Therefore, the ghost image becomes ambient light, which adversely affects the precision of the raindrop detector of JP-2010-204059-A.

Further, when the light source emits light toward the windshield, before the light reaches the outer face of the windshield, the light coming from the light source may regularly be reflected at the inner face of the windshield as regular reflection light having greater light intensity. Such reflection light also becomes ambient light, which adversely affects the precision of the raindrop detector of JP-2010-204059-A.

Such problem may occur when any type of substances including raindrops adhere on a face of the transparent plane, which is an opposite face of the transparent plane that the light coming from the light source enters.

BRIEF SUMMARY OF THE INVENTION

In one aspect of the present invention, a substance detection apparatus is devised. The substance detection apparatus includes a light source to emit light to a planar transparent member, having a proximal first face and a distal second face opposite the first face, the light from the light source first striking the first face of the planar transparent member; an image capture lens; a polarization filter; an image sensor; and a substance detection processor that executes a detection process to detect a substance present on the second face of the planar transparent member based on an image of the substance captured by the image sensor. The polarization filter, disposed after the image capture lens and before the image sensor with respect to a direction of the light entering the image sensor, passes only a polarized light component having a polarized light direction substantially parallel to a virtual plane including an optical axis of the light source that emits the light to the planar transparent member and an optical axis of the image capture lens. The image sensor is composed of a two-dimensional array of pixels having a plurality of light receiving elements. The light emitted from the light source is reflected at the substance present on the second face of the planar transparent member, and the image sensor receives a light reflected from the substance, via the image capture lens and the polarization filter, to capture an image of the substance present on the second face of the planar transparent member.

In another aspect of the present invention, a method of detecting a substance is devised. The method includes the steps of: emitting light, using a light source, to a planar transparent member, having a proximal first face and distal second face opposite the first face, the light from the light source first striking the first face of the planar transparent member; when the light emitted from the light source is reflected at a substance on the second face of the planar transparent member, receiving light reflected from the planar transparent member by an image capture lens; passing, via a polarization filter, only a polarized light component having a polarized light direction substantially parallel to a virtual plane including an optical axis of the light source that emits the light to the planar transparent member and an optical axis of the image capture lens; capturing an image of the substance present on the second face of the planar transparent member by using an image sensor composed of a pixel array having a plurality of light receiving elements arrayed two dimensionally, based on the light reflected from the planar transparent member and passed through the polarization filter; and detecting the substance based on the image of substance captured by the image sensor.

In another aspect of the present invention, a non-transitory computer-readable storage medium storing a program that, when executed by a computer, causes the computer to execute a method of detecting a substance is devised. The method includes the steps of: emitting light, using a light source, to a planar transparent member, having a proximal first face and distal second face opposite the first face, the light from the light source first striking the first face of the planar transparent member; when the light emitted from the light source is reflected at a substance on the second face of the planar transparent member, receiving light reflected from the planar transparent member by an image capture lens; passing, via a polarization filter, only a polarized light component having a polarized light direction substantially parallel to a virtual plane including an optical axis of the light source that emits the light to the planar transparent member and an optical axis of the image capture lens; capturing an image of the substance present on the second face of the planar transparent member by using an image sensor composed of a pixel array having a plurality of light receiving elements arrayed two dimensionally, based on the light reflected from the planar transparent member and passed through the polarization filter; and detecting the substance based on the image of substance captured by the image sensor.

BRIEF DESCRIPTION OF THE DRAWINGS

A more complete appreciation of the disclosure and many of the attendant advantages and features thereof can be readily obtained and understood from the following detailed description with reference to the accompanying drawings, wherein:

FIG. 14 shows an example pixel configuration of the optical filter of a first example configuration, in which light passes a vehicle detection filter of the optical filter, and then received by each photodiode on the image sensor, and information corresponding to the received light or information of each image capture pixel is shown;

FIG. 15(a) shows a schematic cross-sectional view of the vehicle detection filter of the optical filter, and the image sensor cut at a line A-A shown in FIG. 14, and FIG. 15(b) shows a schematic cross-sectional view of the vehicle detection filter of the optical filter, and the image sensor cut at a line B-B shown in FIG. 14;

FIG. 16 shows an example pixel configuration of the optical filter of a first example configuration, in which light passes a raindrop detection filter of the optical filter, and then received by each photodiode on the image sensor, and information corresponding to the received light or information of each image capture pixel is shown;

FIG. 17(a) shows a schematic cross-sectional view of the raindrop detection filter of the optical filter, and the image sensor cut at a line A-A shown in FIG. 16, and FIG. 17(b) shows a schematic cross-sectional view of schematic cross-sectional view of the raindrop detection filter of the optical filter, and the image sensor cut at a line B-B shown in FIG. 16;

FIG. 24 shows one example of aperture for restricting or limiting light amount of light, passing a non-light-separation area of a light separation filter of the optical filter;

FIG. 25 shows another example of aperture for restricting or limiting light amount of light, passing a non-light-separation area of a light separation filter of the optical filter;

FIG. 26 shows another example of aperture for restricting or limiting light amount of light, passing a non-light-separation area of a light separation filter of the optical filter;

FIG. 27 shows another example of aperture for restricting or limiting light amount of light, passing a non-light-separation area of a light separation filter of the optical filter;

FIG. 28 shows another example of aperture for restricting or limiting light amount of light, passing a non-light-separation area of a light separation filter of the optical filter;

FIG. 29 shows another example of aperture for restricting or limiting light amount of light, passing a non-light-separation area of a light separation filter of the optical filter;

FIGS. 40(a) and 40(b) are example photos captured for the same image capturing area including a metal-object on a road surface, in which FIG. 40(a) shows a monochrome luminance image of non-separated light/non-polarized light, and FIG. 40(b) shows a polarization-light-based image of non-separated light;

FIGS. 42(a) and 42(b) are example photos captured for the same image capturing area including 3D object, in which FIG. 42(a) shows a monochrome luminance image of non-separated light/non-polarized light, and FIG. 42(b) shows a polarization-light-based image of non-separated light;

FIGS. 45(a) and 45(b) are example photos captured for the same image capturing area including an road-side end, in which FIG. 45(a) shows a monochrome luminance image of non-separated light/non-polarized light, and FIG. 45(b) shows a polarization-light-based image of non-separated light;

FIGS. 47(a) and 47(b) are example photos captured for the same image capturing area including a lane captured under a rainy weather, in which FIG. 47(a) shows a monochrome luminance image of non-separated light/non-polarized light, and FIG. 47(b) shows a polarization-light-based image of non-separated light;

FIG. 49(a) is an example captured image when raindrops adhere on an outer face of a windshield, and FIG. 49(b) is an example captured image when raindrops do not adhere on an outer face of a windshield.

Figure 1:
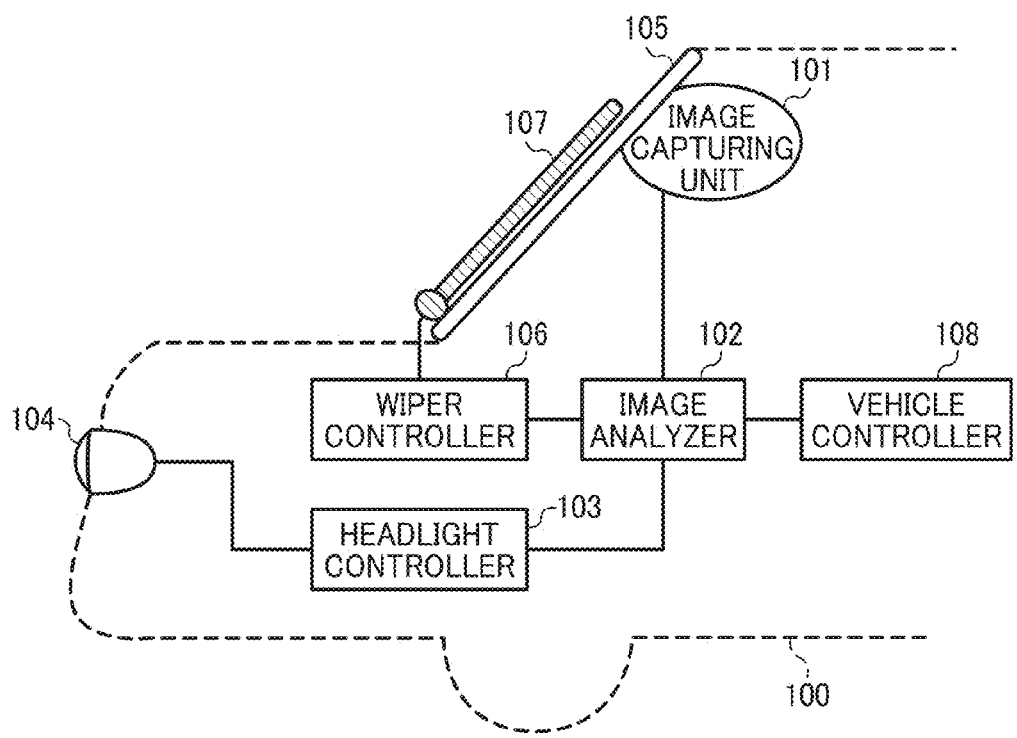
FIG. 1 shows a schematic configuration of a control system to control vehicle-installed devices according to an example embodiment.

The accompanying drawings are intended to depict exemplary embodiments of the present invention and should not be interpreted to limit the scope thereof. The accompanying drawings are not to be considered as drawn to scale unless explicitly noted, and identical or similar reference numerals designate identical or similar components throughout the several views.

DETAILED DESCRIPTION OF EXEMPLARY EMBODIMENTS

A description is now given of exemplary embodiments of the present invention. It should be noted that although such terms as first, second, etc. may be used herein to describe various elements, components, regions, layers and/or sections, it should be understood that such elements, components, regions, layers and/or sections are not limited thereby because such terms are relative, that is, used only to distinguish one element, component, region, layer or section from another region, layer or section. Thus, for example, a first element, component, region, layer or section discussed below could be termed a second element, component, region, layer or section without departing from the teachings of the present invention.

In addition, it should be noted that the terminology used herein is for the purpose of describing particular embodiments only and is not intended to be limiting of the present invention. Thus, for example, as used herein, the singular forms "a", "an" and "the" are intended to include the plural forms as well, unless the context clearly indicates otherwise. Moreover, the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Furthermore, although in describing views shown in the drawings, specific terminology is employed for the sake of clarity, the present disclosure is not limited to the specific terminology so selected and it is to be understood that each specific element includes all technical equivalents that operate in a similar manner and achieve a similar result. Referring now to the drawings, an apparatus or system according to an example embodiment is described hereinafter.

A description is given of a control system to control vehicle-installed devices according to an example embodiment, in which an image capturing device is installed in a vehicle. The image capturing device can be used with the control system to control vehicle-installed devices, but the image capturing device can be applied for other systems having an object detector or object detection apparatus to conduct the detection of objects based on captured images, which may be captured by the image capturing device. The vehicle may not be limited to any specific vehicles but may include various types of vehicles such as automobiles, ship, robots or the like.

FIG. 1 shows a schematic configuration of a control system to control vehicle-installed devices according to an example embodiment. A vehicle 100 such as automobiles may include a control system to control vehicle-installed devices, and an image capturing device. Such vehicle 100 may be referred to as a detector-equipped vehicle in this disclosure. In this disclosure, for the simplicity of explanation, the vehicle 100 installs the detector to detect other objects on road or the like. It should be noted that other vehicles can be also installed with the detector. The detector can be used for any type of vehicles, moving objects used under various environmental conditions. The image capturing device can capture views of front area of the vehicle 100 as captured image data. Based on the captured image data, the control system to control vehicle-installed devices can conduct light control of headlight, wiper-drive control, control of other vehicle-installed devices, or the like.

The image capturing device used for the control system to control vehicle-installed devices is disposed in an image capturing unit 101. The image capturing device captures views of vehicle-front-area of the vehicle 100, wherein vehicle-front-area may be referred to as image capturing area or captured image area. For example, the image capturing device captures a vehicle-front-area of the vehicle 100 when the vehicle 100 is running. The image capturing device may be, for example, disposed near a rear-view mirror and a windshield 105 of the vehicle 100. Image data captured by the image capturing device of the image capturing unit 101 is input to the image analyzer 102.

The image analyzer 102 analyzes the captured image data, transmitted from the image capturing device, in which the image analyzer 102 can be used to compute information of other vehicles existing in a front direction of the vehicle 100 such as vehicle position, a point of the compass (e.g., north, south, east, west), and distance to other vehicles.

Further, the image analyzer 102 can be used to detect a substance on the windshield 105 such as raindrops, foreign particles, or the like. Further, the image analyzer 102 can be used to detect a detection-target object existing on road surfaces such as a lane (e.g., white line) or the like from the image capturing area. Further, the image analyzer 102 can be used to detect other vehicles. Specifically, by recognizing a tail lamp of other vehicles, the image analyzer 102 can detect a front-running vehicle (or vehicle ahead) running in front of the vehicle 100 in the same running direction, and by recognizing a headlight of other vehicles, the image analyzer 102 can detect an oncoming vehicle coming toward the vehicle 100 such as head-to-head direction. As such, the image analyzer 102 can be used as a substance detection processor, and an object detection processor.

The computation result of the image analyzer 102 can be transmitted to the headlight controller 103. For example, the headlight controller 103 generates control signals to control a headlight 104 based on distance data computed by the image analyzer 102, wherein the headlight 104 is one of devices installed in the vehicle 100.

Specifically, for example, a switching control of high beam/low beam of the headlight 104 is conducted, and a light-dimming control is partially conducted for the headlight 104 to prevent a projection of high intensity light of headlight of the vehicle 100 to eyes of drivers of front-running vehicles and oncoming vehicles, by which the drivers of other vehicles are not dazzled by light coming from the headlight of the vehicle 100 while providing the enough field of view for the driver of vehicle 100.

The computation result of the image analyzer 102 is also transmitted to the wiper controller 106. The wiper controller 106 controls a wiper 107 to remove a substance on the windshield 105 such as raindrops, foreign particles, or the like from the windshield 105 of the vehicle 100. The wiper controller 106 generates control signals to control the wiper 107 upon receiving the detection result of foreign particles from the image analyzer 102. When the control signals generated by the wiper controller 106 are transmitted to the wiper 107, the wiper 107 is activated to provide the field of view for the driver of the vehicle 100.

Further, the computation result of the image analyzer 102 is also transmitted to a vehicle controller 108, which controls the driving of the vehicle 100. If the vehicle 100 deviates or departs from the vehicle lane, defined by the lane (e.g., white line), based on the detection result of the lane detected by the image analyzer 102, the vehicle controller 108 activates an alarm or warning to the driver of the vehicle 100, and activates a cruise control system such as controlling of a steering wheel and/or brake of the vehicle 100.

Figure 2:
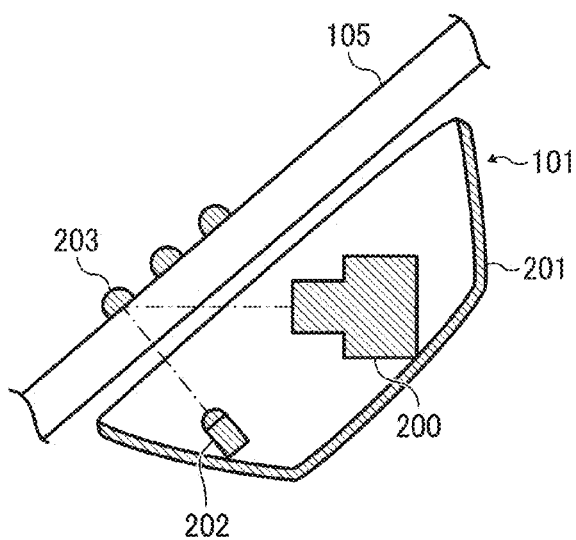
FIG. 2 shows a schematic configuration of an image capturing unit disposed for the control system of FIG. 1.
Figure 3:
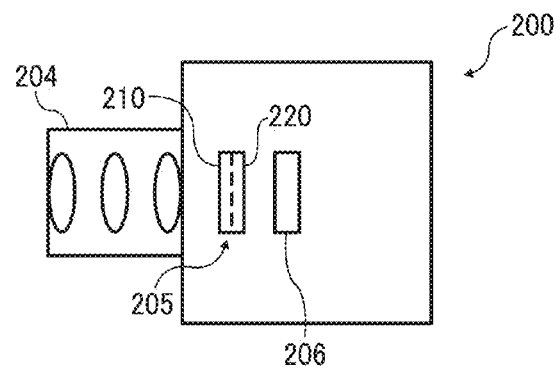
FIG. 3 shows a schematic configuration of an image capturing device disposed in the image capturing unit.

FIG. 2 shows a schematic configuration of the image capturing unit 101. FIG. 3 shows a schematic configuration of an image capture device disposed in the image capturing unit 101. As shown in FIG. 2, the image capturing unit 101 may include an image capture device 200, a light source 202, and a casing 201 that encases the image capture device 200 and the light source 202. The image capturing unit 101 may be attached to an interior side of the windshield 105 of the vehicle 100. As shown in FIG. 3, the image capture device 200 may include a capture lens 204, an optical filter 205, and an image sensor 206. The capture lens 204 may be also referred to as the image capture lens 204. The optical filter 205 may include a front-end filter 210 and a rear-end filter 220. The light source 202 emits the light toward the windshield 105, and the light reflected at the outer face of the windshield 105 (i.e., reflection light) may enter the image capture device 200.

In an example embodiment, the light source 202 emits a light to be used for detecting substances such as raindrops on the outer face of the windshield 105. Hereinafter, such substances may be referred to as a substance, adhered substance, or raindrop(s), as required.

If the raindrop 203 does not adhere on the outer face of the windshield 105, the light emitted from the light source 202 passes the interface between the outer face of the windshield 105 and outside air, and thereby the light does not enter the image capture device 200.

In contrast, if the raindrop 203 presents or adheres on the outer face of the windshield 105 as shown in FIG. 2, the difference of refractive index between the outer face of the windshield 105 and the raindrop 203 becomes smaller than the difference of refractive index between the outer face of the windshield 105 and the outside air. Therefore, the light emitted from the light source 202 passes the interface between the windshield 105 and the raindrop 203, and then reflects at the interface between the raindrop 203 and the outside air, and such reflected light enters the image capture device 200. Based on such difference caused by the presence of raindrop 203, the raindrop 203 on the windshield 105 can be detected using image data captured by the image capture device 200.

Further, as shown in FIG. 2, the casing 201 of the image capturing unit 101 and the windshield 105 encases the image capture device 200 and the light source 202. With such configuration using the casing 201, even if fogging occurs on the inner face of the windshield 105, fogging may not occur to a part of the windshield 105 encased by the image capturing unit 101. Therefore, the analysis failure by the image analyzer 102 due to the fogging of the windshield 105 can be prevented, and thereby various control operations can be effectively conducted based on the analysis result of the image analyzer 102.

Further, the fogging of the windshield 105 may be used to control an air-conditioning system of the vehicle 100, in which the fogging of the windshield 105 may be detected using image data captured by the image capture device 200. In such a case, an air-flow path may be formed at a part of the casing 201 so that a part of the windshield 105 facing the image capture device 200 has a same condition with other parts.

In the example embodiment, the position of focus of the capture lens 204 may be set at infinity, or between infinity and the windshield 105. With such setting, the detection of the raindrop 203 on the windshield 105, the detection of the front-running vehicle and the oncoming vehicle, and the detection of the lane (e.g., white line) can be conducted by obtaining information suitable for each type of detection from the image data captured by the image capture device 200.

For example, the raindrop 203 on the windshield 105 can be detected as follows. Typically, an image of a raindrop, captured as image data, may be observed as a circle shape. Therefore, when to recognize the would-be raindrop image or raindrop image candidate as a raindrop image (i.e., shape recognition processing), it is determined whether a would-be raindrop image or raindrop image candidate in the captured image data has a circle shape.

Such shape recognition processing can be effectively conducted by setting the focus of the capture lens 204 at infinity, or between infinity and the windshield 105 rather than setting the focus of the capture lens 204 at the raindrop 203 present on the outer face of the windshield 105. If the focus of the capture lens 204 is set at infinity, or between infinity and the windshield 105, images may be captured with a given level of out-of-focused condition or defocused condition, in which shape recognition performance of raindrop such as recognizing the raindrop as a circle shape can be enhanced, and thereby the raindrop detection performance can be enhanced.

Figure 4:
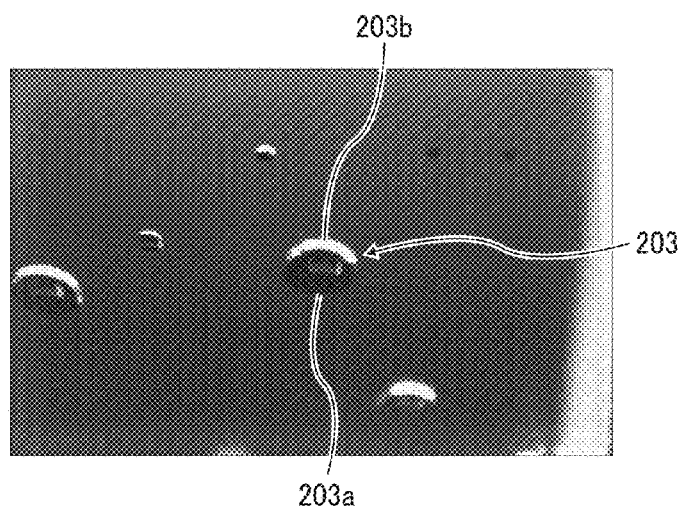
FIG. 4 shows an example of infra-red image data used for raindrop detection, which is captured by setting the focus of a capture lens at raindrops present on an outer face of a windshield of a detector-equipped vehicle.
Figure 5:
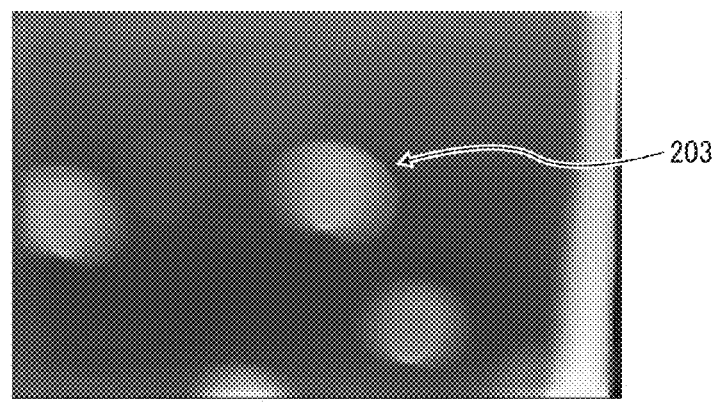
FIG. 5 shows an example of infra-red image data used for raindrop detection, which is captured by setting the focus of the capture lens at infinity.

FIG. 4 shows infra-red image data, which is captured as image data for the raindrop detection, in which the focus of the capture lens 204 is set at the raindrop 203 on the outer face of the windshield 105. FIG. 5 shows another infra-red image data, which is captured as image data for the raindrop detection, in which the focus of the capture lens 204 is set at infinity.

When the focus of the capture lens 204 is set at the raindrop 203 on the outer face of the windshield 105, a raindrop image may be captured with a background image 203*a* being projected on a raindrop as shown in FIG. 4. Such background image 203*a* may cause a detection malfunction of the raindrop 203. Further, as shown in FIG. 4, a raindrop boundary 203*b*, which is a part of raindrop, may become an arc-like shape having a greater intensity. The raindrop image having such a shape having greater intensity may change depending on the direction of sun light and/or position of streetlamp/streetlight, and such shape of raindrop image changes in various patterns. If the shape recognition processing is required to handle such various patterns, the processing load becomes great, and further, the recognition precision may deteriorate.

In contrast, when the focus of the capture lens 204 is set at infinity as shown in FIG. 5, images may be captured with a given level of out-of-focused condition or defocused condition. Therefore, a ghost image of the background image 203*a* may not be projected or included in the captured image data, and thereby a detection malfunction of the raindrop 203 can be reduced. Further, the shape of images of out-of-focused condition may not be changed so much even if the direction of sun light and/or the position of streetlamp/streetlight changes, and thereby the shape of raindrop image may not change so much, and thereby the shape of raindrop image can be recognized substantially a circle shape. Therefore, the processing load of the shape recognition processing for the raindrop 203 becomes small, and further, the recognition precision can be set high.

However, if the focus of the capture lens 204 is set at infinity, a tail lamp of the front-running vehicle running at a far distance ahead of the vehicle 100 may be recognized by one or so light receiving elements of the image sensor 206, which means the tail lamp light is received by one or so light receiving elements. In such a case, the tail lamp light may not be received by a red-light receiving element disposed for receiving the tail lamp color such as red, by which the tail lamp cannot be recognized, and thereby the front-running vehicle cannot be detected.

To avoid such situation, the focus of the capture lens 204 is not set at infinity, but preferably set at a point closer to the vehicle 100 compared to infinity. With such setting, the tail lamp of the front-running vehicle running at a far distance ahead of the vehicle 100 can be recognized as an image having out of focused or defocused condition, by which the numbers of the light receiving elements that can receive the light of tail lamp can be increased. Therefore, the recognition precision of the tail lamp can be enhanced, and thereby the detection precision of the front-running vehicle at a far distance ahead of the vehicle 100 can be enhanced.

The light source 202 of the image capturing unit 101 may be, for example, a light emitting diode (LED), a semiconductor laser such as laser diode (LD), or the like. Further, the wavelength of emission light of the light source 202, for example, may be visible light, infra-red light, or the like. However, the visible light emitted from the light source 202 may cause dazzling of drivers of the oncoming vehicle and pedestrians. Such dazzling can be avoided using light having a wavelength longer than the wavelength of visible light and effectively receivable within the responsiveness of the image sensor 206. For example, the wavelength of the infra-red light having a wavelength range from 800 nm to 1000 nm can be used. In the example embodiment, the light source 202 emits the light having a wavelength range of the infra-red light.

When the image capture device 200 captures the infra-red light reflected from the windshield 105, the image sensor 206 of the image capture device 200 receives infra-red light emitted from the light source 202, and also ambient light coming as sun light including infra-red light. Such ambient light includes infra-red light having greater light intensity. To reduce the effect of the ambient light having greater light intensity to the infra-red light coming from the light source 202, the light emission amount of the light source 202 may be set greater than that of the ambient light. However, it is difficult to devise the light source 202 having the greater light emission amount.

Figure 6:
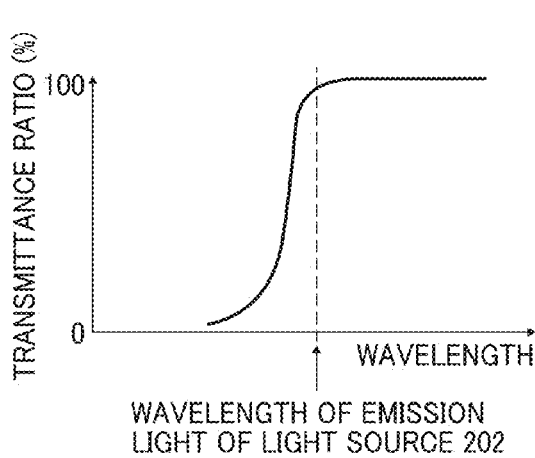
FIG. 6 shows a profile of filter property of a cut-filter applicable for image data captured for a raindrop detection process.
Figure 7:
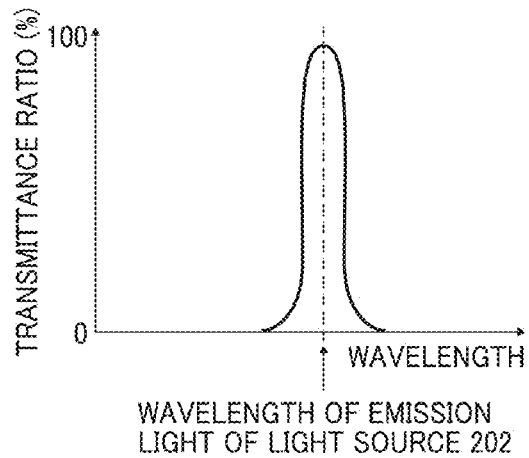
FIG. 7 shows a profile of filter property of a band-pass filter for image data captured for a raindrop detection process.

In view of such problem, in the example embodiment, for example, a suitable cut-filter or a band-pass filter may be used. As shown in FIG. 6, a cut-filter that cuts light having a wavelength smaller than a wavelength of emission light of the light source 202, can be used. Further, as shown in FIG. 7, a band-pass filter that passes through light having a specific wavelength of emission light of the light source 202, substantially matched to the peak of transmittance ratio of the light, can be used. As such, the image sensor 206 can effectively receive light emitted from the light source 202 using such filters. By using such filters, the light having a wavelength, which is other than the wavelength of emission light emitted from the light source 202, can be removed. Therefore, the image sensor 206 can receive the light emitted from the light source 202 with an amount relatively greater than the ambient light. Therefore, without using the light source 202 having greater light emission intensity, the light emitted from the light source 202 can be effectively received by the image sensor 206 while reducing the effect of the ambient light.

However, in the example embodiment, the raindrop 203 on the windshield 105 is detected based on the captured image data, and furthermore, the front-running vehicle and the oncoming vehicle are detected, and the lane (e.g., white line) is also detected based on the captured image data.

Therefore, if the light having a wavelength other than a wavelength of infra-red light emitted from the light source 202 is removed from an entire image, the image sensor 206 cannot receive light having a wavelength required to detect the front-running vehicle/oncoming vehicle and the lane, by which the detection of vehicle/oncoming vehicle and the lane cannot be conducted.

In view of such issue, in the example embodiment, an image area of captured image data is segmented to one detection image area used as a raindrop detection image area, and another detection image area used as a vehicle detection image area. The raindrop detection image area can be used to detect the raindrop 203 on the windshield 105. The vehicle detection image area can be used to detect the front-running vehicle/oncoming vehicle, and the lane (e.g., white line).

Therefore, the optical filter 205 includes a filter that can remove light having a wavelength band, which is other than infra-red light emitted from the light source 202. Such filter is disposed only for the raindrop detection image area.

Figure 8:
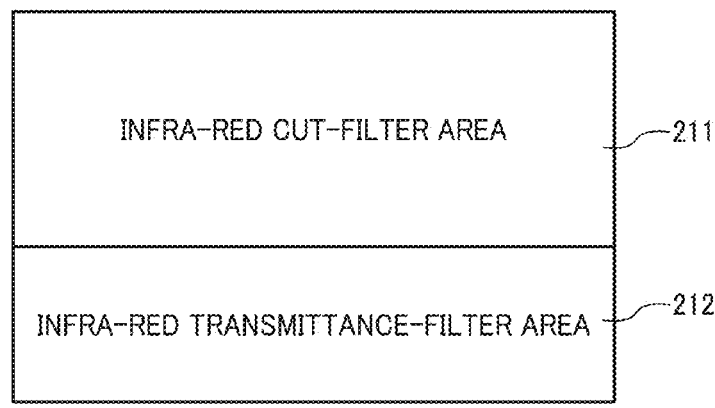
FIG. 8 shows a front view of a front-end filter disposed for an optical filter of the image capturing device of FIG. 3.
Figure 9:
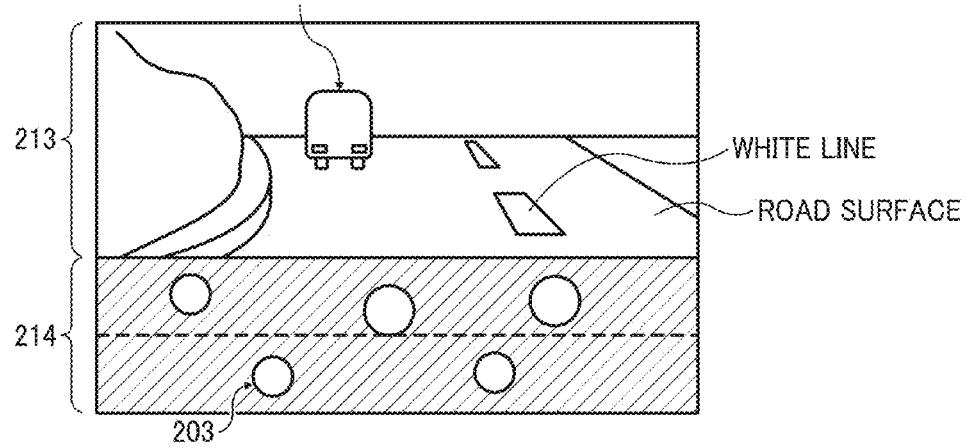
FIG. 9 shows an example of image generated from image data captured by the image capturing device of FIG. 3.

FIG. 8 shows a front view of a front-end filter 210 disposed for the optical filter 205. FIG. 9 shows an example of image generated from captured image data. As shown in FIG. 3, the optical filter 205 can be composed of the front-end filter 210 and the rear-end filter 220, stacked with each other in the light passing or propagation direction.

As shown in FIG. 8, the front-end filter 210 can be segmented into one filter area such as an infra-red cut-filter area 211, and another filter area such as an infra-red transmittance-filter area 212. The infra-red cut-filter area 211 is disposed for a vehicle detection image area 213, which may be an upper two-thirds (⅔) of one image capturing area. The infra-red transmittance-filter area 212 is disposed for a raindrop detection image area 214, which may be a lower one-third (⅓) of one image capturing area. The infra-red transmittance-filter area 212 may be devised by using the cut-filter shown in FIG. 6 or the band-pass filter shown in FIG. 7.

The image capturing area can be segmented into an upper part and a lower part. Typically, an image of headlight of the oncoming vehicle, an image of tail lamp of the front-running vehicle, and an image of the lane (e.g., white line) are present at the upper part of the image capturing area, while an image of road surface, which exists in the front-direction and very close to the vehicle 100, is present at the lower part of the image capturing area.

Therefore, information required to recognize or identify the headlight of the oncoming vehicle, the tail lamp of the front-running vehicle, and the lane is present mostly in the upper part of the image capturing area, and thereby information present in the lower part of the image capturing area may not be relevant for recognizing the oncoming vehicle, the front-running vehicle, and the lane.

Therefore, when an object detection process such as detecting the oncoming vehicle, the front-running vehicle, and/or the lane, and a raindrop detection are to be conducted concurrently based on the captured image data, the lower part of the image capturing area is corresponded to the raindrop detection image area 214, and the upper part of the image capturing area is corresponded to the vehicle detection image area 213 as shown in FIG. 9. The front-end filter 210 is preferably segmented into areas corresponding to the vehicle detection image area 213 and the raindrop detection image area 214.

When the image capturing direction of the image capture device 200 is moved to a downward direction, a hood or bonnet of the vehicle 100 may appear at the lower part of the image capturing area. In such a case, sun light or the tail lamp of the front-running vehicle reflected on the hood of the vehicle 100 becomes ambient light. If the ambient light is included in the captured image data, the headlight of the oncoming vehicle, the tail lamp of the front-running vehicle, and the lane may not be recognized correctly.

In the example embodiment, because the cut-filter (FIG. 6) or the band-pass filter (FIG. 7) can be disposed at a position corresponding to the lower part of the image capturing area, the ambient light such as sun light, and the light of tail lamp of the front-running vehicle reflected from the hood can be removed. Therefore, the recognition precision of the headlight of the oncoming vehicle, the tail lamp of the front-running vehicle, and the lane can be enhanced.

Further, in the example embodiment, due to the optical property of the capture lens 204, the upside/downside of an image in the image capturing area and the upside/downside of an image in the image sensor 206 becomes opposite. Therefore, if the lower part of the image capturing area is used as the raindrop detection image area 214, the upper part of the front-end filter 210 of the optical filter 205 may be configured using the cut-filter (FIG. 6) or the band-pass filter (FIG. 7).

The detection of the front-running vehicle can be conducted by recognizing the tail lamp of the front-running vehicle in the captured image. Compared to the headlight of the oncoming vehicle, the light amount of the tail lamp is small. Further, ambient light such as streetlamp/streetlight or the like may exist in the image capturing area. Therefore, the tail lamp may not be detected with high precision if only the light intensity data is used.

To recognize the tail lamp effectively, spectrum information can be used. For example, based on received light amount of the red-color light, the tail lamp can be recognized effectively. In the example embodiment, as described later, the rear-end filter 220 of the optical filter 205 may be disposed with a red-color filter or cyan-color filter matched to a color of the tail lamp, which is a filter that can pass through only a wavelength band matched to a color used for the tail lamp, so that the received light amount of the red-color light can be detected effectively.

However, each of the light receiving elements configuring the image sensor 206 may have sensitivity set to infra-red light. Therefore, if the image sensor 206 receives light including infra-red light, the captured image may become red-color-like image as a whole. Then, it may become difficult to recognize a red-color image portion corresponding to the tail lamp.

In view of such situation, in the example embodiment, the front-end filter 210 of the optical filter 205 includes the infra-red cut-filter area 211 corresponding to the vehicle detection image area 213. By employing such infra-red cut-filter area 211, the infra-red wavelength band can be removed from the captured image data used for the recognition of the tail lamp, by which the recognition precision of tail lamp can be enhanced.

Figure 10:
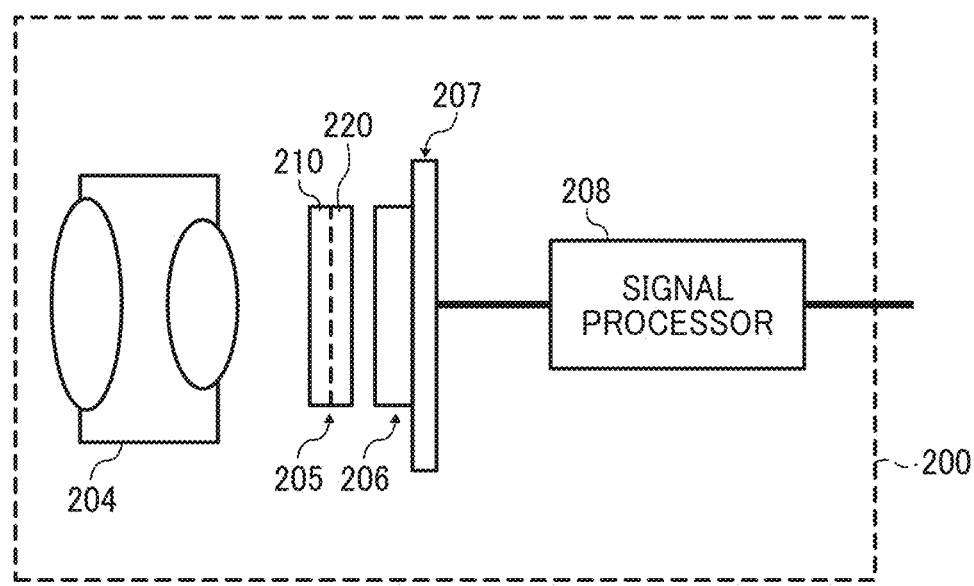
FIG. 10 shows a schematic configuration of the image capturing device of FIG. 3.

FIG. 10 shows a schematic configuration of the image capture device 200. The image capture device 200 may include the capture lens 204, the optical filter 205, a sensor board 207, and a signal processor 208. The sensor board 207 includes the image sensor 206 composed of a two-dimensional pixel array, which can be configured by arraying a number of light receiving elements in two dimensional directions.

Each of light receiving elements of the image sensor 206 receives light having a given amount, and the sensor board 207 outputs analog electrical signals corresponding to the received light amount to the signal processor 208. Upon receiving the analog electrical signals, the signal processor 208 converts the analog electrical signals to digital electrical signals to generate and output the captured image data.

Light coming from the image capturing area including objects (or detection-target object) passes the capture lens 204 and the optical filter 205, and then the image sensor 206 converts the received light to electrical signals based on the light intensity. When the signal processor 208 receives electrical signals such as analog signals output from the image sensor 206, the signal processor 208 converts the analog signals to digital signal to be used as captured image data, including brightness or intensity data of each pixel on the image sensor 206. The signal processor 208 outputs the captured image data to a later stage unit with horizontal/vertical synchronization signals of image.

Figure 11:
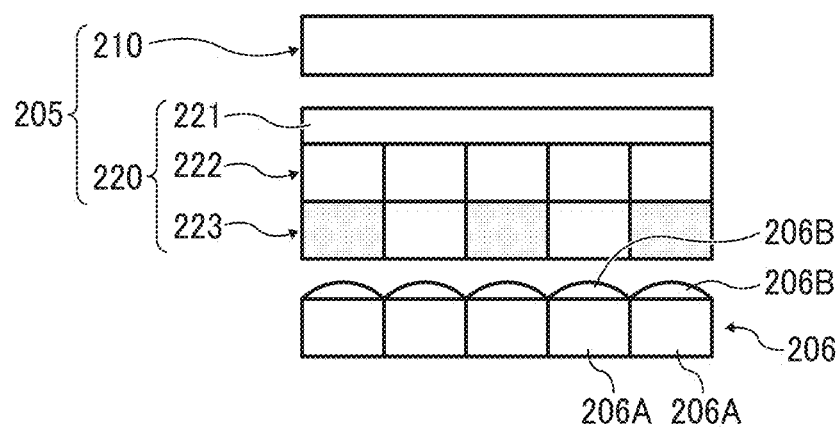
FIG. 11 shows a schematic cross-sectional configuration of an optical filter and an image sensor of the image capturing device viewed from a direction perpendicular to a light passing direction.

FIG. 11 shows a schematic configuration of the optical filter 205 and the image sensor 206, viewed from a direction perpendicular to the light passing or propagation direction. The image sensor 206 is a sensor employing, for example, a charge coupled device (CCD), a complementary metal oxide semiconductor (CMOS), or the like, and each of the light receiving elements of image sensor 206 may be, for example, photodiode 206A. The photodiodes 206A are arrayed as a two-dimensional array, in which each photodiode 206A may correspond to each pixel. To enhance the light collection efficiency of the photodiode 206A, a micro lens 206B is disposed at the incidence side of the photodiode 206A. The image sensor 206 can be bonded to a printed wiring board (PWB) using known methods such as wire bonding to configure the sensor board 207. Hereinafter, the photodiode 206A may mean one photodiode or a plurality of photodiodes.

The optical filter 205 is disposed at a close proximity of the micro lens 206B of the image sensor 206. As shown in FIG. 11, the rear-end filter 220 of the optical filter 205 includes a translucent filter board 221, a polarized-light filter 222, and a light-separation filter 223. The rear-end filter 220 employs a multiple-layered structure by forming the polarized-light filter 222 on a translucent filter board 221, and then forming the light-separation filter 223 on the polarized-light filter 222. The polarized-light filter 222 and the light-separation filter 223 are segmented into areas, and each segmented area of the polarized-light filter 222 and each segmented area of the light-separation filter 223 correspond to the corresponding photodiode 206A of the image sensor 206.

The optical filter 205 and the image sensor 206 can be arranged in the image capture device 200 by setting a space between the optical filter 205 and the image sensor 206. Further, the optical filter 205 and the image sensor 206 can be arranged in the image capture device 200 by closely contacting the optical filter 205 to the image sensor 206, in which the boundary of the optical filter 205 including the polarized-light filter 222 and the light-separation filter 223, and the boundary of the photodiode 206A on the image sensor 206 can be matched easily. For example, the optical filter 205 and the image sensor 206 can be bonded, for example, using an ultra violet (UV) bonding agent, or the optical filter 205 and the image sensor 206 can be supported with each other by a spacer disposed therebetween at non-pixel areas not used for image capturing, and four sides of the optical filter 205 and the image sensor 206 can be bonded by UV bonding or heat bonding.

Figure 12:
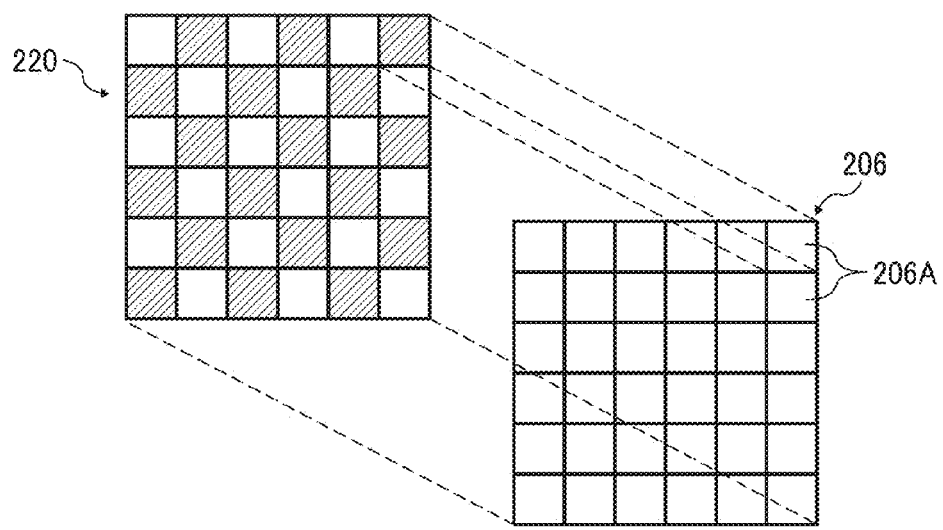
FIG. 12 shows an example of area segmentation of a polarization filter and a light separation filter of an optical filter.

FIG. 12 shows an area segmentation pattern of the polarized-light filter 222 and the light-separation filter 223 of the rear-end filter 220 of the optical filter 205. The polarized-light filter 222 includes areas such as a first area and a second area, and the light-separation filter 223 includes areas such as the first area and the second area. Such first area and second area set for the polarized-light filter 222 and the light-separation filter 223 are matched to corresponding photodiode 206A on the image sensor 206. With such a configuration, each photodiode 206A on the image sensor 206 can receive light that passes the first area or the second area set for the polarized-light filter 222 or the light-separation filter 223. Depending on the types of area set for the polarized-light filter 222 or the light-separation filter 223, the polarized light information and/or spectrum information can be obtained by the image sensor 206.

In the example embodiment, the image sensor 206 may use an image capturing element for capturing monochrome images, but the image sensor 206 can use an image capturing element for capturing color images with a use of a color filter disposed for each image capture pixel corresponding to the image capturing element of color images. When the image capturing element of color images is used, depending on the property of color filter, light transmission performance of each polarized-light filter 222 and light-separation filter 223 can be adjusted.

(Optical Filter: First Example Configuration)

Figure 13:
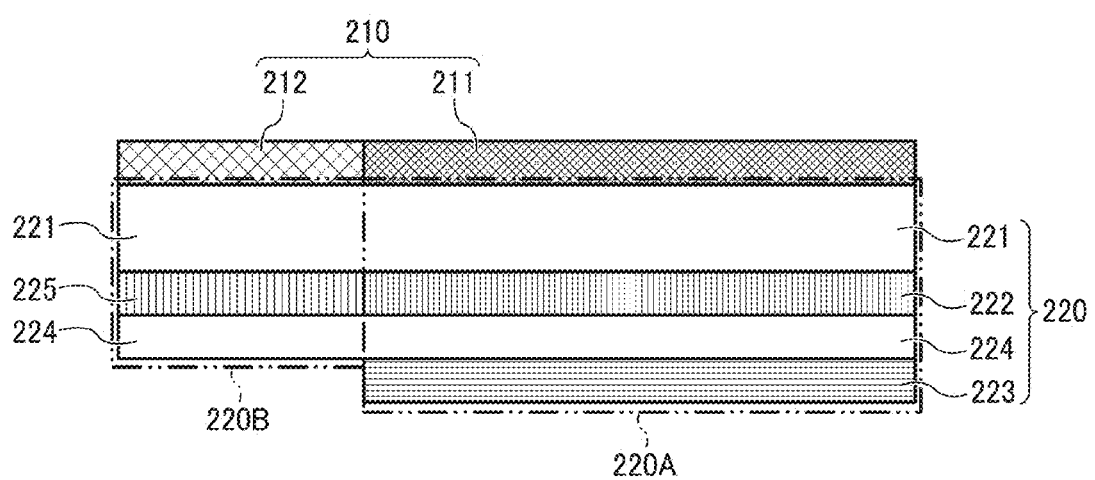
FIG. 13 shows a schematic cross-sectional view of an optical filter.

A description is given of a first example configuration of the optical filter 205 with reference to FIG. 13, which shows a schematic cross-sectional view of the optical filter 205. The rear-end filter 220 of the optical filter 205 includes a vehicle detection filter 220A and a raindrop detection filter 220B. The vehicle detection filter 220A corresponding to the vehicle detection image area 213, and the raindrop detection filter 220B corresponding to the raindrop detection image area 214 may employ different layered structures. Specifically, the vehicle detection filter 220A includes the light-separation filter 223 while the raindrop detection filter 220B does not include the light-separation filter 223. Further, the vehicle detection filter 220A includes a polarized-light filter 222, and the raindrop detection filter 220B includes a polarized-light filter 225, wherein the polarized-light filters 222 and 225 employ different structures.

FIG. 14 shows an example pixel configuration of the optical filter 205 of the first example configuration, in which light passes the vehicle detection filter 220A of the optical filter 205, and then received by each photodiode 206A on the image sensor 206, and information corresponding to the received light or information of each image capture pixel is shown. FIG. 15(a) shows a schematic cross-sectional view of the vehicle detection filter 220A of the optical filter 205, and the image sensor 206 cut at a line A-A shown in FIG. 14. FIG. 15(b) shows a schematic cross-sectional view of the vehicle detection filter 220A of the optical filter 205, and the image sensor 206 cut at a line B-B shown in FIG. 14.

In the first example configuration of the optical filter 205, as shown in FIGS. 15(a) and 15(b), the vehicle detection filter 220A employs a multiple-layered structure including the translucent filter board 221, the polarized-light filter 222, and the light-separation filter 223. Specifically, the polarized-light filter 222 is formed on the translucent filter board 221, and the light-separation filter 223 is formed on the polarized-light filter 222. The polarized-light filter 222 has a wire grid structure, and a convex/concave-like structure may be formed when the polarized-light filter 222 is formed as multiple layers.

If the light-separation filter 223 is formed on such convex/concave-like structure of the polarized-light filter 222, the light-separation filter 223 may be formed along the convex/concave-like structure, by which the light-separation filter 223 may be formed with uneven thickness layer, by which expected light-separation performance may not be obtained. Therefore, when preparing the optical filter 205, a top side of layers of the polarized-light filter 222 is filled with a filler agent 224 to form a flat face, and then the light-separation filter 223 is formed on the flat face.

The filler agent 224 is made from materials not having polarization property, by which the polarized-light filter 222 can function effectively because the filler agent 224 filling the convex/concave-like structure and forming the flat face does not affect the function of the polarized-light filter 222. A flat face processing using the filler agent such as the filler agent 224 can be conducted by a known method such as spin-on-glass (SOG) method, but not limited thereto.

In the first example configuration, the first area of the polarized-light filter 222 corresponds to a perpendicular direction polarization light area, in which only the perpendicular polarized light component oscillating in parallel to the image capture pixels, arranged along the vertical row of the image sensor 206 (perpendicular direction), is selected and passed through.

The second area of the polarized-light filter 222 corresponds to a horizontal direction polarization light area, in which only the horizontal polarized light component oscillating in parallel to the image capture pixels, arranged along the horizontal row of the image sensor 206 (horizontal direction), is selected and passed through.

Further, the first area of the light-separation filter 223 corresponds to a red color separation area to selectively pass through only the light having a red color wavelength band, which is included in the light passed through the polarized-light filter 222. Further, the second area of the light-separation filter 223 corresponds to a non-light-separation area to pass through the light without selecting wavelength of light.

In the first example configuration, as shown in FIG. 14, an portion enclosed by dotted line indicates four image capture pixels "a, b, e, f" that configure one-image pixel for the captured image data. Such four image capture pixels "a, b, e, f" include two adjacent pixels in one direction and two adjacent pixels in another one direction, adjacent to the two adjacent pixels in one direction.

In FIG. 14, the image capture pixel "a" receives light that has passed through the perpendicular direction polarization light area (i.e., first area) of the polarized-light filter 222 of the optical filter 205, and then passed through the red color separation area (i.e., first area) of the light-separation filter 223. Therefore, the image capture pixel "a" receives the light of the perpendicular polarized light (P in FIG. 14) and of the red color wavelength band (R in FIG. 14) as indicated as light P/R.

Further, in FIG. 14, the image capture pixel "b" receives light that has passed through the perpendicular direction polarization light area (i.e., first area) of the polarized-light filter 222 of the optical filter 205, and then passed through the non-light-separation area (i.e., second area) of the light-separation filter 223. Therefore, the image capture pixel "b" receives the light of the perpendicular polarized light (P in FIG. 14) and of non-light-separation (C in FIG. 14) as indicated as light P/C.

Further, in FIG. 14, the image capture pixel "e" receives light that has passed through the horizontal direction polarization light area (i.e., second area) of the polarized-light filter 222 of the optical filter 205, and then passed through the non-light-separation area (i.e., second area) of the light-separation filter 223. Therefore, the image capture pixel "e" receives the light of the horizontal polarized light (S in FIG. 14) and of non-light-separation (C in FIG. 14) as indicated as light S/C.

Further, in FIG. 14, the image capture pixel "f" receives light that has passed through the perpendicular direction polarization light area (i.e., first area) of the polarized-light filter 222 of the optical filter 205, and then passed through the red color separation area (i.e., first area) of the light-separation filter 223. Therefore, as similar to the image capture pixel "a," the image capture pixel "f" receives the light of the perpendicular polarized light (P in FIG. 14) and of the red color wavelength band (R in FIG. 14) as indicated as light P/R.

With such configuration, in the first example configuration, following images can be obtained: based on output signals of the image capture pixel "a" and the image capture pixel "f," the perpendicular polarized light image of red-color light for one-image pixel can be obtained; based on output signals of the image capture pixel "b," the perpendicular polarized light image of non-separated light for one-image pixel can be obtained; and based on output signals of the image capture pixel "e," the horizontal polarized light image of non-separated light for one-image pixel can be obtained.

Therefore, in the first example configuration, three types of captured image data can be obtained by one-time image capturing operation, wherein three types of captured image data are the perpendicular polarized light image of red-color light, the perpendicular polarized light image of non-separated light, and the horizontal polarized light image of non-separated light.

As for such captured image data, the numbers of image pixel becomes smaller than the numbers of image capture pixels, in which an image having a higher resolution level can be obtained by using known methods such as image interpolation technique.

For example, when to obtain the perpendicular polarized light image of red-color light having a higher resolution level for one image pixel, as for the image capture pixels "a" and "f," information of the perpendicular polarized light image for red-color light received by the image capture pixels "a" and "f" are used as there are, and as for the image capture pixel "b," an average value of the image capture pixels "a, c, f, j" surrounding the image capture pixel "b" is used as information of the perpendicular polarized light component P for red-color light.

Further, when to obtain the horizontal polarized light image of non-separated light having a higher resolution level for one image pixel, as for the image capture pixel "e," information of the horizontal polarized light component S of non-separated light received by the image capture pixel "e" is used as it is, and as for the image capture pixels "a, b, f," an average value of the horizontal polarized light component S of non-separated light of the image capture pixels "e, g," surrounding the image capture pixels "a, b, f," is used as the horizontal polarized light component S of non-separated light of the image capture pixels "a, b, f." Further, the horizontal polarized light component S of non-separated light of the image capture pixel "e" can be used as the horizontal polarized light component S of non-separated light of the image capture pixels "a, b, f."

The perpendicular polarized light image of red-color light, which that can be obtained as such, can be used for the recognition of the tail lamp. Because the horizontal polarized light component S is cut from the perpendicular polarized light image of red-color light, a red-color image, having suppressed disturbance by the red color light having the horizontal polarized light component S having high intensity, can be obtained, wherein the red color light having the horizontal polarized light component S having high intensity may be red color light reflected from the road surface, and red color light reflected from the dash board or instrument panel disposed in the vehicle 100 and observed as a ghost image. Therefore, by using the perpendicular polarized light image of red-color light for the recognition process of the tail lamp, the recognition performance of the tail lamp can be enhanced.

Further, the perpendicular polarized light image of non-separated light, for example, can be used for recognition of the lane (e.g., white line) and the headlight of the oncoming vehicle. Because the horizontal polarized light component S is cut from the perpendicular polarized light image of non-separated light, a non-separated light image, having suppressed disturbance by white light having the horizontal polarized light component S having high intensity, can be obtained, wherein the white light having the horizontal polarized light component S having high intensity may be light of headlight and/or streetlamp/streetlight reflected from the road surface, or a white light reflected from the dash board or instrument panel disposed in the vehicle 100 and observed as a ghost image.

Therefore, by using the perpendicular polarized light image of non-separated light for the recognition process of the lane (e.g., white line) and the headlight of the oncoming vehicle, the recognition performance of the lane and the headlight of the oncoming vehicle can be enhanced. Especially, on the wet road, light reflected from a wet area (e.g., water surface) covering the road surface has a greater amount of the horizontal polarized light component S. Therefore, by using the perpendicular polarized light image of non-separated light for the recognition process of the lane, the lane under the wet area of the wet road can be effectively recognized, by which the recognition performance of the lane and the headlight of the oncoming vehicle can be enhanced.

Further, the perpendicular polarized light image of non-separated light and the horizontal polarized light image of non-separated light can be compared with each other, and a compared result can be used as pixel value or pixel index value as described later. For example, as described later, by using the pixel index value, a metal-object in the image capturing area, wet/dry conditions of the road surface, an object such as three-dimensional object in the image capturing area, and the lane (e.g., white line) on the wet road can be recognized with high precision.

The captured images can be used as comparing images, which can be compared with each other using, for example, following values; 1) a difference between a pixel value of the perpendicular polarized light image of non-separated light and a pixel value of the horizontal polarized light image of non-separated light can be used difference-based image; 2) a ratio between a pixel value of the perpendicular polarized light image of non-separated light and a pixel value of the horizontal polarized light image of non-separated light can be used as a difference of image (ratio-based image); and 3) a difference of a pixel value of the perpendicular polarized light image of non-separated light and a pixel value of the horizontal polarized light image of non-separated light is divided by a sum of a pixel value of the perpendicular polarized light image of non-separated light and a pixel value of the horizontal polarized light image of non-separated light, wherein such computed value is a ratio defined polarization index (S−P)/(S+P), which may can be used as a polarization-light-based image.

FIG. 16 shows an example pixel configuration of the optical filter 205 of the first example configuration, in which light passes the raindrop detection filter 220B of the optical filter 205, and then received by each photodiode 206A on the image sensor 206. FIG. 17(a) shows a schematic cross-sectional view of the raindrop detection filter 220B of the optical filter 205, and the image sensor 206 cut at a line A-A shown in FIG. 16. FIG. 17(b) shows a schematic cross-sectional view of schematic cross-sectional view of the raindrop detection filter 220B of the optical filter 205, and the image sensor 206 cut at a line B-B shown in FIG. 16.

In the first example configuration of the optical filter 205, as shown in FIGS. 17(a) and 17(b), the raindrop detection filter 220B employs a multiple-layered structure including the translucent filter board 221, and the polarized light filter 225. The translucent filter board 221 is used as a common board for the vehicle detection filter 220A and the raindrop detection filter 220B. The polarized light filter 225 has a wire grid structure.

As similar to the polarized-light filter 222 set for the vehicle detection filter 220A, a top side of layers of the polarized light filter 225 is filled with the filler agent 224 to form a flat face, in which the polarized-light filter 222 and the polarized light filter 225 may be filled with the filler agent 224 to form the flat face thereon. However, different from the vehicle detection filter 220A, the light-separation filter 223 is not formed for the raindrop detection filter 220B.

In the example embodiment, objects disposed inside the vehicle 100 may be projected on the inner face of the windshield 105 as a ghost image. Such ghost image may occur when light coming from the object regularly reflects on the inner face of the windshield 105. Because such ghost image is generated by the regular reflection light, such ghost image may become ambient light having relatively greater light intensity. Therefore, if such ghost image is projected on or over the raindrop image on the raindrop detection image area 214, the precision of raindrop detection deteriorates.

Further, when the light emitted from the light source 202 is regularly reflected at the inner face of the windshield 105, such regular reflection light may be projected on or over the raindrop image on the raindrop detection image area 214. Such regular reflection light also becomes the ambient light, and thereby the precision of raindrop detection deteriorates.

Such ambient light that degrades the precision of raindrop detection may be regular light reflected regularly at the inner face of the windshield 105. Most of the polarization light component of the ambient light is a polarization light component having a polarization direction that is perpendicular with respect to the incidence plane of light. Such ambient light has the horizontal polarized light component S that oscillates in parallel to the horizontal row of image capture pixels of the image sensor 206 (horizontal direction).

In the optical filter 205 of the first example configuration, the polarized light filter 225 disposed for the raindrop detection filter 220B is set with a transmission axis that passes through only the perpendicular polarized light component P that oscillates in perpendicular direction.

The perpendicular polarized light component P, which oscillates in parallel along the vertical row of image capture pixels of the image sensor 206, correspond to a polarization light component having a polarization light direction parallel to a virtual plane (or incidence plane of light) including an optical axis of light emitted from the light source 202 to the windshield 105, and an optical axis of the capture lens 204.

With such a configuration, the light that can pass through the polarized light filter 225, disposed for the raindrop detection filter 220B, is only the perpendicular polarized light component P. The ambient light may occur as a ghost image projected on the inner face of the windshield 105, and as a regular reflection light, which may be generated when the light emitted from the light source 202 is reflected regularly on the inner face of the windshield 105. Most of the polarization light component of such ambient light is the horizontal polarized light component S. The above configuration of the polarized light filter 225, disposed for the raindrop detection filter 220B can cut the horizontal polarized light component S. As a result, the raindrop detection image area 214 can use perpendicular polarized light image prepared from the perpendicular polarized light component P, which has lesser effect of the ambient light. Therefore, the precision of raindrop detection conducted based on the image data captured for the raindrop detection image area 214 can be enhanced.

In the first example configuration, the front-end filter 210 includes the infra-red cut-filter area 211 and the infra-red transmittance-filter area 212 having a multi-layered film structure, and the infra-red cut-filter area 211 and the infra-red transmittance-filter area 212 have different layered structures. For example, the front-end filter 210 can be manufactured as follows by the vacuum deposition. At first, the infra-red transmittance-filter area 212 is formed by the vacuum deposition while masking the portion of the infra-red cut-filter area 211. Then, while masking the infra-red transmittance-filter area 212, the infra-red cut-filter area 211 is formed by the vacuum deposition.

Further, in the first example configuration, the polarized-light filter 222 of the vehicle detection filter 220A and the polarized light filter 225 of the raindrop detection filter 220B employ the wire grid structure, in which the vehicle detection filter 220A and the raindrop detection filter 220B are segmented into in two dimensional direction (area segmentation).

The polarized-light filter 222 is segmented using two types of areas, in which one area is used for a perpendicular direction polarization light area, and another area is used for a horizontal direction polarization light area. Each of the areas may correspond to each corresponding image capture pixel. The transmission axis of perpendicular direction polarization light area and the transmission axis of the horizontal direction polarization light area extend in directions that are perpendicular with each other.

Further, in contrast, the polarized light filter 225 is segmented using one type of area, in which such area has the transmission axis that passes only the perpendicular polarized light component P. Each of the areas may correspond to each corresponding image capture pixel.

The polarized-light filters 222 and 225 employing different structures can be formed on the same translucent filter board 221 using, for example, a template for metal wire patterning used for forming a wire grid structure, in which by adjusting the groove direction, the adjustment of long side direction of the metal wire for each area can be conducted easily.

Further, in the first example configuration, the infra-red cut-filter area 211 may not be disposed for the optical filter 205, but the infra-red cut-filter area 211 can be disposed at the capture lens 204 instead, by which the optical filter 205 can be manufactured easily.

Further, the infra-red cut-filter area 211 may not be disposed for the front-end filter 210. For example, a light separation filter that can pass through only the perpendicular polarized light component P can be formed on the raindrop detection filter 220B of the rear-end filter 220, in which the infra-red cut-filter area 211 is not formed for the front-end filter 210.

Figure 18:
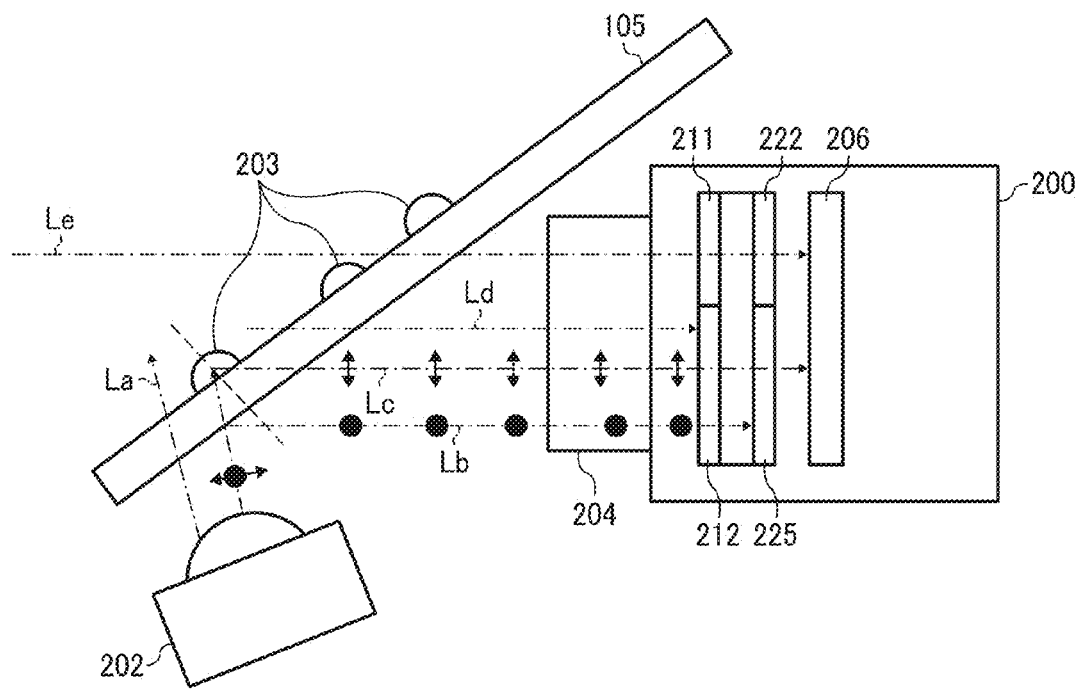
FIG. 18 shows a schematic configuration of the image capture device and the light source, and light beams related to a detection process.

FIG. 18 shows a schematic configuration of the image capture device 200 and the light source 202, and light beams which may be used for the raindrop detection. The light source 202 may be disposed at a given position so that a direction of regular light reflected at the outer face of the windshield 105 can be substantially matched to the optical axis of the capture lens 204.

(Light Beam La)

Light beam La of FIG. 18 is a light, emitted from the light source 202 and then passes through the windshield 105. When the raindrop 203 does not adhere on the outer face of the windshield 105, a light emitting from the light source 202 and forwarding to the windshield 105 passes through the windshield 105, and goes out of the vehicle 100 as indicted as the light beam La of FIG. 18. Such light beam La may enter human eyes, which may cause injury. Therefore, the light source 202 may preferably employ a light source having a wavelength and light intensity that may not cause eyes injury even if the light enters human eyes (eye-safe light). Further, if the light source 202 is positioned as shown in FIG. 18, the light entering the windshield 105 goes upward in the vertical direction, by which the probability of light-hitting of human eyes can be preferably reduced.

(Light Beam Lb)

Light beam Lb of FIG. 18 is a light, emitted from the light source 202 and reflected regularly on the inner face of the windshield 105 and then entering the image capture device 200. As such, some of the light, emitting from the light source 202 and going toward the windshield 105, may regularly be reflected at the inner face of the windshield 105. Such regular reflection light (light beam Lb of FIG. 18) has a polarization light component, wherein the polarization light component of light beam Lb is mostly S-polarized light component (or horizontal polarized light component S), which oscillates in a direction perpendicular to a light incidence plane (or oscillates in a direction perpendicular to a sheet of FIG. 18). Such light beam Lb (i.e., regular reflection light) reflected regularly on the inner face of the windshield 105 does not fluctuate whether the raindrop 203 adheres or not on the outer face of the windshield 105, and such light beam Lb is not necessary for the raindrop detection. Further, the light beam Lb becomes ambient light that degrades the detection precision of the raindrop detection. In the first example configuration, the light beam Lb (horizontal polarized light component S) is cut by the polarized light filter 225 disposed for the raindrop detection filter 220B. Therefore, deterioration of the precision of raindrop detection due to the light beam Lb can be reduced, suppressed, or prevented.

(Light Beam Lc)

Light beam Lc of FIG. 18 is a light, emitted from the light source 202 and passing through the inner face of the windshield 105, reflected at a raindrop on the outer face of the windshield 105, and then entering the image capture device 200. Some of the light, emitting from the light source 202 and going toward the windshield 105, passes through the inner face of the windshield 105 as passing light. Such passing light includes the perpendicular polarized light component P greater than the horizontal polarized light component S.

If the raindrop 203 adheres on the outer face of the windshield 105, the passing light, which has passed through the inner face of the windshield 105, does not go out of the windshield 105, different from the light beam La, but the passing light reflects inside the raindrop for multiple times, and passes through in the windshield 105 again toward the image capture device 200, and enters the image capture device 200.

In the optical filter 205 of the image capture device 200, the infra-red transmittance-filter area 212 disposed for the front-end filter 210 is configured to pass through the light having a wavelength of emission light of the light source 202, which is infra-red light. Therefore, the light beam Lc passes through the infra-red transmittance-filter area 212.

Further, the polarized light filter 225 disposed for the raindrop detection filter 220B of the rear-end filter 220 employs the wire grid structure by forming the long side direction of metal wire into a shape to pass through the perpendicular polarized light component P, by which the light beam Lc can also pass through the polarized light filter 225. Therefore, the light beam Lc reaches the image sensors 206, and the raindrop detection can be conducted using the light received by the image sensor 206.

(Light Beam Ld)

Light beam Ld in FIG. 18 is a light, coming from the outside of the windshield 105 and passing through the windshield 105, and then entering the raindrop detection filter 220B of the image capture device 200. The light beam Ld may become ambient light when to conduct the raindrop detection, but most of the light component having a given wavelength included in the light beam Ld can be cut by the infra-red transmittance-filter area 212, which passes the infra-red light, disposed for the front-end filter 210 of the optical filter 205 of the first example configuration. Therefore, deterioration of the precision of raindrop detection due to the light beam Ld can be reduced, suppressed, or prevented.

(Light Beam Le)

Light beam Le of FIG. 18 is light, coming from the outside of the windshield 105 and passing through the windshield 105, and then entering the vehicle detection filter 220A of the image capture device 200. The infra-red cut-filter area 211, disposed for the front-end filter 210 of the optical filter 205, cuts infra-red light included in the light beam Le, and thereby only visible light of the light beam Le can be captured and received by the image sensor 206 as captured image data. Such captured image data can be used to detect the headlight of the oncoming vehicle, the tail lamp of the front-running vehicle, and the lane (e.g., white line).

In the first example configuration, the light source 202 may use one light source as above described. However, the light source 202 can use a plurality of light sources. When the plurality of light sources is used, as for the polarized light filter 225 used for the raindrop detection filter 220B, a plurality of polarization filter areas is set for the polarized light filter 225 while differentiating the transmission axes of the polarization filter areas with each other, in which each of the plurality of polarization filter areas, segmented into areas, is aligned with corresponding image capturing pixel, arranged in two dimensional direction.

Each of the polarization filter areas sets a transmission axis that can pass through only a polarization light component having a polarization light direction parallel to a virtual plane including an optical axis of a light source having input the greatest incidence light amount among a plurality of the light sources, for a concerned polarization filter area, and an optical axis of the capture lens 204.

Further, in both cases that the light source 202 is one light source and a plurality of light sources, the transmission axis direction of the polarized light filter 225, which can effectively remove ambient light reflected regularly at the inner face of the windshield 105, may vary depending on reflection points of ambient light at the inner face of the windshield 105.

The windshield 105 disposed for an automobile is not only slanted toward the forward direction, but also greatly warped toward the rearward direction along the left/right direction from the center portion to the both side end portions of the automobile to enhance aerodynamic characteristics of the automobile. In such a configuration, in the captured image in the raindrop detection image area 214, ambient light can be effectively cut at the center portion of image, but ambient light may not be effectively cut at the end portion of image.

Figure 19:
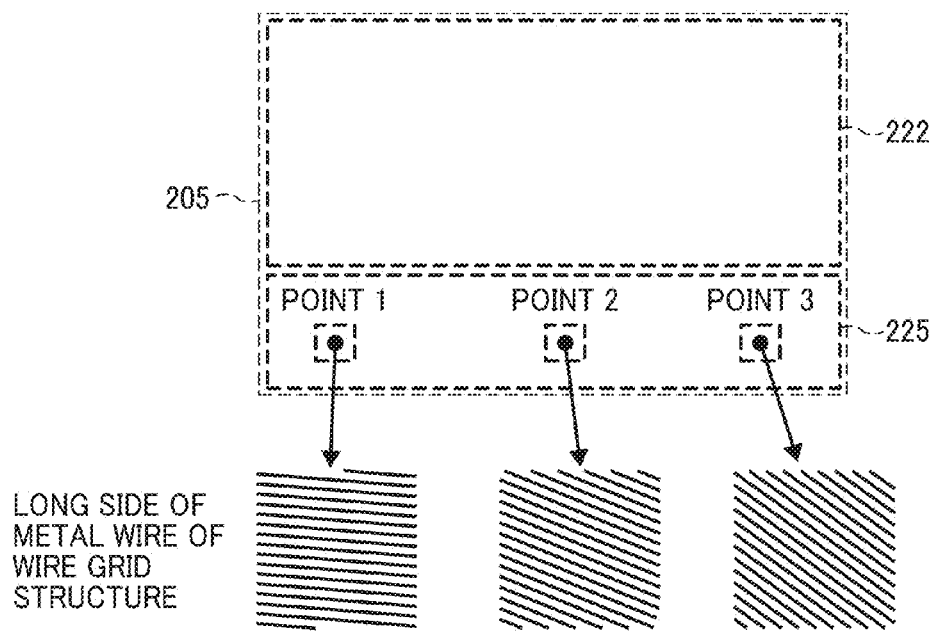
FIG. 19 shows difference of long side direction of metal wire of a wire grid structure at each point in a polarized light filter disposed for the raindrop detection filter of the optical filter.

FIG. 19 shows difference of the long side direction of metal wire of the wire grid structure at each point such as point 1 to 3 in the polarized light filter 225. With such a configuration that differentiating the long side direction of metal wire, the ambient light can be cut effectively for the entire area of the raindrop detection image area 214 prepared from the captured image data.

Further, as for the optical filter 205, the rear-end filter 220 including the polarized-light filter 222 and the light-separation filter 223, segmented into areas as shown in FIG. 11, is disposed near the image sensor 206 compared to the front-end filter 210. Further, the front-end filter 210 can be disposed near the image sensor 206 compared to the rear-end filter 220.

(Optical Filter: Second Example Configuration)

Figure 20:
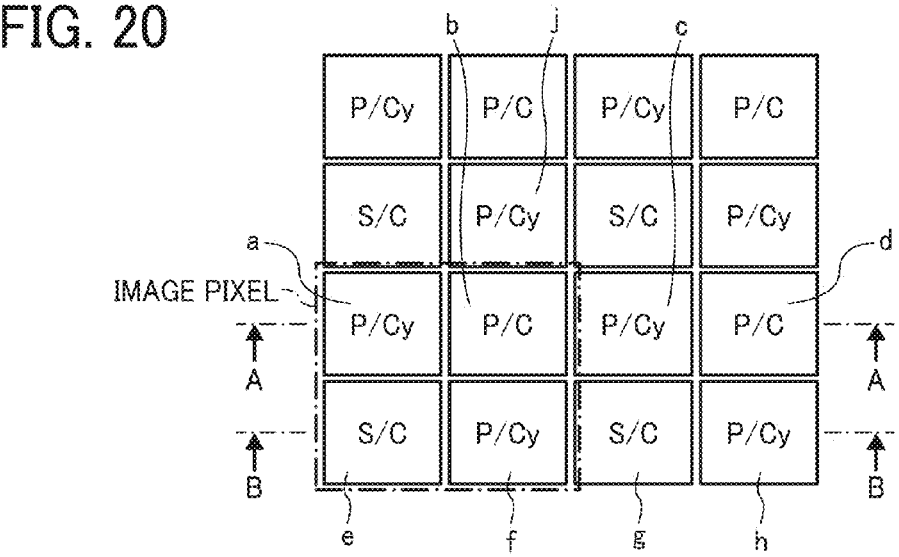
FIG. 20 shows an example pixel configuration of the optical filter of a second example configuration, in which light passes the optical filter and then received by each photodiode on the image sensor, and information corresponding to the received light or information of each image capture pixel is shown.
Figure 21:
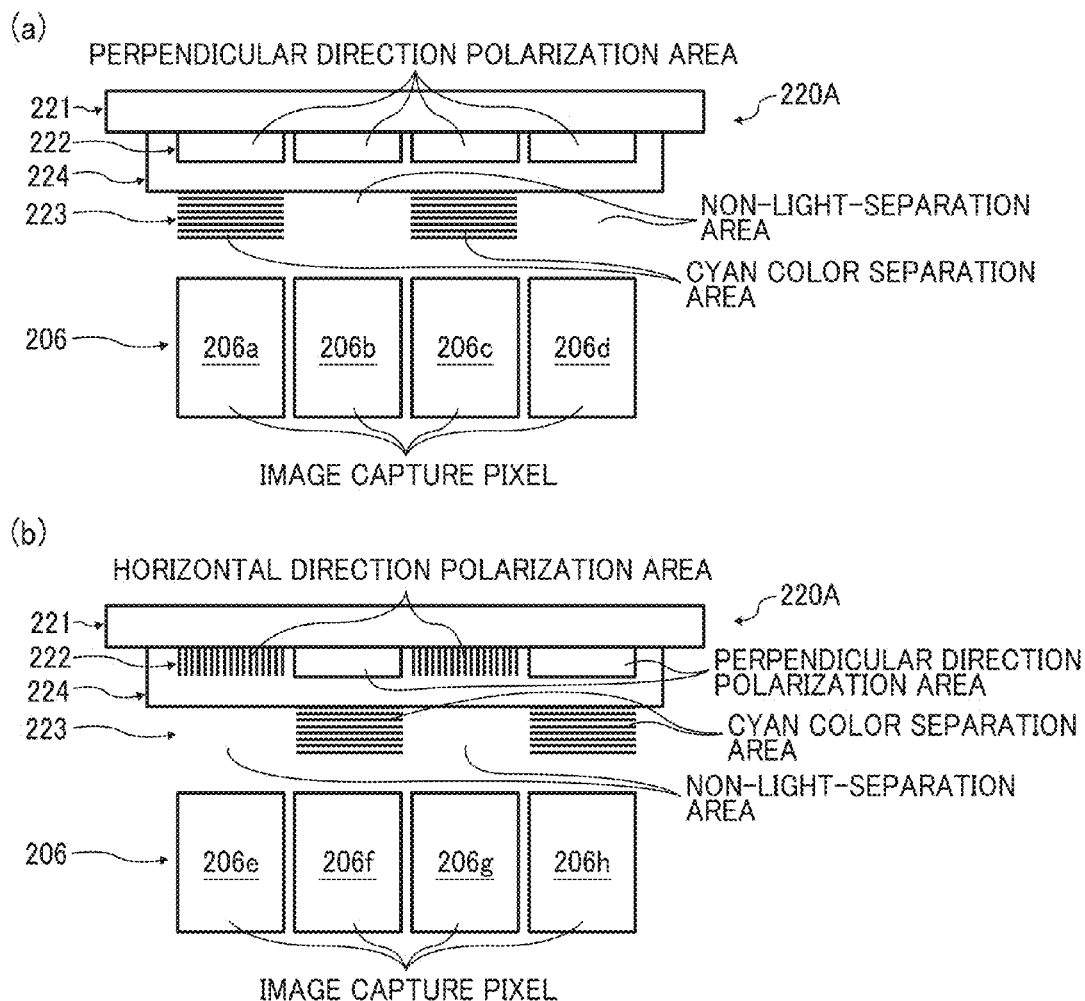
FIG. 21(a) shows a schematic cross-sectional view of the optical filter and the image sensor cut at a line A-A shown in FIG. 20.
FIG. 21(b) shows a schematic cross-sectional view of the optical filter and the image sensor cut at a line B-B shown in FIG. 20.

A description is given of a second example configuration of the optical filter 205 with reference to FIGS. 20 and 21. As for the optical filter 205 of the second example configuration, the front-end filter 210, and the raindrop detection filter 220B of the rear-end filter 220 are same as the first example configuration, and thereby the explanation of same parts is omitted, but the vehicle detection filter 220A of the rear-end filter 220 is described.

FIG. 20 shows an example pixel configuration of the optical filter 205 of the second example configuration, in which light passes the optical filter 205 and then received by each photodiode 206A on the image sensor 206, and information corresponding to the received light or information of each image capture pixel is shown. FIG. 21(a) shows a schematic cross-sectional view of the optical filter 205 and the image sensor 206 cut at a line A-A shown in FIG. 20. FIG. 21(b) shows a schematic cross-sectional view of the optical filter 205 and the image sensor 206 cut at a line B-B shown in FIG. 20.

In the first example configuration, the first area of the light-separation filter 223 corresponds to the red color separation area that selects and passes only the light having the red color wavelength band.

In the second example configuration, the first area of the light-separation filter 223 corresponds to a cyan light separation area that selects and passes only a light having cyan color wavelength band (Cy in FIG. 20). The cyan color wavelength band is included in wavelength band of the light that can pass through the polarized-light filter 222. Other configurations are same or similar as the first example configuration.

In the second example configuration, following images can be obtained: based on output signals of the image capture pixel "a" and the image capture pixel "f," the perpendicular polarized light image of cyan light for one-image pixel can be obtained; based on output signals of the image capture pixel "b," the perpendicular polarized light image of non-separated light for one-image pixel can be obtained; and based on output signals of the image capture pixel "e," the horizontal polarized light image of non-separated light for one-image pixel can be obtained.

Therefore, in the second example configuration, three types of captured image data can be obtained by one-time image capturing operation, wherein three types of captured image data are the perpendicular polarized light image for the cyan light, the perpendicular polarized light image of non-separated light, and the horizontal polarized light image of non-separated light.

As similar to the first example configuration, in the second example configuration, the recognition performance of the target objects (e.g., tail lamp, headlight, and lane) can be enhanced using such obtained three types of captured image data.

Further, in the second example configuration, by comparing the perpendicular polarized light image for the cyan light and the perpendicular polarized light image of non-separated light as comparing images, the recognition of the tail lamp can be conducted with high precision. Specifically, when the light emitted from the tail lamp passes through the cyan light separation area, the corresponding image capture pixel receives light having a small light amount, whereas when light emitted from the tail lamp passes through the non-light-separation area, the corresponding image capture pixel receives light having a greater light amount. Therefore, by comparing the perpendicular polarized light image for the cyan light and the perpendicular polarized light image of non-separated light, the difference of received light amount of the perpendicular polarized light image for the cyan light and the perpendicular polarized light image of non-separated light can be determined. Based on such difference, the contrast between the tail lamp and its background or surrounding area can be set high, by which the recognition performance of the tail lamp can be enhanced.

Further, in the first example configuration, the red color separation area and the red-color filter is used. In the second example configuration, the cyan light separation area using a cyan-color filter to pass through only cyan light is used. Compared to the first example configuration, in the second example configuration, the recognition performance of the tail lamp and the headlight of the oncoming vehicle can be set high when the front-running vehicle is close to the vehicle 100.

In the first example configuration, the red color separation area is used. If the tail lamp of the front-running vehicle comes to a position close to the vehicle 100, the light coming from the tail lamp is received via the red color separation area, and the received light amount becomes too great so that responsiveness may be saturated. As a result, the recognition performance of the tail lamp of the front-running vehicle, which is close to the vehicle 100, may deteriorate.

In contrast, in the second example configuration, the cyan light separation area is used. When the tail lamp of the front-running vehicle comes to a position close to the vehicle 100, the light coming from the tail lamp is received via the cyan light separation area while the responsiveness may not be saturated by the received light amount. Therefore, the deterioration of recognition performance for the tail lamp of the front-running vehicle close to the vehicle 100 can be reduced, suppressed, or prevented.

(Optical Filter: Third Example Configuration)

Figure 22:
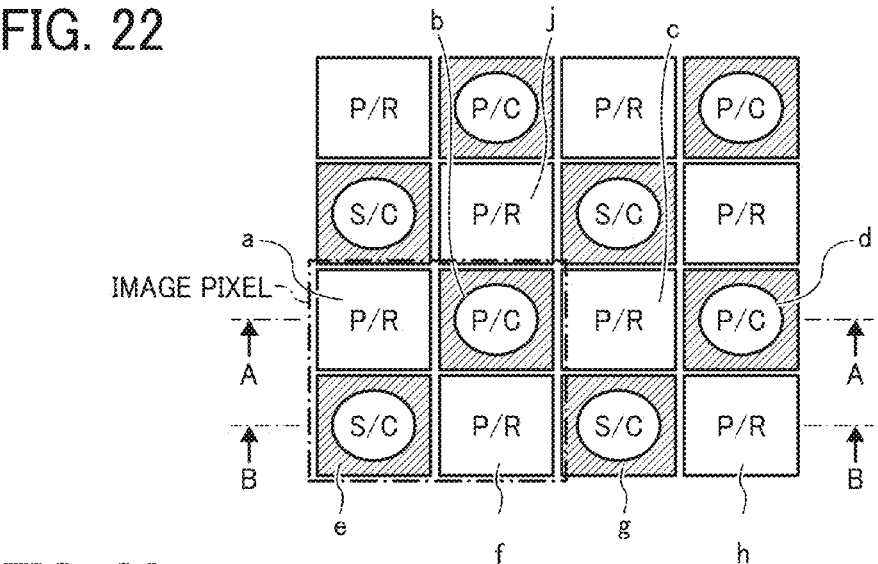
FIG. 22 shows an example pixel configuration of the optical filter of a third example configuration, in which light passes the optical filter and then received by each photodiode on the image sensor, and information corresponding to the received light or information of each image capture pixel is shown.
Figure 23:
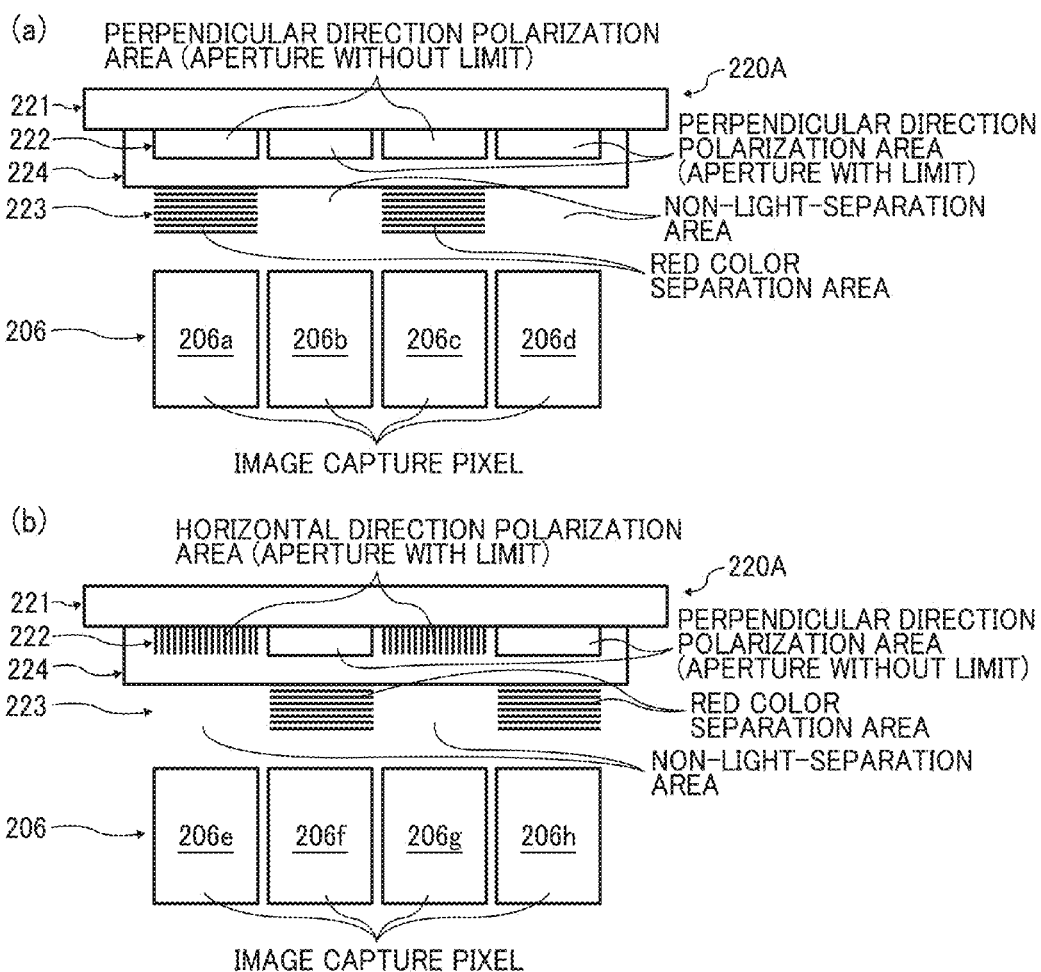
FIG. 23(a) shows a schematic cross-sectional view of the optical filter and the image sensor cut at a line A-A shown in FIG. 22.
FIG. 23(b) shows a schematic cross-sectional view of the optical filter and the image sensor cut at a line B-B shown in FIG. 22.

A description is given of a third example configuration of the optical filter 205 with reference to FIGS. 22 and 23. FIG. 22 shows an example pixel configuration of the optical filter 205 of the third example configuration, in which light passes the optical filter 205 and then received by each photodiode 206A on the image sensor 206, and information corresponding to the received light or information of each image capture pixel is shown. FIG. 23(*a*) shows a schematic cross-sectional view of the optical filter 205 and the image sensor 206 cut at a line A-A shown in FIG. 22. FIG. 23(*b*) shows a schematic cross-sectional view of the optical filter 205 and the image sensor 206 cut at a line B-B shown in FIG. 22.

In the third example configuration, the area segmentation of the polarized-light filter 222 and the light-separation filter 223 of the third example configuration is same as the first example configuration.

In the third example configuration, an aperture, which limits opening, is set for the corresponding non-light-separation area of the light-separation filter 223 so that the received light amount by the image sensor 206 can be restricted or limited. Therefore, as similar to the first example configuration, in the third example configuration, three types of captured image data can be obtained by one-time image capturing operation, wherein the three types of captured image data are the perpendicular polarized light image of red-color light, the perpendicular polarized light image of non-separated light, and the horizontal polarized light image of non-separated light. Among such three types of captured image data, the perpendicular polarized light image of non-separated light and the horizontal polarized light image of non-separated light of the third example configuration can be generated from the received light amount, which is smaller than the received light amount of the first example configuration.

Light that can pass through the non-light-separation area of the light-separation filter 223 can be restricted or limited by employing the following configuration, in which the light amount received by the image sensor 206 can be resultantly restricted or limited.

FIG. 24 shows one example of aperture for restricting or limiting light amount of light, passing a non-light-separation area of a light separation filter of the optical filter 205. As shown in FIG. 24, at the center portion of the image capture pixel, a wire grid structure defined by a circular peripheral is formed for the polarized-light filter 222, and the surrounding portion of the wire grid structure is formed as a light-shielding area using, for example, a solid film of aluminum, wherein the polarized-light filter 222 is corresponded to the non-light-separation area of the light-separation filter 223. In such configuration, the solid film of aluminum blocks the light.

By setting a given size for the aperture (i.e., aperture ratio) used for the wire grid structure (e.g., large to small), the light amount that can pass through the non-light-separation area of the light-separation filter 223 can be restricted or limited variably, and the light amount received by the image sensor 206 can be resultantly restricted or limited variably.

Further, the shape of aperture for the wire grid structure is not restricted or limited to the circle shape (FIG. 24), but for example, a square or square-like shape (FIG. 25) can be used as the aperture. As shown in FIG. 25, the corner of square-like shape can be rounded by setting a given R so that the square-like shape can be formed with higher precision by the etching process.

The polarized-light filter 222 having the wire grid structure can be formed, for example, as follows. An aluminum film is formed uniformly or evenly over the translucent filter board 221, and then the aluminum film is partially removed by the etching process, by which the wire grid structure is obtained.

In the third example configuration, the light-shield area (or light blocking area) made of aluminum is disposed on the surrounding portion of the wire grid structure to limit the aperture. Specifically, the wire grid structure is formed while retaining the aluminum film on the surrounding portion of the wire grid structure, by which the aperture that limits an opening can be formed. Therefore, such process can be conducted simply compared to a process of preparing the polarized-light filter 222 and separately preparing an opening limiting member such as an aperture member, and combining the polarized-light filter 222 and the opening limiting member.

A description is given of preparing the polarized-light filter 222 and separately preparing an opening limiting member such as an aperture member with reference to FIGS. 26, 27, 28, and 29.

FIG. 26 shows one example of an opening limiting layer, in which the opening limiting layer has an aperture or opening at its center portion, corresponding to the center portion of image capture pixel, to pass through the light. As shown in FIG. 26, the opening limiting layer does not include the wire grid structure.

Further, the light-shield area (or light blocking area) for limiting the opening portion may not limited to a reflection film such as aluminum film or the like. For example, a light absorbing film can be used as the light-shield area. For example, as shown in FIG. 27, a solid film of black resist material can be used for forming the light-shield area. In such a case, the shape of aperture (or opening portion) is not limited a circle shape (FIG. 27), but, for example, a square or square-like shape (FIG. 28) can be used. In FIG. 28, the corner of square-like shape may not be rounded, but the corner of square-like shape may be rounded by setting a given R so that the square-like shape can be formed with higher precision by the etching process.

Further, the numbers of aperture for passing through the light for one image capture pixel is not limited to any specific numbers. For example, one aperture is set for one image capture pixel, and a plurality of apertures can be set for one image capture pixel (i.e., a plurality of wire grid structure areas).

Further, the numbers of the light-shield area for one image capture pixel is not limited to any specific numbers. For example, one light-shield area is set for one image capture pixel, and a plurality of light-shield areas can be set for one image capture pixel. Further, the position of the light-shield area is not limited to the surrounding portion of the image capture pixel. For example, as shown in FIG. 29, a plurality of light-shield areas such as aluminum solid film areas can be disposed on the wire grid structure with a given arrangement pattern such as a dispersed pattern.

In the third example configuration, three types of captured image data can be obtained, wherein the three types of captured image data are the perpendicular polarized light image of red-color light with the same received light amount of the first example configuration, whereas the received light amount of the perpendicular polarized light image of non-separated light, and the horizontal polarized light image are restricted or limited (e.g., smaller) compared to the first example configuration.

In the third example configuration, the tail lamp can be recognized by using the perpendicular polarized light image of red-color light to detect the front-running vehicle, and the headlight of the oncoming vehicle can be recognized by using the perpendicular polarized light image of non-separated light and the horizontal polarized light image of non-separated light to detect the oncoming vehicle.

Typically, each of the tail lamp and the headlight is configured by two lamps or lights disposed in the horizontal direction by setting a given distance between the two lamps or lights. As such, one set of tail lamp is configured of two lamps, and one set of headlight is configured of two lights.

Detection of the front-running vehicle and the oncoming vehicle can use such configuration of the lamps and lights. Specifically, if the images of two tail lamps are recognized in the captured image with a given distance, such one set of tail lamps can be recognized as the tail lamps of the front-running vehicle, and if the images of two headlights are recognized in the captured image with a given distance, such one set of headlight can be recognized as the headlight of the oncoming vehicle.

Typically, the light intensity of the headlight is greater than the light intensity of the tail lamp. If the responsiveness is set at a level to effectively or suitably receive the light coming from the tail lamp, the light amount received from the headlight may saturate such responsiveness. If the responsiveness or light intensity level is saturated, the two headlight image areas may be recognized as one headlight image area, in which the two headlight image areas, which should be recognized as separate image areas, may be recognized one headlight image area. As a result, the headlight image areas cannot be effectively recognized, by which the recognition performance of the oncoming vehicle deteriorates.

Further, in contrast, if the responsiveness is set at a level to effectively or suitably receive the light coming from the headlight, the light amount received from the tail lamp may be too small to be detected by the responsiveness, by which the tail lamp image area cannot be recognized effectively. As a result, the recognition performance of the front-running vehicle deteriorates.

In the third example configuration, the light amount of the perpendicular polarized light image of non-separated light, and the light amount of the horizontal polarized light image of non-separated light received by the image sensor 206 for recognizing the headlight of the oncoming vehicle is restricted or limited by the above described opening limiting member such as an aperture.

Therefore, if the responsiveness is set at level matched to the light intensity of tail lamp, which is recognized by using the perpendicular polarized light image of red-color light that has no restriction or limitation of receiving light, the responsiveness may not be saturated even when the image sensor 206 receives the light amount of the headlight of the oncoming vehicle, by which each of the two headlight image areas can be recognized separately. As a result, deterioration of the recognition performance of the oncoming vehicle can be reduced, suppressed, or prevented.

Further, in another configuration, headlight image and tail lamp image can be separately captured by switching the responsiveness for the headlight and the responsiveness for the tail lamp. Based on the separately captured image, the recognition of the headlight and the recognition of the tail lamp can be conducted, by which both of the recognition of the headlight and the recognition of the tail lamp can be conducted effectively. In such configuration, a control system to switch the responsiveness is required, and the frame rate of the captured image data becomes one half. In the third example configuration, both of the recognition of the headlight and the recognition of the tail lamp can be conducted without such control system and frame rate conditioning.

(Optical Filter: Fourth Example Configuration)

A description is given of a fourth example configuration of the optical filter 205. As above described, the polarized-light filter 222 of the rear-end filter 220 of the optical filter 205 is segmented into areas for corresponding image capture pixel, in which one type of segmented area corresponds to the perpendicular direction polarization light area (i.e., first area) to select and pass through only the perpendicular polarized light component P, and another type of segmented area corresponds to the horizontal direction polarization light area (i.e., second area) to select and pass through only the horizontal polarized light component S.

With such a configuration, based on the image data prepared from the light received by an image capture pixel, which receives the light that has passed through the perpendicular direction polarization light area, the perpendicular polarized light image having cut the horizontal polarized light component S can be obtained.

Further, based on the image data prepared from the light received by an image capture pixel, which receives the light that has passed through the horizontal direction polarization light area, the horizontal polarized light image having cut the perpendicular polarized light component P can be obtained.

If the windshield 105 is a flat face, by effectively setting the polarization light direction (i.e., transmission axis) of the perpendicular direction polarization light area and the horizontal direction polarization light area for the windshield 105, the perpendicular polarized light image and the horizontal polarized light image, which can effectively cut a ghost image projected on the windshield 105, can be obtained.

However, the windshield 105 disposed for an automobile is not only slanted toward the forward direction, but also greatly warped toward the rearward direction along the left/right direction from the center portion to the both side end portions of the automobile to enhance aerodynamic characteristics of the automobile. If the polarization light direction (i.e., transmission axis) of the perpendicular direction polarization light area and the horizontal direction polarization light area for the polarized-light filter 222 of the optical filter 205 is set at the same value at any pixel positions, a ghost image projected at the center of the windshield 105 may be effectively cut from at the center of the captured image, but a ghost image projected at the end of windshield 105 may not be effectively cut from at the end of the captured image.

Figure 30:
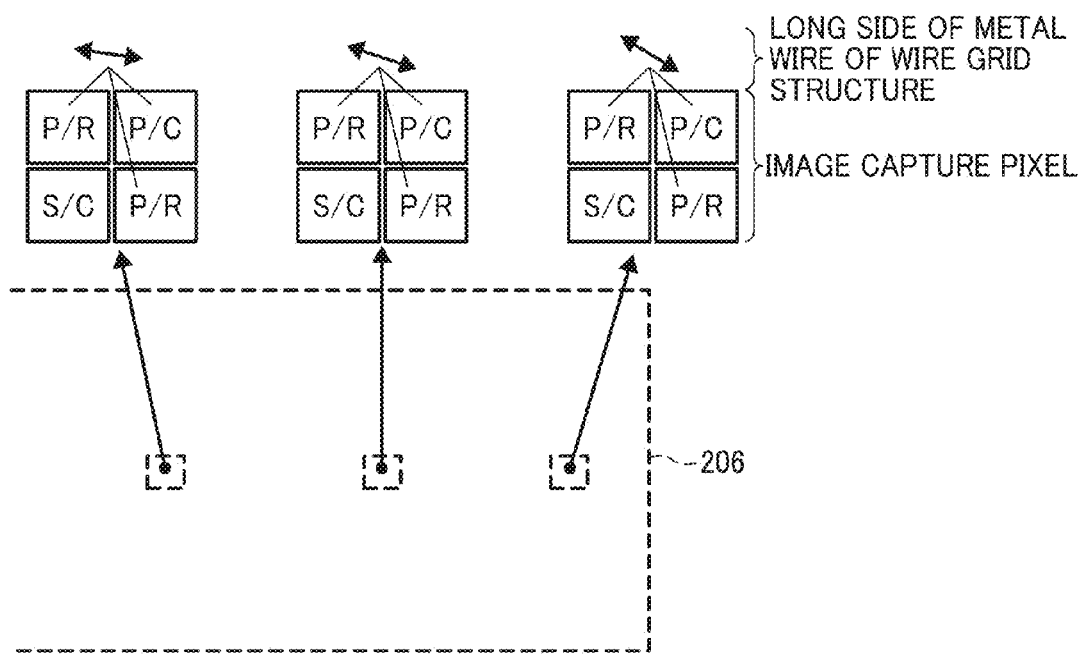
FIG. 30 shows a long side direction of metal wire of a wire grid structure of a polarized-light filter of an optical filter of a fourth example configuration.

FIG. 30 shows the long side direction of metal wire of the wire grid structure of the polarized-light filter 222 of the optical filter 205 of the fourth example configuration. The area segmentation of the polarized-light filter 222 and the light-separation filter 223 of the fourth example configuration is same as the first example configuration.

However, in the fourth example configuration, the polarization light direction (i.e., transmission axis) of the perpendicular direction polarization light area of the polarized-light filter 222 is not uniform among image capture pixels. Specifically, as shown in FIG. 30, the perpendicular direction polarization light area of the polarized-light filter 222 can be formed in view of the warping level of the windshield 105. For example, as closer to the end portion in the horizontal direction of the polarized-light filter 222, the greater angle is set between the polarization light direction (i.e., transmission axis) of the perpendicular direction polarization light area of the polarized-light filter 222 and the perpendicular direction.

As such, in the polarized-light filter 222 of the fourth example configuration, as closer to the end portion in the horizontal direction of the polarized-light filter 222, an angle between the long side direction of metal wire of the wire grid structure for the perpendicular direction polarization light area and the horizontal direction is set greater. In example embodiment, because the wire grid structure can be used for forming the perpendicular direction polarization light area, a number of areas having different polarization light directions at tiny scale level such as image capture pixel can be formed.

A description is given of details of the rear-end filter 220 of the optical filter 205. The translucent filter board 221 is made of translucent materials such as glass, sapphire, rock crystal, which can pass through light for use such as visible light range and infra-red light. Such glass having high durability with reasonable cost, may be vitreous silica, silica glass, quartz glass, fused silica (refractive index of 1.46), heat resistant glass (refractive index of 1.51), or the like.

Figure 31:
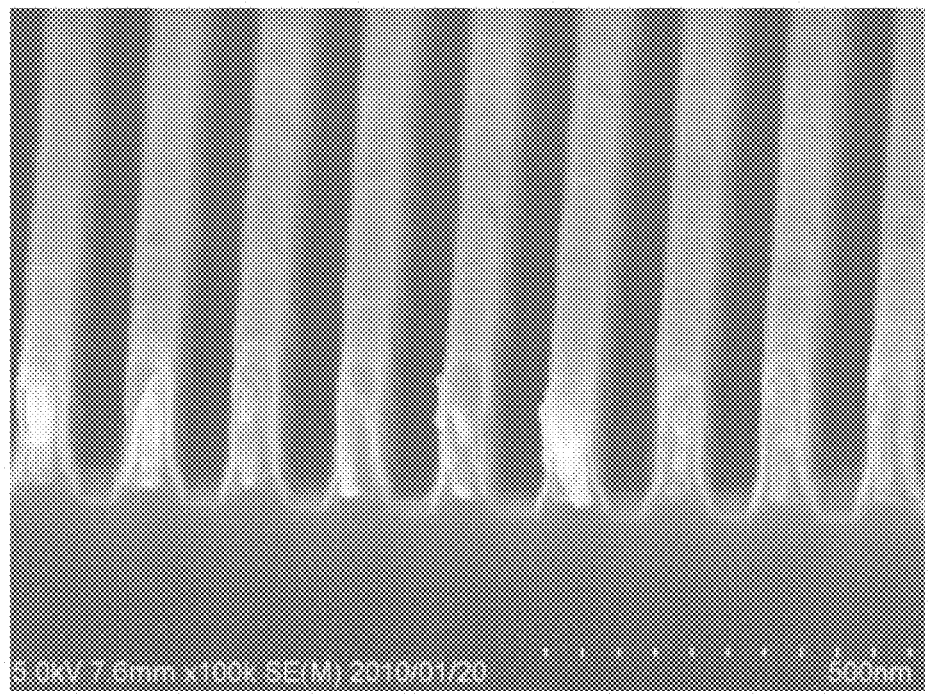
FIG. 31 is an enlarged photo of a wire grid structure used for a polarization filter.

The polarized-light filter 222 formed on the translucent filter board 221 may be a polarizer having a wire grid structure, for example, shown in FIG. 31. The wire grid structure is formed by disposing a number of conductive metal wires with a given wire pitch in a given direction. For example, a number of the aluminum wires can be arranged with a given wire pitch in a given direction.

By setting the wire pitch of the wire grid structure enough smaller than a wavelength band of the incidence light such as one half (½) or less of wavelength, an electric field vector of light oscillating in parallel to the long side direction of metal wire can be mostly reflected, and electric field vector of light oscillating in perpendicular to the long side direction of metal wire can be mostly passed through, by which a polarizer that can generate single polarization light can be produced.

Typically, as for the polarizer having the wire grid structure, when the cross sectional area of the metal wire increases, the extinction ratio increases, and further if the metal wire has a greater width with respect to a pitch width, the transmittance ratio decreases. Further, if the cross sectional shape perpendicular to the long side direction of metal wire is a taper shape, the wavelength dispersing phenomenon for the transmittance ratio and the polarization level become small for broader wavelength range, and thereby a high extinction ratio may be set.

The polarized-light filter 222 employing the wire grid structure has following features. The wire grid structure can be formed using known semiconductor manufacturing process. Specifically, a thin film of aluminum is deposited on the translucent filter board 221, and then the patterning is conducted, and the sub-wavelength convex/concave structure of the wire grid is formed by the metal etching. By using such manufacturing process, the long side direction of metal wire, that is polarization light direction (i.e., polarization axis), can be adjusted with a size of image capture pixel of the image sensor 206 such as several μm level.

Therefore, the polarized-light filter 222, setting different long side directions of metal wires, that is polarization light direction (i.e., polarization axis), for each image capture pixel, can be formed. Further, the wire grid structure can be formed of metal materials such as aluminum having good level of heat-resistance. Such wire grid structure can be preferably used under high temperature environment which may frequently occur inside vehicles or the like.

The filler agent 224, used for forming a flat face over the polarized-light filter 222, is filled into the concave portions between the metal wires forming the polarized-light filter 222, and further, the filler agent 224 is deposited over the multiple layers of the metal wires forming the polarized-light filter 222. The filler agent 224 may be preferably inorganic materials having a refractive index same or smaller than a refractive index of the translucent filter board 221.

Materials used for the filler agent 224 preferably has a low refractive index as close as the refractive index of "1" of air to prevent degradation of polarization property of the polarized-light filter 222. For example, porous ceramic materials having tiny holes dispersed in ceramics may be preferably used. Specifically, porous silica ($SiO_2$), porous magnesium fluoride (MgF), or porous alumina ($Al_2O_3$) can be used. The refractive index can be set based on the numbers and size (i.e., porous level) of holes in ceramics. If the main component of the translucent filter board 221 is rock crystal or glass of silica, porous silica (n=1.22 to 1.26) can be preferably used.

The filler agent 224 can be applied using the spin on glass (SOG). Specifically, a solution prepared by solving silanol ($Si(OH)_4$) into alcohol is applied on or over the polarized-light filter 222 formed on the translucent filter board 221 using the spin coating method. Then, the solvent is evaporated by applying heat, and the silanol is reacted under the dehydrogenative polymerization reaction process.

The polarized-light filter 222 employs the wire grid structure having a sub-wavelength size having a weak mechanical strength, which may be damaged by a small external force. Because the optical filter 205 is desired to be contact the image sensor 206 with a close-contact arrangement, the optical filter 205 and the image sensor 206 may contact with each other during the manufacturing process.

In the example embodiment, because at a top of multiple layers of the polarized-light filter 222, facing the image sensor 206, is deposited by the filler agent 224, even when the optical filter 205 contacts the image sensor 206, damages to the wire grid structure can be reduced, suppressed, or prevented. Further, because the filler agent 224 can be filled into the concave portions set between the metal wires of the wire grid structure of the polarized-light filter 222, an intrusion of foreign particles to the concave portions can be prevented.

Further, in the example embodiment, a protection layer formable by the filler agent 224 is not disposed on or over the light-separation filter 223 stacked on the filler agent 224. Based on the experiment by the inventors, it was found that damages affecting the captured image did not occur even when the light-separation filter 223 contacted the image sensor 206. Therefore, the protection layer can be omitted in view of cost reduction.

Further, the height of the metal wire (or convex portion) of the polarized-light filter 222 is low such as one half or less of the wavelength for use, whereas the height of filter layer (convex portion) of the light-separation filter 223 for forming the red color separation area or cyan light separation area is high such as same or several times of the wavelength for use.

The greater the thickness of the filler agent 224, the harder it is to secure the flatness of the top face of the filler agent 224. Because the flatness level of the filler agent 224 affects property of the optical filter 205, there is an upper limit of the thickness of the filler agent 224. Therefore, in the example embodiment, the light-separation filter 223 is not covered by the filler agent 224.

As for the light-separation filter 223, the filter layer, formed for the red color separation area or cyan light separation area, employs a multi-layered film structure, in which thin films having high refractive index and thin films having low refractive index are stacked one to another for multiple times.

Such multi-layered film structure can set the spectrum transmittance ratio of light with a broader range using light interference. Further, by stacking the thin films for multiple times, the reflection ratio of a light having a specific wavelength (e.g., wavelength band other than red color) can be set almost 100%.

Figure 32:
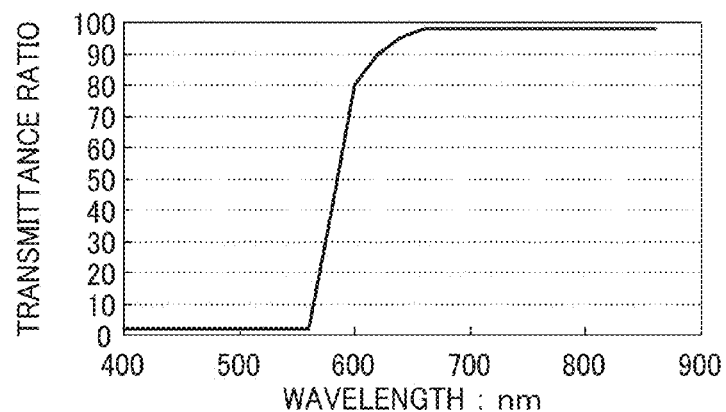
FIG. 32 is an example profile of filter property of a cut-filter applicable for a light separation filter.

In the example embodiment, because the wavelength range for use for the captured image data is the wavelength band of substantially visible light such as wavelength band for visible light and infra-red light, the image sensor 206 having sensitivity for the concerned wavelength band for use is selected, and a cut-filter for cutting specific wavelength (see FIG. 32) can be formed. For example, a cut-filter employs the multi-layered film structure that can transmit light having wavelength 600 nm or more and reflect light having wavelength less than 600 nm as shown in FIG. 32.

Such cut-filter can be obtained by forming a multi-layered film structure such as "substrate/(0.125L 0.25H 0.125L)p/medium A" stacked from the bottom layer to the top layer of the optical filter 205. The substrate means the above described filler agent 224. Further, "0.125L" is indication of film thickness for low refractive index material (e.g., $SiO_2$), and nd/λ is set as 1L. Therefore, "0.125L" film means a film of low refractive index material having a film thickness that the optical path length becomes one eighth (⅛) of wavelength. Further, "n" means the refractive index, "d" means thickness, "λ" means cut-off wavelength. Similarly, "0.25H" is indication of film thickness for high refractive index material (e.g., $TiO_2$), and nd/λ is set as 1H. Therefore, "0.25H" film means a film of high refractive index material having a film thickness that the optical path length becomes one fourth (¼) of wavelength. Further, "p" means the numbers of stacking of films indicated in the parenthesis. The greater the "p," the effect such as ripple can be reduced, suppressed, or prevented. Further, the medium A means air, or resin and bonding agent for close contact with the image sensor 206.

Figure 33:
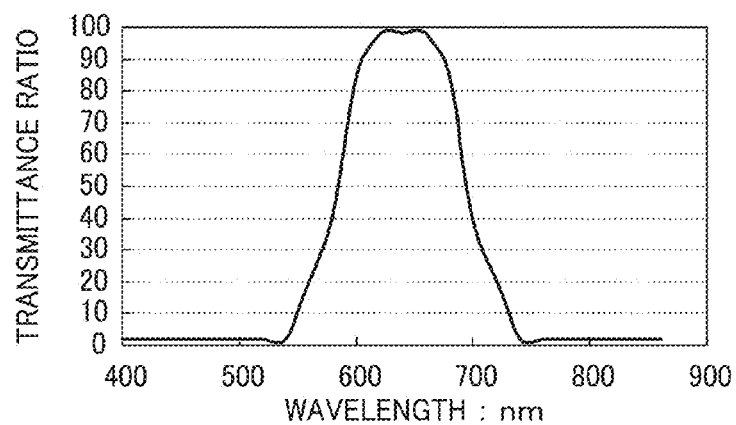
FIG. 33 is an example profile of filter property of a bandpass filter applicable for a light separation filter.

Further, the filter layer of the light-separation filter 223 for forming the red color separation area or cyan light separation area may be a band-pass filter having filter property such as transmittance wavelength range from 600 nm to 700 nm as shown in FIG. 33. Such band-pass filter can separately recognize the light in the red color, and the infra-red light having a wavelength greater that the visible red color. Such band-pass filter can be obtained, for example, by preparing a multi-layered film structure such as "substrate/(0.125L 0.5M 0.125L)P(0.125L 0.5H 0.125L)$_q$(0.125L 0.5M 0.125L)r/medium A". Further, as above described, by using titanium dioxide ($TiO_2$) as high refractive index material, and silicon dioxide($SiO_2$) as low refractive index material, the light-separation filter 223 having high weather resistance can be devised.

A description is given of one example of a preparation process of the light-separation filter 223. At first, the above described multi-layered film is formed on a layer of the filler agent 224, formed on the translucent filter board 221 and the polarized-light filter 222. Such multi-layered film can be formed using the known deposition methods. Then, the multi-layered film corresponding to the non-light-separation area is removed by using the known lift-off process. As for the lift-off process, an inverted pattern (or negative pattern) of target pattern is formed on the layer of the filler agent 224 using metal or photo resist in advance, and then the multi-layered film is formed thereon. Then, the multi-layered film corresponding to the non-light-separation area is removed with the concerned metal and/or photo resist.

In the example embodiment, the light-separation filter 223 employs the multi-layered film structure, which can set spectral characteristics with higher degree of freedom. Color filters used for typical color sensors can be formed using a resist agent, but such resist agent is difficult to control spectral characteristics compared to the multi-layered film structure. In the example embodiment, because the light-separation filter 223 employs the multi-layered film structure, the light-separation filter 223 suitable for the wavelength of the tail lamp light can be formed easily.

(Light Control of Headlight)

A description is given of the light control of headlight for the example embodiment. As for the light control of headlight, the captured image data captured by the image capture device 200 is analyzed to recognize the tail lamp and/or the headlight of vehicles, in which the front-running vehicle is detected from the recognized tail lamp, and the oncoming vehicle is detected from the recognized headlight.

Then, for example, a switching control of high beam/low beam of the headlight 104 is conducted, and a light-dimming control is partially conducted for the headlight 104 to prevent a projection of strong light of the headlight of the vehicle 100 to the eyes of drivers of the front-running vehicle and the oncoming vehicle, by which drivers of other vehicles are not dazzled by the headlight of the vehicle 100 while providing the enough field of view for the driver of vehicle 100. In the followings, the rear-end filter 220 of the optical filter 205 of the first example configuration is used as one example of the optical filter 205.

The light control of headlight of the vehicle 100 can be conducted using information obtained from the image capturing unit 101. Such information may be intensity of light coming form each point such as light emitting object/light reflecting object present in the image capturing area (brightness information); distance between other vehicles having the light emitting object/light reflecting object such as the headlight and the tail lamp and the vehicle 100 (distance information); spectrum information obtained by comparing red color light component and white light component (i.e., non-separated light) coming form each of light emitting object/light reflecting object; polarized light information obtained by comparing the horizontal polarized light component and the perpendicular polarized light component of white light; perpendicular polarized light information of white light having cut the horizontal polarized light component; and the perpendicular polarized light component information of red color having cut the horizontal polarized light component.

The brightness information can be used as follows. In the night time, if the front-running vehicle and the oncoming vehicle are present at the same distance from the detector-equipped vehicle such as the vehicle 100, the image capture device 200 captures the front-running vehicle and the oncoming vehicle. In such a case, the headlight of the oncoming vehicle, one of the detection-target objects, is recognized as the brightest image in the captured image data, and the tail lamp of the front-running vehicle, another one of the detection-target objects, is recognized as an image, which is darker than the image of the headlight of the oncoming vehicle.

Further, the image of the reflector can be recognized as an image in the captured image data. Because the reflector itself does not emit light, but only reflects light coming from the headlight of the vehicle 100, the image of the reflector in the captured image data becomes darker than the image of the tail lamp of the front-running vehicle.

Further, the headlight of the oncoming vehicle, the image of the light coming from the tail lamp of the front-running vehicle, and the image of the light coming from the reflector received by the image sensor 206 becomes darker gradually as the distance between the vehicles longer. Therefore, by using the brightness information (or light intensity information) obtained from the captured image data, the detection-target objects such as headlight and tail lamp, and the reflector can be recognized effectively.

Further, distance information can be used as follows. Typically, the headlight and the tail lamp include a pair of lamps or lights disposed at a right position and a left position of one vehicle. Such configuration can be used to compute the distance between the headlight and/or the tail lamp of other vehicles and the detector-equipped vehicle such as the vehicle 100.

In the captured image data captured by the image capture device 20, images of the pair of lamps are observed at right and left in the captured image data. Such two images may be present at a close proximity position with each other and at the same height position. Further, a lamp image area of right and left lamps has the almost same size, and a shape of the lamp image area for right and left lamps is the almost same. Therefore, such features can be used as conditions to determine whether the captured image data includes images of pair of lamps (pair lamps). For example, if the lamp image areas satisfying such conditions can be determined as the pair-lamps. Further, the greater the distance, the left and right lamps of the pair-lamps cannot be recognized separately, but may be recognized as a single lamp.

When the pair-lamps can be recognized as such, the distance to the pair-lamps such as the headlight and the tail lamp can be computed.

Distance between the left and right lights of the headlight and distance between the left and right lamps of the tail lamp can be set to a constant value w0 (e.g., 1.5 m). The focus distance f of the capture lens 204 of the image capture device 200 is known. Distance w1 between two lamp image areas on the captured image data, corresponding the left and right lamps/lights, captured by the image sensor 206 of the image capture device 200 can be computed. Then, distance X between the pair-lamps such as the headlight and the tail lamp, and the vehicle 100 can be computed as "X=f×w0/w1," which is a simple proportional calculation. If the computed distance X is within a suitable range, the two lamp image areas can be recognized as the headlight or the tail lamp of other vehicles. Therefore, by using such distance information, the recognition precision of the detection-target object (e.g., headlight, tail lamp) can be enhanced.

Further, spectrum information can be used as follows. Based on the captured image data captured by the image capture device 200, the image capture pixels such as "a, c, f, h" of the image sensor 206 (see FIG. 14) receive the perpendicular polarized light component of red color light (P/R), and only the pixel data of (P/R) are extracted to generate a red color image using only red color component present in the image capturing area. Therefore, if an image area of red color image has a light intensity greater than a given level of light intensity, such image area can be recognized as the tail lamp image area, corresponding to the tail lamp.

Further, based on the image data captured by the image capture device 200, the image capture pixels such as "b, d" of the image sensor 206 (see FIG. 14) receive the perpendicular polarized light component of white light such as non-separated light (P/C), and only the pixel data of (P/C) are extracted to generate a perpendicular polarized light component of a monochrome luminance image present in the image capturing area. Therefore, an image area of the red color image, and an image area of the monochrome luminance image can be compared by computing an intensity ratio such as red color intensity ratio between such image areas.

Based on the red color intensity ratio, the relative ratio of the red color component in the light coming from an object such as light emitting object/light reflecting object, present in the image capturing area, can be computed. The red color intensity ratio of the tail lamp can be high compared to the light coming from the headlight, or the light coming from other light emitting object/light reflecting object. Therefore, the recognition precision of the tail lamp can be enhanced by using the red color intensity ratio.

Further, the polarized light information can be used as follows. Based on the image data captured by the image capture device 200, the image capture pixels such as "b, d" of the image sensor 206 (see FIG. 14) receive the perpendicular polarized light component of white light (i.e., non-separated light) (P/C), and the corresponding pixel data are extracted, and the image capture pixels such as "e, g" the image sensor 206 (see FIG. 14) receive the horizontal polarized light component of white light (i.e., non-separated light) (S/C), and the corresponding pixel data are extracted.

Then, for each one of image pixels, the perpendicular polarized light component of white light (P/C) and the horizontal polarized light component of white light (S/C) can be compared.

Based on comparison of pixel values or intensity of the perpendicular polarized light component and the horizontal polarized light component, the image data based on the comparison can be obtained. Specifically, for example, a difference of "S−P" between the perpendicular polarized light component P of white light such as non-separated light and the horizontal polarized light component S of white light such as non-separated light can be used as a difference of image or comparing images.

Based on such comparing images, the contrast between a direct light image area such as headlight image area and an indirect light image area such as reflection light image area can be set greater, by which the recognition precision of headlight can be enhanced. In the indirect light image area, the light of the headlight enters the image capture device 200 directly, whereas in the indirect light image area, the light of the headlight reflected at a water surface of wet road enters the image capture device 200.

The comparing images may be a ratio-based image (S/P) or an and a polarization-light-based image using the polarization index (S−P)/(S+P) obtained from a pixel value of the perpendicular polarized light component P of white light (i.e., non-separated light) and from a pixel value of the horizontal polarized light component S of white light (i.e., non-separated light).

In general, light reflected on a horizontal mirror surface such as water surface has the horizontal polarized light component having greater intensity. When the ratio (S/P) of the horizontal polarized light component S and the perpendicular polarized light component P or the polarization index (S−P)/(S+P) is computed, the ratio (S/P) or the polarization index (S−P)/(S+P) becomes greatest at a specific angle (Brewster's angle).

For example, when the road is wet, the asphalt face (or dispersing face) covered by water becomes a nearly mirror surface, by which the light of the headlight reflected from the road surface has the horizontal polarized light component S having greater intensity as dominant component.

Therefore, as for the indirect image area including the light of headlight reflected from the road surface, the ratio-based image or the polarization-light-based image has a greater value. In contrast, as for the direct image area including the light coming directly from the headlight (non-polarized light), the ratio-based image or the polarization-light-based image has a smaller value. Based on such difference, the light of the headlight (i.e., indirect light) reflected from the wet road surface, having the same level of the light amount of the direct light coming directly from the headlight, can be effectively removed, and thereby the direct light coming from headlight can be recognized separately from such reflection light of headlight (i.e., indirect light) reflected from the wet road surface.

Figure 34:
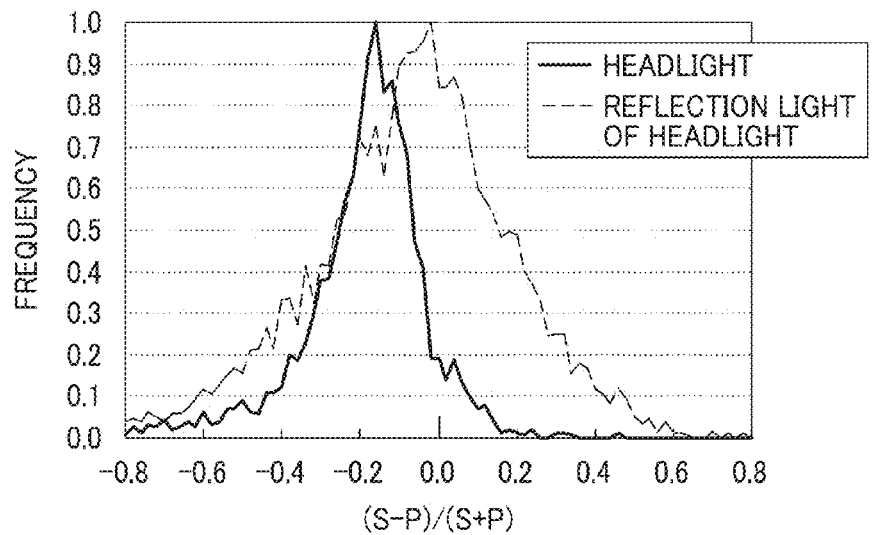
FIG. 34 shows a histogram of computed polarization index (S−P)/(S+P) of direct light coming from a headlight, and reflection light of headlight reflected from a wet road surface in rainy weather, wherein light images were captured by the image capture device.

FIG. 34 shows a histogram of computed polarization index (S−P)/(S+P) of the direct light coming directly from the headlight (solid line in FIG. 34), and the reflection light of headlight reflected from a wet road surface in rainy weather (dotted line in FIG. 34), wherein images were captured by the image capture device 200. The vertical axis of FIG. 34 indicates the frequency, which is normalized to one. The horizontal axis of FIG. 34 indicates the polarization index (S−P)/(S+P). Because the reflection light of the headlight, reflected from the wet road, has a greater horizontal polarized light component S compared to the direct light from the headlight, the profile of the reflection light is shifted to the right side of the profile of the headlight as shown in FIG. 34.

Figure 35:
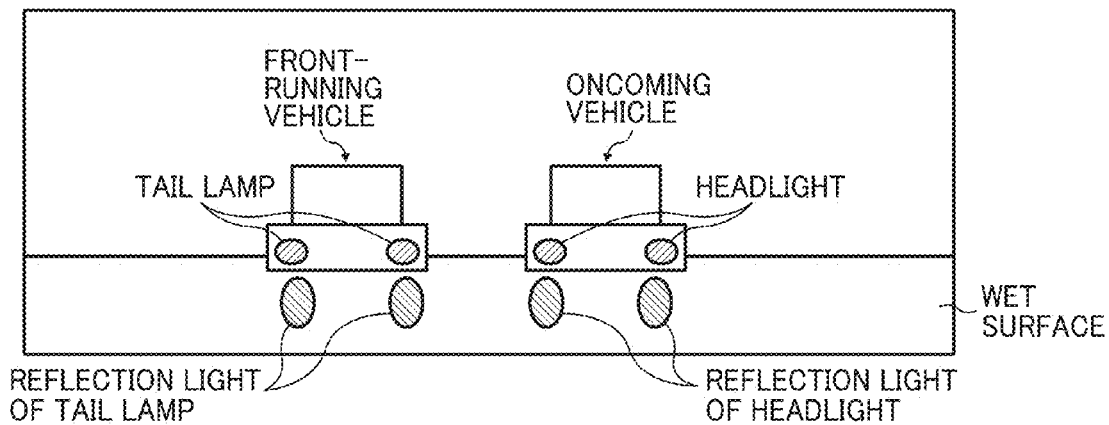
FIG. 35 shows a schematic image captured by an image capture device when a front-running vehicle and an oncoming vehicle are both present at approximately the same distance in a forward direction of the detector-equipped vehicle, wherein all vehicles are present on a wet road surface.

FIG. 35 shows a schematic image captured by the image capture device 200 when a front-running vehicle and an oncoming vehicle are both present at almost the same distance in a forward direction of the detector-equipped vehicle such as vehicle 100, wherein all vehicles are present on a wet road. In such a situation, it is difficult to separately detect the tail lamp of the front-running vehicle, the reflection light of tail lamp light reflected from the wet road surface (i.e., indirect light), the headlight of the oncoming vehicle, and the reflection light of headlight light reflected from the wet road surface (i.e., indirect light) using only the brightness information and distance information.

Even in such a situation, by using the above described spectrum information, the tail lamp of the front-running vehicle and the reflection light of tail lamp light reflected from the wet road surface (i.e., indirect light) can be separately recognized with high precision, and the headlight of the oncoming vehicle and the reflection light of headlight light reflected from the wet road surface (i.e., indirect light) can be separately recognized with high precision.

Specifically, in the lamp image area extracted by using the brightness information and distance information, if an image area is computed to have a value exceeding a given threshold value set for the above described pixel value or intensity of red color image, or having a value exceeding a given threshold value set for the above described red-color intensity ratio, the image area can be recognized as the tail lamp image area, capturing the tail lamp of the front-running vehicle or the reflection light of tail lamp light reflected from the wet road surface (i.e., indirect light); and if an image area is computed to have a value smaller than the concerned threshold value for the pixel value or intensity of red color image, the image area can be recognized as the headlight image area capturing the headlight of the oncoming vehicle, or the reflection light of headlight reflected from the wet road surface (i.e., indirect light).

In the example embodiment, by applying the above described polarized light information to each lamp image area recognized by using the spectrum information, the direct light from the tail lamp and/or headlight, and the reflection light from objects (i.e., indirect light) can be separately recognized with high precision.

Specifically, for example, as for the tail lamp, based on the pixel value or light intensity of the horizontal polarized light component S of red color image, or the polarization index (S−P)/(S+P) of red color image, the difference of the frequency and intensity of the horizontal polarized light component is computed, by which the direct light from the tail lamp of the front-running vehicle, and the reflection light of the tail lamp (i.e., indirect light) reflected from the wet road can be separately recognized.

Further, for example, as for the headlight, based on the pixel value or light intensity of the horizontal polarized light component S of white color image, or the polarization difference of white color image, or the polarization index (S−P)/(S+P) of white color image, the difference of the frequency and intensity of the horizontal polarized light component is computed, by which the direct light from the headlight of the front-running vehicle, and the reflection light of the headlight (i.e., indirect light) reflected from the wet road can be separately recognized.

Figure 36:
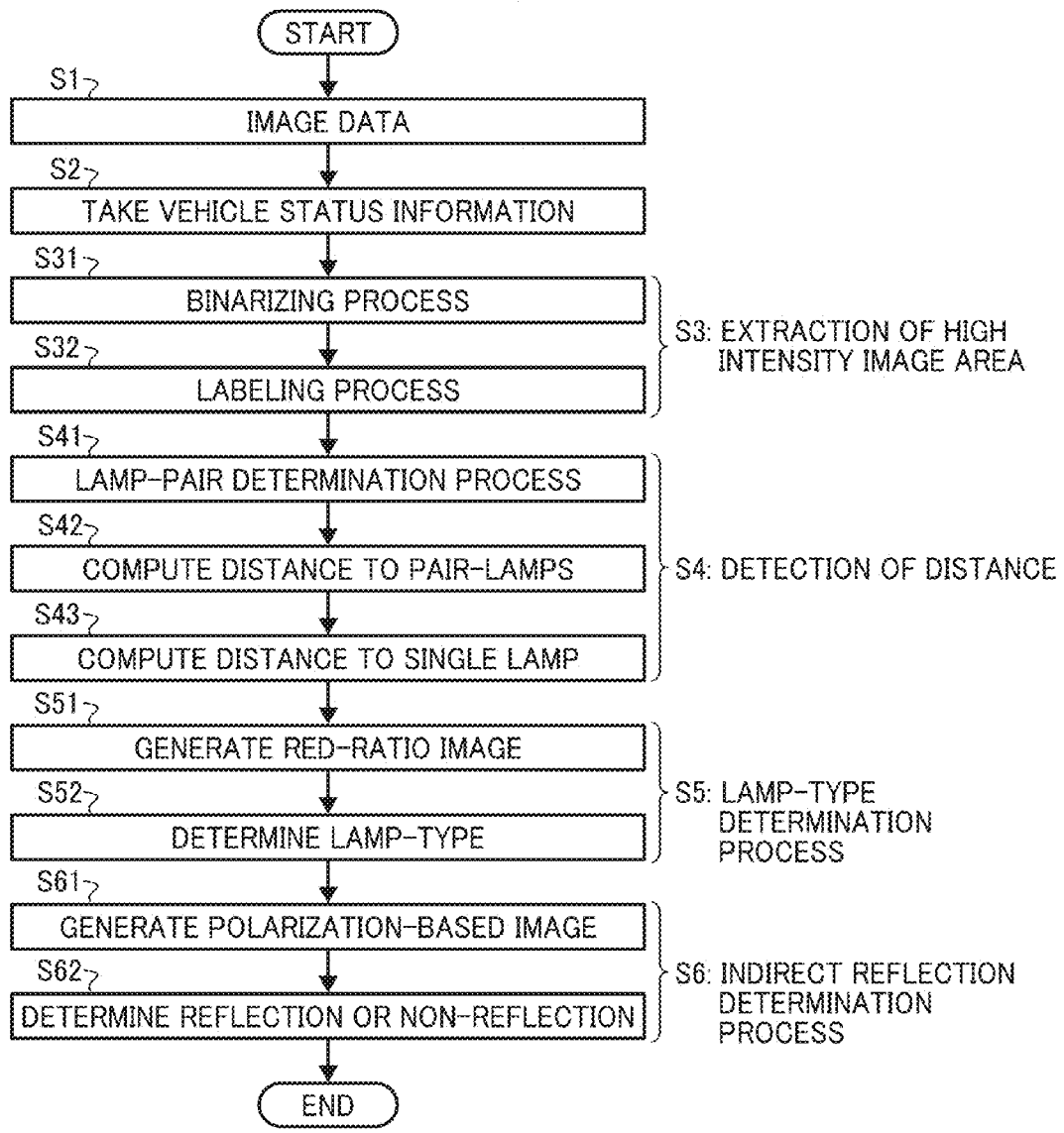
FIG. 36 shows a flowchart of steps of a process of vehicle detection according to an example embodiment.

A description is given of a detection process of the front-running vehicle and the oncoming vehicle according to an example embodiment with reference to FIG. 36, which shows a flowchart of a process of vehicle detection. In the process of detecting vehicles, image data captured by the image capture device 200 receives an image processing, and then an image area, which may be presumed to include a detection-target object, is extracted. Then, by recognizing the types of light emitting object/light reflecting object captured in the extracted image area, the detection of the front-running vehicle and the oncoming vehicle is conducted, in which the light emitting object/light reflecting object is a detection-target object (e.g., tail lamp of front-running vehicle, headlight of oncoming vehicle).

At step S1, image data captured by the image sensor 206 of the image capture device 200 of the vehicle 100 (or detector-equipped vehicle) is taken and stored in a memory, wherein the captured image data may be a forward view image of the vehicle 100. As above described, such image data includes signals indicating the light intensity at each image capture pixel of the image sensor 206. At step S2, the vehicle status information of the vehicle 100 is taken using a vehicle status sensor.

At step S3, based on the image data stored in the memory, high intensity image area, which may be presumed to include a detection-target object (e.g., tail lamp of front-running vehicle, headlight of oncoming vehicle), is extracted. In the image data, such high intensity image area is an area having a light intensity greater than a given threshold value set for the light intensity, and a plurality of areas may present as the high intensity image area, and all of high intensity image areas are extracted. Therefore, at step S3, image areas capturing the light reflected from the wet road (i.e., indirect light) are also extracted as the high intensity image area.

In the extraction process of the high intensity image area, at step S31, the light intensity value at each image capture pixel on the image sensor 206 is compared with a given threshold value set for the light intensity, and then receives a binarizing process. Specifically, an image capture pixel having a light intensity greater than the given threshold value is assigned with "1", and an image capture pixel having a light intensity smaller than the given threshold value is assigned with "0" to generate a binarized image.

At step S32, when pixels assigned with "1" in the binarized image cluster in close proximity positions, such pixels are recognized as one high intensity image area, which may be referred to as a labeling process. By conducting the labeling process, a group composed of a plurality of pixels having high light intensity and existing in the close proximity positions can be extracted as one high intensity image area.

After the extraction process of the high intensity image area, at step S4, the distance detection or computing process is conducted, in which a distance between the vehicle 100 (detector-equipped vehicle) and objects in the image capturing area, corresponding to the each of the extracted high intensity image areas, is computed. In such distance computing process, a pair-lamps distance computing process and a single lamp distance computing process may be conducted.

In the pair-lamps distance computing process, distance is detected using a configuration that a light or lamp of vehicle includes a pair of lamps (i.e., one at left and another at right). In the single lamp distance computing process, the concerned pair-lamps may be recognized as a single lamp when the left and right lamps of the pair-lamps cannot be separately recognized because the concerned vehicle is present at a far distance.

Before the pair-lamps distance computing process, at step S41, a lamp-pair determination process is conducted to determine whether the pair-lamps are present. In the image data captured by the image capture device 200, images of a pair of lamps disposed at right and left may be positioned at close proximity with each other and at the substantially same height position while the area of the high intensity image areas have almost the same size, and the shape of high intensity image areas are almost the same. If the high intensity image areas satisfy such conditions, such high intensity image areas can be determined as the pair-lamps. If the high intensity image area is not presumed as a pair of images, such high intensity image area may be determined as a single lamp.

When it is determined as the pair-lamps, at step S42, the distance to the pair-lamps is computed (pair-lamps distance computing process). The distance to the pair-lamps can be computed using followings: distance between the left and right lights of the headlight and distance between the left and right lamps of the tail lamp can be set to a constant value w0 (e.g., 1.5 m); the focus distance f of the capture lens 204 of the image capture device 200 is known; distance w1 between two lamp image areas on the captured image data, corresponding the left and right lamps/lights, captured by the image sensor 206 of the image capture device 200 can be computed; then, distance X between the pair-lamps of other vehicle and the vehicle 100 (detector-equipped vehicle) can be computed as "X=f×w0/w1," which is a simple proportional calculation. Further, the distance to the front-running vehicle and the oncoming vehicle can be detected using a laser radar/milli-wave radar and specific distance detector or sensor.

At step S5, a lamp-type determination process is conducted based on spectrum information, in which the spectrum information may mean a red color intensity ratio between the perpendicular polarized light component P of red color image and the perpendicular polarized light component P of white color image. Based on such spectrum information, it is determined whether the two high intensity image areas, determined as the pair-lamps, correspond to the light from the headlight, or the light from the tail lamp.

In such lamp-type determination process, at step S51, for the high intensity image areas determined as the pair-lamps, a ratio between pixel data corresponding to the image capture pixels "a, f" of the image sensor 206 (FIG. 14) and pixel data corresponding to the image capture pixels "b" of the image sensor 206 (FIG. 14) is computed to prepare a pixel value of the red-ratio-based image.

At step S52, the pixel value of the red-ratio-based image is compared with a given threshold value. When the pixel value of the high intensity image area is a given threshold value or more of the red-ratio-based image, such high intensity image area is determined as the tail lamp image area, corresponding to the light from the tail lamp, and when the pixel value of the high intensity image area is less than the given threshold value of the red-ratio-based image, such high intensity image area is determined as the headlight image area, corresponding to the light coming from the headlight.

At step S6, an indirect reflection determination process is conducted for each image area, which is determined as the tail lamp image area or the headlight image area, using the polarization index $(S-P)/(S+P)$ as the polarized light information, in which it is determined whether the received light is a direct light such as from light coming from the tail lamp or from headlight, or a reflection light such as light reflected from a mirror surface on a wet road surface (i.e., indirect light).

In the indirect reflection determination process, at step S61, the polarization index $(S-P)/(S+P)$ for the tail lamp image area is computed, and the computed polarization index $(S-P)/(S+P)$ is used as a pixel value to prepare the polarization-light-based image or polarization-based image. Further, the polarization index $(S-P)/(S+P)$ for the headlight image area is computed, and the computed polarization index $(S-P)/(S+P)$ is used as a pixel value to prepare the polarization-light-based image.

At step S62, a pixel value of such polarization-light-based image is compared with a given threshold value. If the pixel value of the tail lamp image area or the headlight image area is a given threshold value or more, such tail lamp image area or the headlight image area can be determined as an area corresponding to light reflected from an object (i.e., indirect light). Then, such image area is determined as an area not capturing the tail lamp of the front-running vehicle or the headlight of the oncoming vehicle, and then removed from the tail lamp image area and the headlight image area. After conducting such removing process, the remaining tail lamp image area and the headlight image area can be determined as an area of the tail lamp of the front-running vehicle or the headlight of the oncoming vehicle.

Further, a rain sensor can be disposed on the vehicle, in which only when the rain sensor detects rainy weather, the indirect reflection determination process (S6) may be conducted. Further, only when a driver activates a wiper, the indirect reflection determination process (S6) may be conducted. As such, only when the rainy weather that reflection from objects (i.e., indirect light) is expected, the indirect reflection determination process (S6) may be conducted.

The detection result of the front-running vehicle and the oncoming vehicle obtained by the vehicle detection process can be used for the light control of headlight of the vehicle 100 (detector-equipped vehicle) having the vehicle-installed devices. Specifically, when the tail lamp is detected by the vehicle detection process, and the distance to the front-running vehicle becomes a given distance that the headlight of the vehicle 100 may project to a rear-view mirror of the front-running vehicle, a part of the headlight of the vehicle 100 is blocked, or the light-emitting direction of the headlight of the vehicle 100 is deviated to the upward/downward direction or the left/right direction to prevent such projection of the headlight of the vehicle 100 to the front-running vehicle.

Further, when the headlight of the oncoming vehicle is detected by the vehicle detection process, and the distance to the oncoming vehicle becomes a distance that the headlight of the vehicle 100 may hits a driver of the oncoming vehicle, a part of the headlight of the vehicle 100 is blocked, or the light-emitting direction of the headlight of the vehicle 100 is deviated to the upward/downward direction or the left/right direction to prevent such hitting of the headlight of the vehicle 100 to the oncoming vehicle.

(Determination Process of Wet/Dry Conditions of Road Surface)

A description is given of determination process of dry/wet information according to the example embodiment. The determination process of determining wet/dry conditions of road surface is conducted determine whether the road surface is at the wet condition, and to determine whether the vehicle 100 (or detector-equipped vehicle) is in a slippery condition. In the wet/dry condition determination process for the road surface, among information obtainable from the image capturing unit 101, polarized light information obtained by comparing the horizontal polarized light component S of white light (i.e., non-separated light) and the perpendicular polarized light component P of white light (i.e., non-separated light) can be used.

Figure 37:
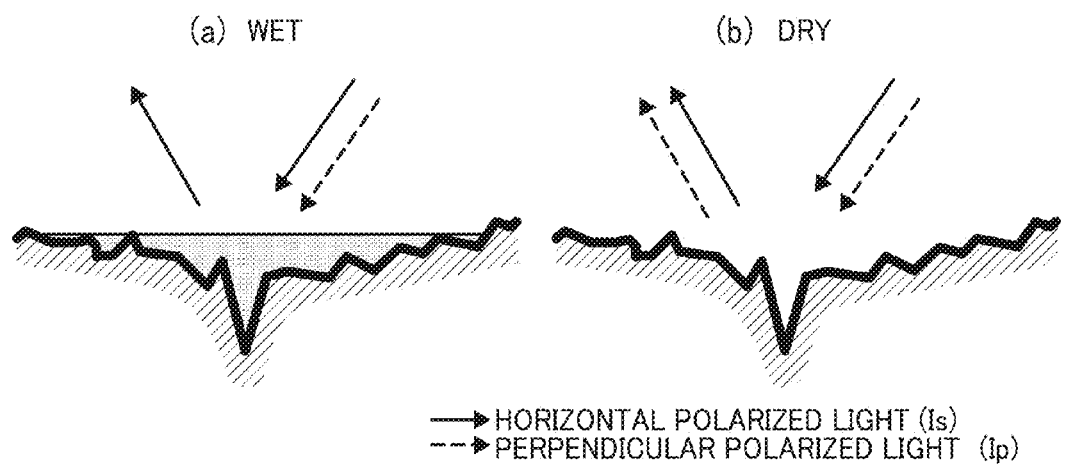
FIG. 37(a) shows a pattern of reflection light from a road surface under the wet condition.
FIG. 37(b) shows a pattern of reflection light from a road surface under the dry condition.

FIGS. 37(a) and 37(b) show example patterns of light reflected from a road surface under the wet and dry conditions. As shown in FIG. 37(a), when the road surface is at the wet condition, water fills concave/convex portions of the road surface, by which a mirror surface can be formed. Under such wet condition, the light reflected from the mirror surface of road surface has a following polarization property.

Figure 38:
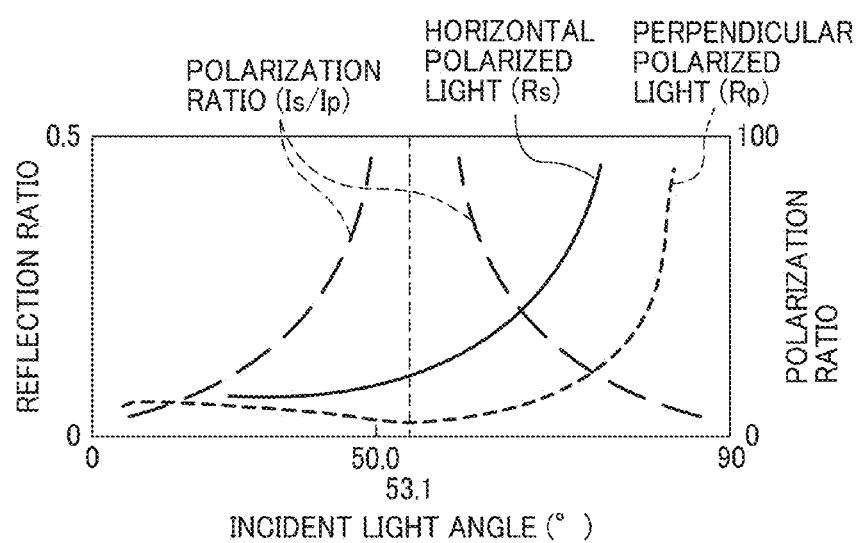
FIG. 38 shows profiles of horizontal polarized light component Is of reflection light, and perpendicular polarized light component Ip of reflection light with respect to incidence light having the light intensity (I), in which the horizontal polarized light component Is and the perpendicular polarized light component Ip change with respect to the incidence angle.

When the reflection ratio of the horizontal polarized light component of reflection light is indicated as Rs, and the reflection ratio of the perpendicular polarized light component of reflection light is indicated as Rp, the horizontal polarized light component Is of reflection light and the perpendicular polarized light component Ip of reflection light with respect to the incidence light having the light intensity (I) can be computed as (1) and (2), and the horizontal polarized light component Is and the perpendicular polarized light component Ip changes with respect to the incidence angle as shown in FIG. 38.

$$Is = Rs \times I \quad (1)$$

$$Ip = Rp \times I \quad (2)$$

As shown in FIG. 38, when the light reflects on the mirror surface, the reflection ratio Rp of the perpendicular polarized light component Ip of the reflection light becomes substantially zero when the incidence angle is the Brewster's angle (53.1°), and the reflection light intensity of the perpendicular polarized light component Ip becomes substantially zero. Further, as shown in FIG. 38, when the light reflects on the mirror surface, the reflection ratio Rs of the horizontal polarized light component Is increases as the incidence angle increases, and the reflection light intensity of the horizontal polarized light component Is also increases as the incidence angle increases.

In contrast, as shown in FIG. 37(b), when the road surface is at the dry condition, the diffused reflection becomes dominant because the road surface is a rough face, and thereby the reflection light may not have distinctive polarization property, and the difference between the reflection ratio Rs for horizontal polarized light component Is and the reflection ratio Rp for perpendicular polarized light component Ip becomes small.

Based on such difference of polarization property of the light reflected from the road surface, it can determine whether the road surface is at the wet or dry conditions. Specifically, in the example embodiment, the determination of the wet/dry conditions of the road surface uses polarization ratio H defined by (3). For example, the polarization ratio H can be defined as a ratio of "S/P," in which a ratio of perpendicular polarized light component P of white light (i.e., non-separated light) and the horizontal polarized light component S of white light (i.e., non-separated light) is computed for an image area capturing the road surface, and an average value of "S/P" may be used. The polarization ratio H computed by (3) is a parameter that does not depend on the incident light intensity (I). Therefore, without receiving the fluctuation effect of light intensity in the image capturing area, the determination of the wet/dry conditions of the road surface can be conducted with a stable manner.

$$H = Is/Ip = Rs/Rp \quad (3)$$

If the polarization ratio H exceeds a given threshold value, the road surface is determined at the wet condition, and if the polarization ratio H is the given threshold value or less, the road surface is determined at the dry condition. If the road surface is at the dry condition, the horizontal polarized light component S and the perpendicular polarized light component P may be substantially same, by which the polarization ratio H may become about one (value G). If the road surface is completely at the wet condition, the horizontal polarized light component S becomes too great compared to the perpendicular polarized light component P, and thereby the polarization ratio H becomes a great value (value H). Further, if the road surface is at the wet condition for some level, the polarization ratio H becomes an intermediate value, which is between (value G) and (value H).

The result of determination process of the wet/dry conditions of the road surface can be used for activating a warning system to a driver of the vehicle 100, and a cruise control system to control a steering wheel and braking of the vehicle 100. Specifically, if the road surface is determined at the wet condition, for example, the determination result is transmitted to the vehicle controller 108 of the vehicle 100 and used to control an automatic braking system, by which possibility of traffic accidents can be reduced. Further, for example, a display screen (e.g., cathode ray tube screen) of a navigation system of the vehicle 100 can display a warning so that the warning of slippery road surface can be informed to a driver.

(Detection Process of Metal-Object on the Road Surface)

A description is given of detection process of metal-object on the road surface according to the example embodiment. The detection of a detection-target object such as a metal-object on the road surface is conducted to prevent skidding of the vehicle 100, and to reduce or prevent miss-recognition by a radar system. The metal-object on the road surface may be metal-based object, which may present on a substantially same face of the road surface. For example, the metal-object may be manhole covers on the road, metal-based connection parts used for highways, or the like. The manhole cover is a metal plate, fitted in an opening of a manhole, and may be made of cast iron, which is tough and heavy.

In the detection process of metal-object on the road surface, a recognition target area is set, wherein the recognition target area may correspond to an image area capturing the road surface having the detection-target object such as the metal-object whereas an image area not capturing the road surface having the metal-object is not used for the detection process of metal-object. Therefore, the recognition target area can be set by removing an upper area of the captured image data. Such recognition target area may not be required to set, but the processing time can be shortened by setting the recognition target area.

Figure 39:
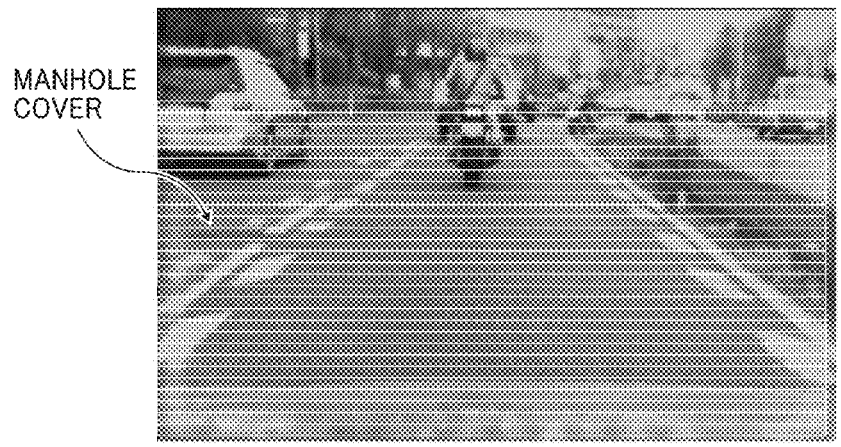
FIG. 39 shows an example of setting process lines for capturing images when detecting a metal-object on a road surface.

Then, a plurality of process lines are set for the recognition target area. The process lines can be set along pixels arrayed in a horizontal direction of the recognition target area as shown in FIG. 39. The process lines can be set any directions such as vertical direction, slanted direction, and horizontal direction. Further, the numbers of pixel in each one of process lines may be set same or different. Further, the process lines may not be set for all pixels in the recognition target area, but can be set partially by selecting effective pixels in the recognition target area.

In the detection process of metal-object on the road surface, among the information obtainable from the image capturing unit 101, the polarized light information obtained by comparing the horizontal polarized light component S of white light (i.e., non-separated light) and the perpendicular polarized light component P of white light (i.e., non-separated light) can be used. Further, the perpendicular polarized light component of white light (i.e., non-separated light) may include the perpendicular polarized light component of red color light.

The polarized light information used for detecting metal-object is the polarization index $(S-P)/(S+P)$, obtained by using the horizontal polarized light component S of white light (i.e., non-separated light) and the perpendicular polarized light component P of white light (i.e., non-separated light). Specifically, when image data is captured by the image capturing unit 101, the polarization index $(S-P)/(S+P)$ is computed based on the horizontal polarized light component S of white light (i.e., non-separated light) and the perpendicular polarized light component P of white light (i.e., non-separated light). Then, the polarization index $(S-P)/(S+P)$ is computed and generated as a pixel value of a polarization-light-based image.

Then, along the above mentioned process lines, a difference of pixel values (i.e., polarization index $(S-P)/(S+P)$) of adjacent two pixels is computed. If the difference becomes greater than a threshold value set for an edge of the metal-object, present on the road surface, an edge is determined between the concerned adjacent two pixels, and the determined edge can be extracted as an edge of the metal-object on the road surface.

By conducting the edge extraction process for all of the process lines, an image area surrounded by the extracted edges can be extracted as a candidate image area of the metal-object. Then, the extracted candidate image area for the metal-object receives a shape recognition processing. Specifically, the shape of extracted candidate image area of the metal-object is compared with a shape template of the metal-object stored in a memory or the like. If the shape of candidate image area of the metal-object matches the shape template of the metal-object, the candidate image area can be recognized as the image area of the metal-object.

The shape recognition processing can be conducted using an approximation curve, which is used for recognizing the shape of edges of candidate image area of the metal-object, in which the shape can be recognized using known methods such as least-squares method, Hough transform, and Model equation, but not limited these.

Further, when the approximation curve is obtained for a candidate image area, a greater weight value is set for edges present at a lower part of the captured image data, which includes data having high precision, compared to edges assumed to be present in an upper part of the captured image data having low precision. If such data weighting is conducted, even if data assumed to be as edges is present in the upper part of the captured image data, the edges recognized at the lower part of the captured image data having high precision can be used to correctly recognize the metal-object on the road surface.

Further, the detection precision of the metal-object on the road surface can be enhanced as follows. When detecting the metal-object on the road surface in real time, the image capture device 200 captures images such as polarization-light-based images continuously with a given time interval. Based on the polarization-light-based images, image area data (or processed result) recognized as the metal-object on the road surface can be stored to a memory.

The image area data (or processed result) stored in the memory can be used to enhance the detection precision of the metal-object. Specifically, the memory stores many image area data, processed in the past. The image area data processed in the past can be compared with the current image area data used for the metal-object, which is recognized currently by the current processing. If the currently recognized metal-object is also recognized as the metal-object in the past image area data, it can be determined that the current processing result has a high precision. For example, based on a position of image area taken for the current image data, and a moving direction/speed of the vehicle 100, the corresponding past image data can be searched and identified. As such, history data can be used to determine the metal-object on the road surface.

In the above explanation, the edge extraction process for the metal-object is conducted along the process lines. Instead of the process lines, process blocks can be used for the edge extraction process for the metal-object, in which each process block may include at least two pixels in a vertical row and at least two pixels in a horizontal row.

In this case, for example, a plurality of process blocks is set for the recognition target area, and a standard deviation of pixel value such as polarization index (S−P)/(S+P) is computed for each one of the process blocks, wherein the standard deviation indicates degree of dispersion. If the computed standard deviation becomes a given threshold value of or more, it can determine that the edge is present in the concerned process blocks. Further, the process block may have a rectangle area, but not limited these. The size of process block may be, for example 10×10 image pixels or so. Further, each of the process blocks may have the same size or different sizes. Further, instead of the standard deviation, a statistical value such as dispersion and mean deviation can be used.

Further, the threshold value used for detecting the metal-object can be switched in view of environmental conditions. For example, the threshold value can be switched depending on time such as day time and night time, or weather such as rainy weather and sunny weather. Such switching can be conducted using time information and/or information of a rain sensor and a sunlight sensor.

A description is given of a reason that metal-object can be recognized separately from the road surface using the polarization index (S−P)/(S+P). When a light enters the interface between two materials having different refractive index with an angle (i.e., incidence angle), the polarization light component in parallel to the incidence plane (e.g., perpendicular polarized light component P), and the polarization light component perpendicular to the incidence plane (e.g., horizontal polarized light component S) have different reflection ratio. Specifically, the reflection ratio of the perpendicular polarized light component P decreases as the incidence angle increases, and becomes substantially zero at a specific angle (i.e., Brewster's angle), and then increases as the incidence angle increases from the Brewster's angle. In contrast, the reflection ratio of the horizontal polarized light component S monotonously increases as the incidence angle increases. As such, because the reflection property of the perpendicular polarized light component P and the reflection property of the horizontal polarized light component S are different, the polarization index (S−P)/(S+P) varies depending on the incidence angle and the refractive index.

Different materials have different refractive indexes, by which the polarization index (S−P)/(S+P) for each material becomes different. The metal-object on the road surface can be recognized separately from the road surface by detecting difference of the polarization index (S−P)/(S+P).

For example, the road surface is typically formed of asphalt face, whereas the metal-object on the road surface is formed of metal. If the materials are different, the refractive index becomes different, and then difference is observed between the polarization index (S−P)/(S+P) of the road surface, and the polarization index (S−P)/(S+P) of the metal-object. Based on such difference, the boundary (or edge) of the road surface and the metal-object on the road surface can be extracted, and the image area having the metal-object can be recognized. Further, by conducting the shape recognition processing with the shape template, the types of the metal-object such as manhole cover, metal-based connection parts, and so on can be identified.

Figure 40:
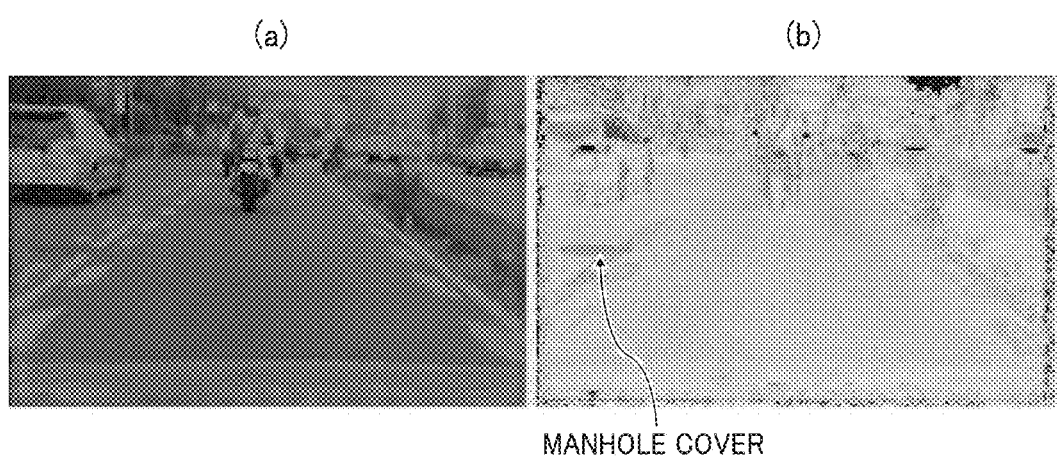

FIGS. 40(*a*) and 40(*b*) are example photos captured for the same image capturing area, in which FIG. 40(*a*) shows a monochrome luminance image of non-separated light/non-polarized light, and FIG. 40(*b*) shows a polarization-light-based image of non-separated light. Because the image capturing area is dark, in the monochrome luminance image of FIG. 40(*a*), the contrast between the asphalt face (i.e., road surface) and the manhole cover (i.e., metal object) is small. In contrast, in the polarization-light-based image of FIG. 40(*b*), the contrast between the asphalt face and the manhole cover is great. Therefore, even if the manhole cover is difficult to recognize in the monochrome luminance image, the manhole cover can be recognized with a high precision by using the polarization-light-based image.

The result of detection process of the metal-object can be used for activating a warning system to a driver of the vehicle 100, and a cruise control system to control a steering wheel and braking of the vehicle 100. Specifically, if a metal-object is recognized on the road surface, for example, the detection result is transmitted to the vehicle controller 108 of the vehicle 100 and used to control an automatic braking system, by which possibility of traffic accidents can be reduced. Further, for example, a display screen (e.g., cathode ray tube screen) of a navigation system of the vehicle 100 can display a warning so that the lane departure warning information can be informed to a driver.

Further, the detection result the metal-object can be used with the distance measurement result by a radar system, and the image captured by the image capture device 200, which may be called as a sensor fusion system.

When the metal-object is detected by the radar system, the distance measurement result by the radar may construe the metal-object as a collision avoidance object such as the front-running vehicle, the guard rail, or the like, which is actually a miss-recognition. The image captured by the image capture device 200 can be used to detect the metal-object, and such detection result of the metal-object can be used to correct the distance measurement result by the radar system, by which the distance measurement result by the radar system is not used for evading the vehicle 100 from the collision avoidance object, and thereby the miss-recognition of collision avoidance object can be prevented. If the metal-object such the manhole cover is miss-recognized as the collision avoidance objects when the vehicle 100 is running, the automatic braking system is activated, and the speed of the vehicle 100 drops radically, which becomes a serious situation. Such situation can be avoided using the above described sensor fusion system.

Further, the detection result of metal-object on the road surface can be used as position information for a car navigation, by which the precision of position identification of the vehicle 100 can be enhanced.

The position information of the manholes such as manhole covers on the road surface can be stored as database. Based on the detection result of a manhole cover, a distance to the manhole cover from the vehicle 100, and a point of the compass such as north, south, east, and west of the vehicle 100 from the manhole cover can be identified. Then, relative position information of the vehicle 100 with respect to the manhole cover is generated, and the manhole identification (ID) set for the manhole cover can be identified. Then, the manhole position information matched to the identified manhole ID is read from the database. Based on the manhole position information, and relative position information of the vehicle 100 with respect to the identified manhole, the position of the vehicle 100 identified by the car navigation can be corrected.

Further, when the detection process of the metal-object on the road surface is conducted, the recognition result of the lane (e.g., white line), to be described later, can be used together, in which the detection process of the metal-object on the road surface can be conducted using the polarization-light-based image that has removed the lane from image data. In this case, noise data such as the lane can be effectively removed, and thereby the recognition precision of metal-object on the road surface can be enhanced.

(Detection Process of Three-Dimensional Object)

A description is given of detection process of three-dimensional object (hereinafter, 3D object) according to the example embodiment. To avoid the collision with the 3D object, the 3D object is detected as the detection-target object. The 3D object may mean any 3D objects such as vehicles running on a driving lane surface, guard rails at road-side ends of a driving lane, telegraph poles, streetlamps/streetlights, traffic signs, obstacles existing along road-side end such as stepped portions, persons, animals, and bicycles on a driving lane or shoulder of road. Each of 3D objects may have an outer face extending in a direction different from a surface direction of driving lane.

In the detection process of 3D object, among the information obtainable from the image capturing unit 101, the polarized light information obtained by comparing the horizontal polarized light component S of white light (i.e., non-separated light) and the perpendicular polarized light component P of white light (i.e., non-separated light) can be used. Further, the perpendicular polarized light component P of white light (i.e., non-separated light) may include the perpendicular polarized light component P of red color light. As similar to the detection process of the metal-object on the road surface, the polarized light information used for detecting 3D object is the polarization index (S−P)/(S+P), obtained by using the horizontal polarized light component S of white light (i.e., non-separated light) and the perpendicular polarized light component P of white light (i.e., non-separated light).

Specifically, when image data is captured by the image capturing unit 101, the polarization index (S−P)/(S+P) is computed based on the horizontal polarized light component S of white light (i.e., non-separated light) and the perpendicular polarized light component P of white light (i.e., non-separated light).

Figure 41:
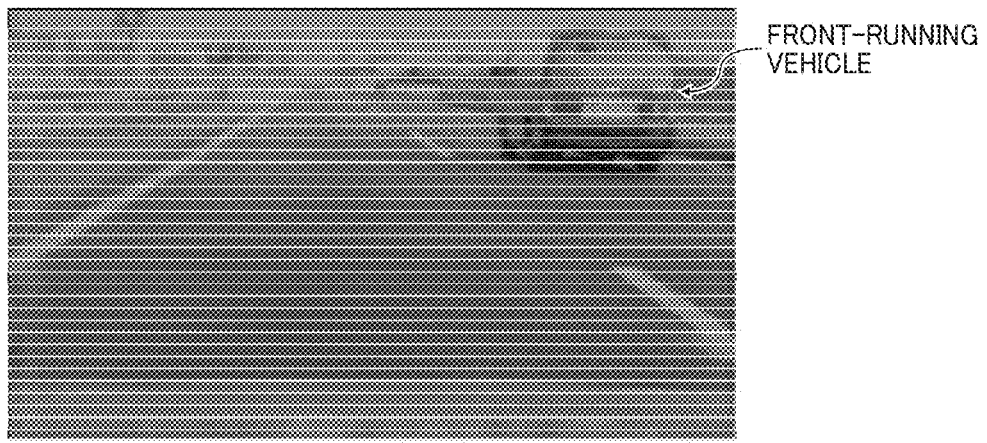
FIG. 41 shows an example of setting process lines for capturing images when detecting a three-dimensional object.

Then, the pixel value such as polarization index (S−P)/(S+P) is computed to generate a polarization-light-based image. As similar to the detection process of the metal-object on the road surface, process lines are set. Because the 3D object (i.e., detection-target object) exists in an entire image capturing area, as shown in FIG. 41, the process lines are set for the entire captured image without setting the recognition target area. Further, the process lines or process blocks can be set as similar to the detection process of the metal-object on the road surface.

After setting the process lines, along the above mentioned process lines, a difference of pixel values such as polarization index (S−P)/(S+P)) of adjacent two pixels is computed. If the difference becomes greater than a threshold value set for an edge of 3D object, such edge is determined as an edge between the concerned adjacent two pixels. The pixel value such as polarization index (S−P)/(S+P) of concerned adjacent two pixels is compared with a threshold value set for the 3D object. If pixel values such as the polarization index (S−P)/(S+P)) is the threshold value or more set for the 3D object, the edge can be determined and extracted as an edge of the 3D object.

By conducting the edge extraction process for the entire process lines, an image area surrounded by edges of the 3D object can be extracted as a candidate image area of the 3D object. Then, the extracted candidate image area for the 3D object receives a shape recognition processing. Specifically, the shape of extracted candidate image area of the 3D object is compared with a shape template of the 3D object stored in a memory or the like. If the shape of candidate image area of the 3D object matches the shape template of the 3D object, the candidate image area can be recognized as the image area of the 3D object. The shape recognition processing can be conducted as similar to the detection process of the metal-object.

Further, the threshold value used for detecting the 3D object can be switched in view of environmental condition. For example, the threshold value can be switched depending on time such as day time and night time, or weather such as rainy weather and sunny weather. Such switching can be conducted using time information and/or information of a rain sensor and a sunlight sensor.

A description is given of a reason that 3D object can be recognized using the polarization index (S−P)/(S+P). When a light enters the interface between two materials having different refractive index with an angle (i.e., incidence angle), because the perpendicular polarized light component P, and the horizontal polarized light component S have different reflection property such as different reflection ratio, the polarization index (S−P)/(S+P) varies depending on the incidence angle and the refractive index. The different refractive index of polarized light components induces the different polarization index (S−P)/(S+P) for different materials, by which the 3D object can be recognized separately from the road surface by detecting the polarization index (S−P)/(S+P).

For example, the road surface is typically formed of asphalt face, whereas the 3D object such as other vehicles and guard rails in the image capturing area may have a coated layer coated on a metal face of the 3D object. If the materials are different, the refractive index of the materials becomes different, and then difference is observed between the polarization index (S−P)/(S+P) of the road surface and the polarization index (S−P)/(S+P) of 3D object. Based on such difference, the boundary (or edge) of the road surface and the 3D object such as other vehicles and guard rails having the coated face can be extracted, and the image area having the 3D object can be recognized.

Further, the road surface is a substantially flat face, whereas the 3D object such as other vehicle has a side face extending in a direction different from a direction of the road surface. Therefore, the incidence angle of light entering the image capture device 200 after reflecting from the road surface, and the incidence angle of light entering the image capture device 200 after reflecting from the side faces of 3D object become different.

Therefore, the perpendicular polarized light component P and the horizontal polarized light component S of the reflection light reflected from the road surface become different from the perpendicular polarized light component P and the horizontal polarized light component S of the reflection light reflected from the side faces of the 3D object.

For example, if the side faces of the 3D object are substantially elevated faces with respect to the direction of the road surface, the relative relation of the perpendicular polarized light component P and the horizontal polarized light component S of the reflection light reflected from the side faces of the 3D object becomes the substantially opposite to the relative relation of the perpendicular polarized light component P and the horizontal polarized light component S of the reflection light reflected from the road surface.

Typically, as for the relative relation of the perpendicular polarized light component P and the horizontal polarized light component S included in the reflection light, the horizontal polarized light component S, which is a polarization light component perpendicular with respect to the incidence plane becomes greater than the perpendicular polarized light component P, which is a polarization light component parallel with respect to the incidence plane.

Therefore, when the image capture device 200 receives the light reflected from the road surface or a face parallel to the road surface, the horizontal polarized light component S becomes greater than the perpendicular polarized light component P. In contrast, when the image capture device 200 receives the light reflected from the side faces of the 3D object, substantially elevated with respect to the direction of the road surface, the perpendicular polarized light component P becomes greater than the horizontal polarized light component S.

Such difference between the polarization property of the light reflected from the road surface and the polarization property of the light reflected from the 3D object can be used for detecting the 3D object. Specifically, when the image capture device 200 receives the reflection light, the perpendicular polarized light component P of the reflection light is compared with the horizontal polarized light component S of the reflection light. If the horizontal polarized light component S is greater than the perpendicular polarized light component P, the reflection light is determined as the light reflected from a face parallel to the road surface. In contrast, if the perpendicular polarized light component P of the reflection light is greater than the horizontal polarized light component S of the reflection light, the reflection light is determined as the light reflected from a face perpendicular to the direction of the road surface.

Therefore, when the image capture device 200 receives the reflection light, the difference of between the perpendicular polarized light component P and the horizontal polarized light component S of the reflection light, is computed. Depending on whether the difference of images such as polarization index (S−P)/(S+P) becomes positive or negative value, it can determine whether an object reflecting the reflection light is an object having a face parallel to the road surface, or a 3D object having a face extending in a direction different from the direction of the road surface.

Based on such difference caused by different materials and incidence angle, the boundary (or edge) of the road surface and 3D object can be extracted, and the image area of 3D object can be recognized. Further, by conducting the shape recognition processing with the shape template, the types of 3D objects such as automobiles, guard rails, and so on can be identified.

Figure 42:
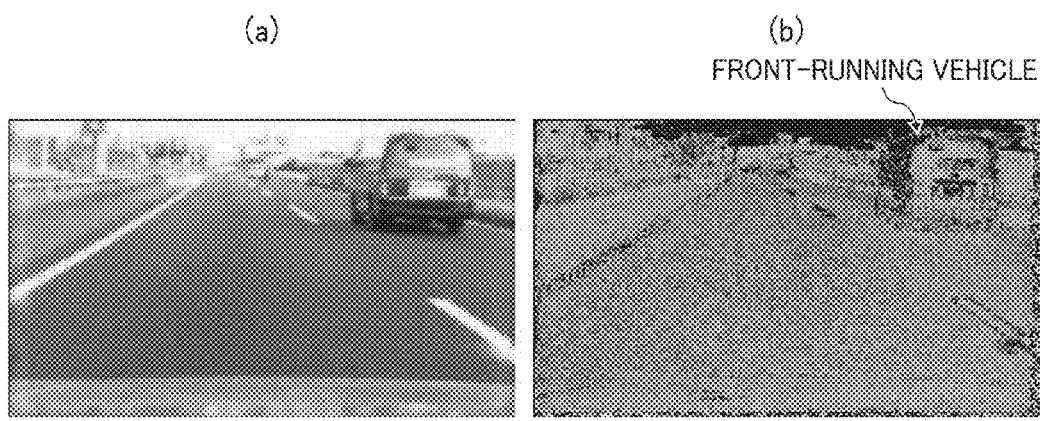

FIGS. 42(*a*) and 42(*b*) are example photos captured for the same image capturing area, in which FIG. 42(*a*) shows a monochrome luminance image of non-separated light/non-polarized light, and FIG. 42(*b*) shows a polarization-light-based image of non-separated light. Because the image capturing area is dark, in the monochrome luminance image of FIG. 42(*a*), the contrast between the road surface and the front-running vehicle (i.e., 3D object) is small. In contrast, in the polarization-light-based image of FIG. 42(*b*), the contrast between the road surface and the front-running vehicle (i.e., 3D object) is great. Therefore, even if the front-running vehicle is difficult to recognize in the monochrome luminance image, the front-running vehicle can be recognized with a high precision by using the polarization-light-based image.

As such, if materials are different, the polarization index (S−P)/(S+P) are different. The reflection property of polarization light of a material such as the asphalt face used for the road surface, and the reflection property of polarization light of the coating agent used for a side faces of the 3D object such as automobile are analyzed to confirm the difference of the reflection property of polarization light. With such a configuration, the road surface such as the asphalt face and the 3D object such as an automobile can be recognized separately.

The light reflected from the object may include specular reflection component, diffuse reflection component, which is reflection component coming from a matte surface having tiny convex/concave portions on a surface of an object, and internal scattering component, which is scattered inside the object and then going out from the object. The intensity of reflection light can be defined by adding such three components. Further, the specular reflection component may be recognized as a part of the diffuse reflection component.

The diffuse reflection component and the internal scattering component can be observed without any relevancy of a position of a light source that emits light to the object (i.e., diffuse reflection component and internal scattering component have low dependency to the incidence angle). In contrast, the specular reflection component can be observed only when the light source is set at a position corresponding to the regular reflection direction of light to enter a light receiving element (i.e., specular reflection component has high dependency to the incidence angle). Such relation can be similarly set for the polarization property of light.

As above described, without any relevancy of a position of the light source, the diffuse reflection component and the internal scattering component can be observed, but the polarization property of the diffuse reflection component and the internal scattering component are different. Specifically, as for the diffuse reflection component, the surface of the object is segmented into tiny areas, and each area may satisfy Fresnel equations for describing reflection. Therefore, if non-polarized light enters the object, the horizontal polarized light component S becomes greater than the perpendicular polarized light component P.

In contrast, the internal scattering component is a component scattered in the object and then coming out from the object. When the non-polarized light enters the object, the effect of polarization light component of the light that enters the object becomes little, and thereby when the light comes out of the object, the perpendicular polarized light component P becomes strong.

When a front view of the vehicle 100 is captured from the vehicle 100, most of objects such as an asphalt face, a manhole cover, or the like in the image capturing area have convex/concave portions on their surfaces, and thereby the specular reflection component is small for the light reflected from such objects. Therefore, in the example embodiment, the light reflected from objects, present in the image capturing area of the image capture device 200, may be mostly the diffuse reflection component and the internal scattering component.

By comparing the intensity of the horizontal polarized light component S and the intensity of the perpendicular polarized light component P in the reflection light, it can determine which one of the diffuse reflection component and the internal scattering component is dominant in the reflection light. If the intensity of the horizontal polarized light component S is greater than the intensity of the perpendicular polarized light component P, it can determine that the diffuse reflection component is dominant in the reflection light. In contrast, if the intensity of the perpendicular polarized light component P is greater than the intensity of the horizontal polarized light component S, it can determine that the internal scattering component is dominant in the reflection light.

Figure 43:
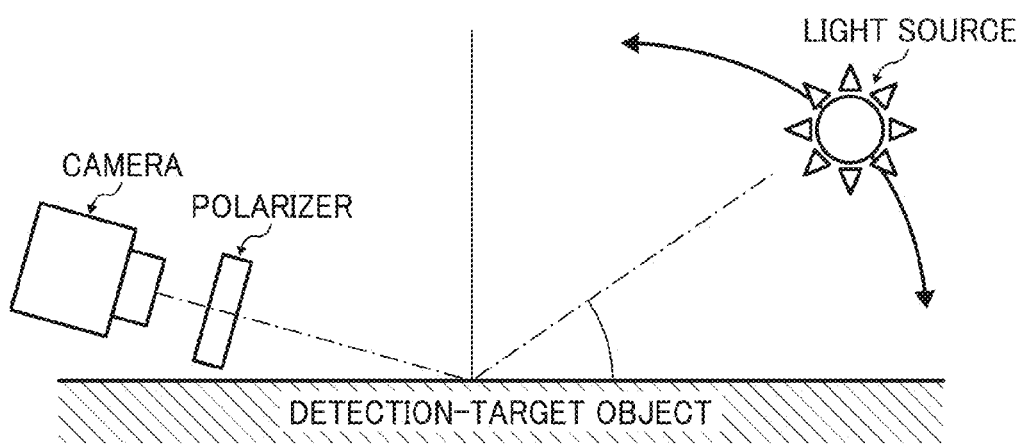
FIG. 43 shows a schematic configuration of an optical system to capture images of the horizontal polarized light component S and the perpendicular polarized light component P reflected from a detection-target object in a laboratory, in which positions of a light source with respect to the detection-target object can be changed, and a camera fixed at a given position captures images of the horizontal polarized light component S and the perpendicular polarized light component P.

FIG. 43 shows a schematic configuration of an optical system to capture images of the horizontal polarized light component S and the perpendicular polarized light component P reflected from a detection-target object in a laboratory. The light source was a halogen lamp, the camera was a high vision camera, and a polarizer was disposed in front of the camera, by which polarization light direction was selectable. Specifically, the positions of a light source with respect to a detection-target object can be changed, and a camera fixed at a given position captures images of the horizontal polarized light component S and the perpendicular polarized light component P. In this experiment, by changing positions of the light source, the camera captured images of the horizontal polarized light component S and the perpendicular polarized light component P of an asphalt face, and the change of polarization index (S−P)/(S+P) was measured. Further, by changing the positions of the light source, the camera captured images of the horizontal polarized light component S and the perpendicular polarized light component P of a coated face, prepared by coating a coating agent on a steel, and the change of polarization index (S−P)/(S+P) was measured.

Figure 44:
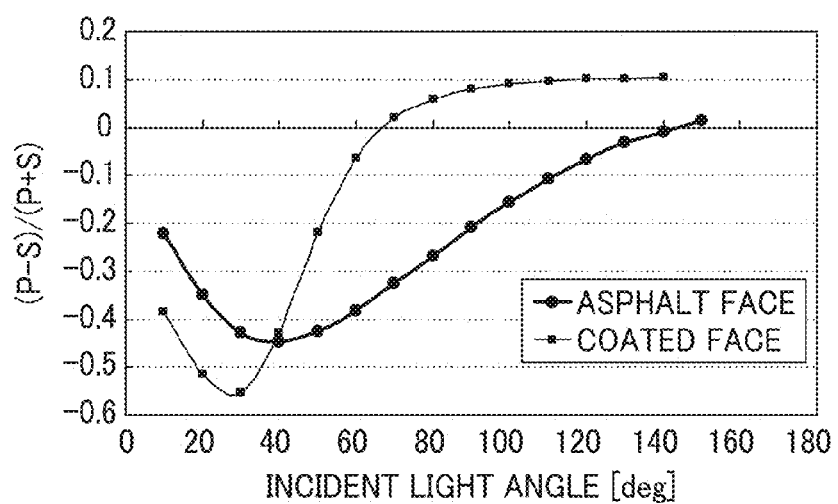
FIG. 44 shows a graph of experiment result obtained by using the optical system of FIG. 43, in which an asphalt face and a coated face were used as the detection-target object.

FIG. 44 shows a graph of the experiment result of FIG. 43. In FIG. 44, the horizontal axis represents the incidence angle (i.e., light source position), and the vertical axis represents the polarization index (P−S)/(P+S). The angle of elevation of the camera from the horizontal plane was 10 degrees. The polarization index (P−S)/(P+S) was computed using light intensity information, obtained from the substantially center portion of captured images corresponding to each of incidence angles used in this experiment. The polarization index (P−S)/(P+S) used in this experiment is a ratio of a value obtained by subtracting the horizontal polarized light component S from the perpendicular polarized light component P, and a value obtained by adding the perpendicular polarized light component P and the horizontal polarized light component S. Therefore, the positive/negative of the polarization index (P−S)/(P+S) used in this experiment becomes the opposite of the positive/negative of the above described polarization index (S−P)/(S+P). Therefore, in this experiment, if the perpendicular polarized light component P is greater than the horizontal polarized light component S, a positive value was obtained, and if the horizontal polarized light component S is greater than the perpendicular polarized light component P, a negative value was obtained.

As shown in FIG. 44, the polarization index (P−S)/(P+S) of the asphalt face was negative values for the almost entire range of the incidence angle, which means that the horizontal polarized light component S is greater than the perpendicular polarized light component P. This occurs because the diffuse reflection component is dominant in the reflection light reflected from the asphalt face. In contrast, the polarization index (P−S)/(P+S) of the coated face became a positive value when the incidence angle is greater than 60 degrees or so. This occurs because the internal scattering component and the diffuse reflection component are both present in the reflection light reflected from the coated face. Based on such difference of polarization property indicated by the polarization index (P−S)/(P+S), the asphalt face and the coated face can be recognized separately.

The detection result of the 3D object can be used for activating a warning system to a driver of the vehicle 100, and a cruise control system to control a steering wheel and braking of the vehicle 100. Specifically, if the 3D object is recognized, for example, the detection result is transmitted to the vehicle controller 108 of the vehicle 100 and used to control an automatic braking system, by which possibility of traffic accidents can be reduced. Further, for example, a display screen (e.g., cathode ray tube screen) of a navigation system of the vehicle 100 can display a warning so that the lane departure warning information can be informed to a driver.

(Detection Process of Road-Side End)

A description is given of detection process of the road-side end according to the example embodiment. The detection of the road-side end (i.e., detection-target object) is conducted to prevent departure or deviation of the vehicle 100 from a driving lane. The road-side end may mean stepped portions between a driving lane and pedestrian, roadside groove, roadside vegetation, guard rail, and side wall such as concrete wall.

In the detection process of the road-side end, among the information obtainable from the image capturing unit 101, the polarized light information obtained by comparing the horizontal polarized light component S of white light (i.e., non-separated light) and the perpendicular polarized light component P of white light (i.e., non-separated light) can be used. Further, the perpendicular polarized light component P of white light (i.e., non-separated light) may include the perpendicular polarized light component P of red color light.

As similar to the detection process of the 3D object, the polarized light information used for detecting the road-side end is the polarization index (S−P)/(S+P), obtained by using the horizontal polarized light component S of white light (i.e., non-separated light) and the perpendicular polarized light component P of white light (i.e., non-separated light).

Specifically, when image data is captured by the image capturing unit 101, the polarization index (S−P)/(S+P) is computed based on the horizontal polarized light component S of white light (i.e., non-separated light) and the perpendicular polarized light component P of white light (i.e., non-separated light). Then, the polarization index (S−P)/(S+P) is used as a pixel value to generate a polarization-light-based image. As similar to the detection process of the 3D object, the process lines are set. Further, the process lines or process blocks can be set as similar to the detection process of the 3D object.

After setting the process lines, along the above mentioned process lines, a difference of pixel values such as polarization index (S−P)/(S+P) of adjacent two pixels is computed. If the difference becomes greater than a threshold value set for an edge of the road-side end, an edge is determined between the concerned adjacent two pixels. The pixel value such as polarization index (S−P)/(S+P) of two pixels related to the identified edge is compared with a threshold value set for identifying the road-side end. If the pixel value is the threshold value or more, the edge can be determined and extracted as an edge of the road-side end.

By conducting the edge extraction process for the entire process lines, an image area surrounded by edges of the road-side end can be extracted as a candidate image area of the road-side end. Then, the extracted candidate image area for the road-side end receives a shape recognition processing. Specifically, the shape of extracted candidate image area of the road-side end is compared with a shape template of the road-side end stored in a memory or the like. If the shape of candidate image area of the road-side end matches the shape template of the road-side end, the candidate image area can be recognized as the image area of the road-side end. The shape recognition processing can be conducted as similar to the detection process of the 3D object.

Further, the threshold value used for detecting the road-side end can be switched in view of environmental condition. For example, the threshold value can be switched depending on time such as day time and night time, or weather such as rainy weather and sunny weather. Such switching can be conducted using time information and/or information of a rain sensor and a sunlight sensor.

The road-side end can be recognized by using the polarization index (S−P)/(S+P) with a same reason of the recognition of 3D object. Because the polarization index (S−P)/(S+P) becomes different due to the difference of materials and/or the incidence angle, a boundary (or edge) between the road surface and the road-side end can be extracted based on the polarization index (S−P)/(S+P). Further, by conducting the shape recognition processing with the shape template, the types of the road-side end can be identified.

Figure 45:
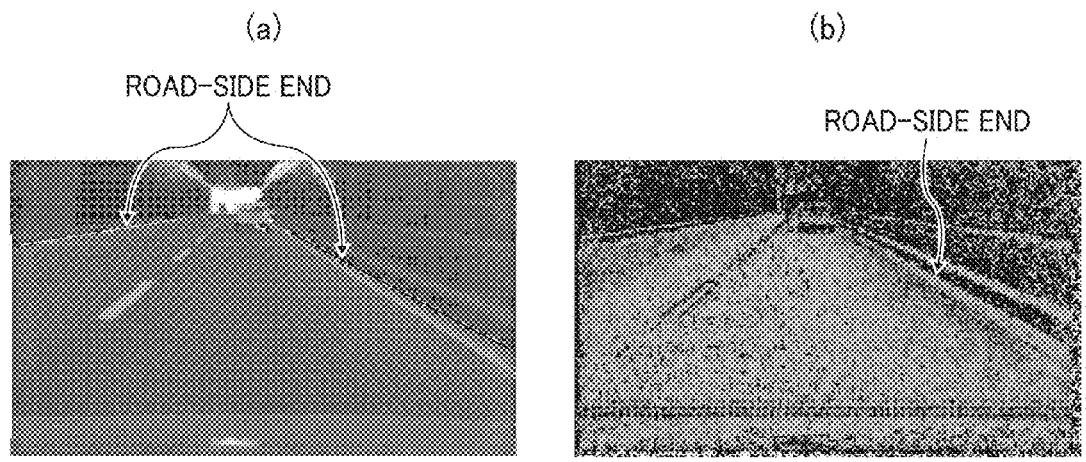

FIGS. 45(a) and 45(b) are example photos captured for the same image capturing area, in which FIG. 45(a) shows a monochrome luminance image of non-separated light/non-polarized light, and FIG. 45(b) shows a polarization-light-based image of non-separated light. The image capturing area is dark because the image was captured when the vehicle 100 was running in a tunnel. Therefore, in the monochrome luminance image of FIG. 45(a), the contrast between the road surface and the tunnel wall (i.e., road-side end) is small. In contrast, in the polarization-light-based image of FIG. 45(b), the contrast between the road surface and the tunnel wall is great. Therefore, even if the tunnel wall is difficult to recognize in the monochrome luminance image, the tunnel wall can be recognized with a high precision by using the polarization-light-based image.

As such, if materials are different, the polarization index (S−P)/(S+P) are different. The reflection property of polarization light of a material such as an asphalt face used for the road surface, and the reflection property of polarization light of a concrete wall (i.e., road-side end) are analyzed to confirm the difference of the reflection property of polarization light. With such a configuration, the road surface such as asphalt face and the road-side end such as the concrete wall can be recognized separately.

Figure 46:
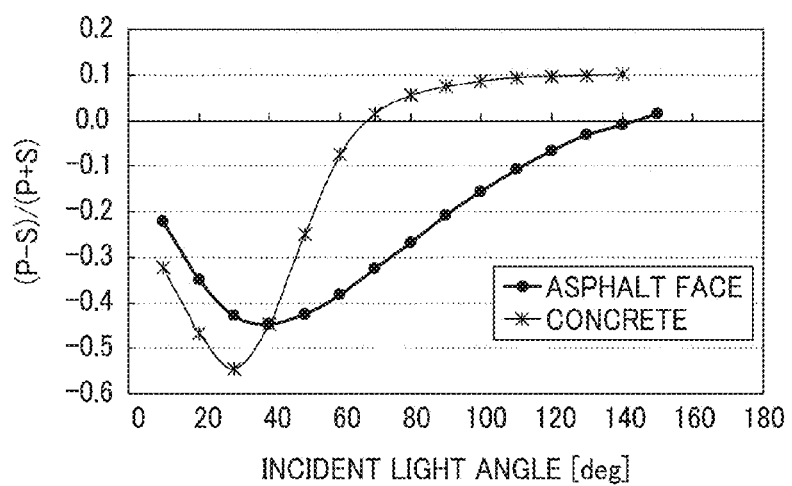
FIG. 46 shows a graph of experiment result obtained by using the optical system of FIG. 43, in which an asphalt face and a concrete face were used as a detection-target object.

FIG. 46 shows a graph of the experiment result conducted in a laboratory, in which the positions of a light source with respect to a detection-target object is changed, and the camera fixed at a given position captured images of the horizontal polarized light component S and the perpendicular polarized light component P of the asphalt face and the concrete face (i.e., detection-target object). The optical system of FIG. 43 was used with the same experiment conditions for the asphalt face and the coated face.

As shown in FIG. 46, the polarization index (P−S)/(P+S) of the asphalt face was almost negative values for the entire incidence angle, which means that the horizontal polarized light component S is greater than the perpendicular polarized light component P. In contrast, the polarization index (P−S)/(P+S) of the concrete face became a positive value when the incidence angle is greater than 60 degrees or so as similar to the coated face (FIG. 44). This occurs because the internal scattering component and the diffuse reflection component are both present in the reflection light from the concrete face. Based on such difference of polarization property indicated by the polarization index (P−S)/(P+S), the asphalt face and the concrete face can be recognized separately.

The detection result of the road-side end can be used for activating a warning system to a driver of the vehicle 100, and a cruise control system to control a steering wheel and braking of the vehicle 100. Specifically, if the road-side end is recognized, for example, the detection result is transmitted to the vehicle controller 108 of the vehicle 100 and used to control an automatic braking system, by which possibility of traffic accidents can be reduced. Further, for example, a display screen (e.g., cathode ray tube screen) of a navigation system of the vehicle 100 can display a warning so that the lane departure warning information can be informed to a driver.

(Detection Process of Lane)

A description is given of detection process of the lane (e.g., white line) according to the example embodiment. The detection of the lane (i.e., detection-target object) is conducted to prevent departure or deviation of the vehicle 100 from a driving lane. The lane means any type of lanes (e.g., white line) for defining road area such as solid line, dashed line, dotted line, double lines, or the like. Further, the lanes other than white line such as yellow line can be detected similarly.

In the detection process of the lane, among the information obtainable from the image capturing unit 101, the polarized light information obtained as the perpendicular polarized light component P of white light (i.e., non-separated light) can be used. Further, the perpendicular polarized light component P of white light (i.e., non-separated light) may include the perpendicular polarized light component P of cyan light.

Typically, the light reflected from the lane, and the light reflected from the asphalt face may show a light intensity profile, which may be substantially flat spectrum in the visible light range. Because the cyan light includes light having a wide range of wavelength in the visible light range, the cyan light can be preferably used for capturing images of the asphalt face and the lane (e.g., white line).

Therefore, by using the optical filter 205 of the second example configuration, the perpendicular polarized light component P of cyan light is included in the perpendicular polarized light component P of white light (i.e., non-separated light), by which the numbers of image capture pixels useable for the detection process can be increased, and thereby the resolution level can be enhanced resultantly, and the lane at a far distance point can be detected.

Typically, the lane such as a white line is formed on the road surface having a color close to black. Therefore, when the detection process of the lane is conducted, the intensity of light reflected from the lane becomes greater than the intensity of light reflected from other portion of the road surface in an image of the perpendicular polarized light component P of white light (i.e., non-separated light). Therefore, if the light intensity of one portion is greater than a given value or more, such portion can be determined and detected as the lane.

Because the horizontal polarized light component S is cut from the image of perpendicular polarized light component P of white light (i.e., non-separated light) used for the detection process, the light reflection from an object (i.e., indirect light) from the wet road can be suppressed, and an image suppressing the effect of indirect light can be captured. Therefore, the ambient light such as the reflection light of headlight reflected from the wet road (i.e., indirect light) in the night time may not be recognized as the lane, and thereby the lane can be detected effectively without miss-recognition.

Further, in the detection process of the lane, among information obtainable from the image capturing unit 101, polarized light information obtained by comparing the horizontal polarized light component S of white light (i.e., non-separated light) and the perpendicular polarized light component P of white light (i.e., non-separated light) can be also used. Specifically, the polarization index (S−P)/(S+P) can be computed using the horizontal polarized light component S and the perpendicular polarized light component P of white light (i.e., non-separated light).

Typically, the light reflected from the lane includes the diffuse reflection component as dominant component, in which the perpendicular polarized light component P and the horizontal polarized light component S of the reflection light becomes almost the same, and thereby the polarization index (S−P)/(S+P) becomes nearly zero.

In contrast, the light reflected from the asphalt face having not formed with the lane (e.g., white line) includes the diffuse reflection component as dominant component under the dry condition, and the polarization index (S−P)/(S+P) for the light reflected from the asphalt face becomes a positive value, in which positive/negative value is opposite to positive/negative value of the experiment results shown in FIGS. 44 and 46.

Further, the light reflected from the asphalt face having not formed with the lane (e.g., white line) includes the specular reflection component as dominant component under the wet condition, by which the polarization index (S−P)/(S+P) becomes further greater. Therefore, if the polarization index (S−P)/(S+P) of one portion of the road surface is smaller than a threshold value, such portion can be determined as the lane (e.g., white line).

Figure 47:
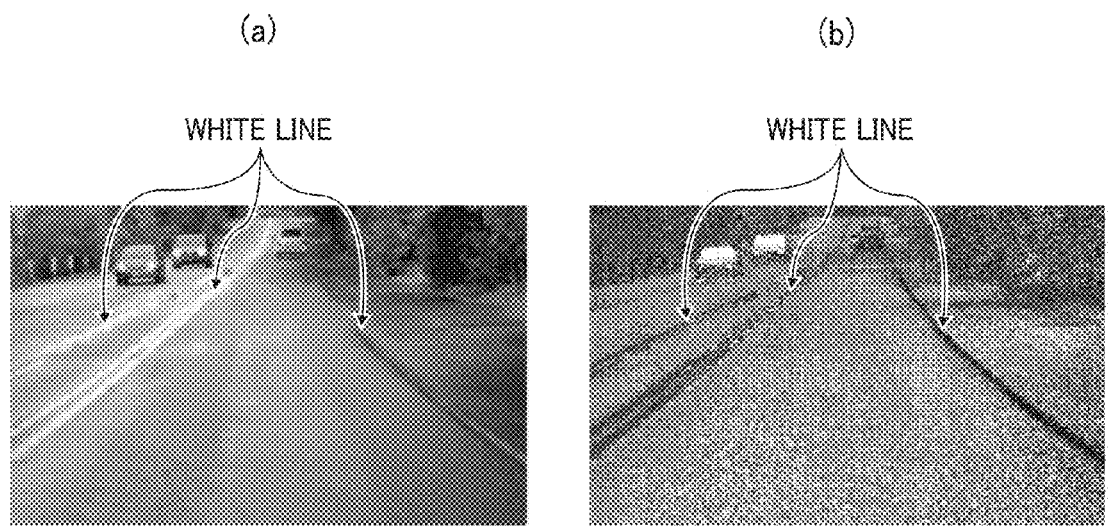

FIGS. 47(a) and 47(b) are example photos captured for the same image capturing area under the rainy weather, in which FIG. 47(a) shows a monochrome luminance image of non-separated light/non-polarized light, and FIG. 47(b) shows a polarization-light-based image of non-separated light. The image capturing area is relatively dark because the image was captured when the vehicle 100 was running in the rainy weather, and further, the road surface was at the wet condition. Therefore, in the monochrome luminance image of FIG. 47(a), the contrast between the road surface and the lane (e.g., white line) is small. In contrast, in the polarization-light-based image of FIG. 47(b), the contrast between the road surface and the lane is effectively great. Therefore, even if the lane is difficult to recognize in the monochrome luminance image, the lane can be recognized with a high precision by using the polarization-light-based image.

Further, because the white line present at the right side the captured image is in a shadow area, in the monochrome luminance image of FIG. 47(a), the contrast between the white line at the right side and the road surface becomes small. In contrast, in the polarization-light-based image of FIG. 47(b), the contrast between the white line at the right side and the road surface is effectively great. Therefore, even if the lane is difficult to recognize in the monochrome luminance image, the lane can be recognized with a high precision by using the polarization-light-based image.

(Detection Process of Raindrop on Windshield)

A description is given of detection process of the raindrop according to the example embodiment. The detection of the raindrop on windshield (i.e., detection-target object) is conducted for the drive control of the wiper 107 and the dispensing control of washer fluid. In the following example, raindrop is described as substance on the windshield, but the adhered substance is not limited to the raindrop. For example, excrements of birds, water splash from the road surface splashed by other vehicles become the adhered substance.

In the detection process of raindrops on the windshield 105, among the information obtainable from the image capturing unit 101, polarized light information of the light, which passes the infra-red transmittance-filter area 212 of the front-end filter 210, and the polarized light filter 225 of the rear-end filter 220 used as the raindrop detection filter 220B, is used. Specifically, among the light that is received by the raindrop detection image area 214, the perpendicular polarized light component P is used.

Figure 48:
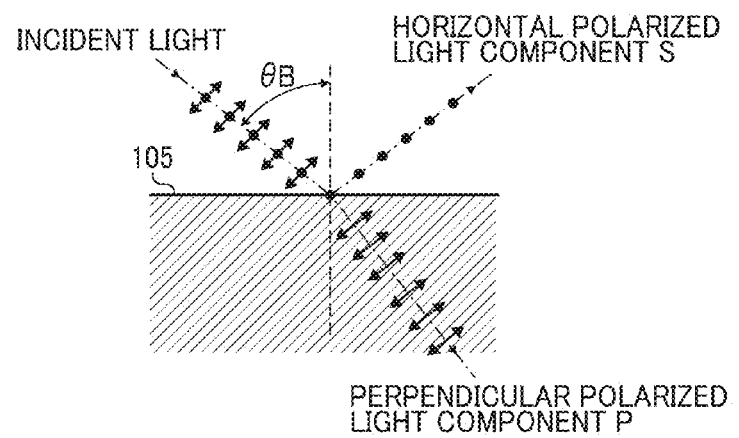
FIG. 48 shows polarization conditions of reflection light when an incident light reflects with the Brewster's angle.

FIG. 48 shows polarization conditions of light reflected with the Brewster's angle. When a light enters and reflects on a flat face such as a flat glass face, the reflection ratio of the horizontal polarized light component S monotonously increases with respect to the incidence angle, while the reflection ratio of the perpendicular polarized light component P becomes substantially zero at a specific angle (i.e., Brewster's angle θB in FIG. 48), and the perpendicular polarized light component P is not reflected at the flat face but passes through the flat face as shown in FIG. 48.

Therefore, if the light source 202 emits light having only the perpendicular polarized light component P from the inside of the vehicle 100 to the windshield 105 with the incidence angle of the Brewster's angle θB (FIG. 48), such light does not reflect at the inner face of the windshield 105 (i.e., a face facing an inside of vehicle), but the perpendicular polarized light component P passes through the windshield 105, and reaches the outer face of the windshield 105. If the light reflects at the inner face of the windshield 105, such reflection light becomes ambient light of the image capture device 200, by which deterioration of the raindrop detection performance may occur.

The emission of light having only the perpendicular polarized light component P to the windshield 105 can be devised as follows. For example, the light emitted from the light source 202 can be used to prepare the light having only the perpendicular polarized light component P as follows. If the light source 202 uses a light emitting diode (LED), a polarizer that passes through only the perpendicular polarized light component P is disposed between the light source 202 and the windshield 105. Further, if the light source 202 uses a semiconductor laser diode (LD), because the LD can emit only a specific polarization light component, the optical axis of the LD is set to a given direction so that the light having only the perpendicular polarized light component P enters the windshield 105.

FIG. 49(a) is an example captured image when raindrops adhere on the outer face of the windshield 105, and FIG. 49(b) is an example captured image when raindrops do not adhere on the outer face of the windshield 105. In the captured images of FIGS. 49(a) and 49(b), the lower area having "detection area" corresponds to the raindrop detection image area 214, and the rest of upper area corresponds to the vehicle detection image area 213.

As shown in FIG. 49(a), when raindrops adhere on the outer face of the windshield 105, the raindrop detection image area 214 includes information of light emitted from the light source 202, and as shown in FIG. 49(b), when raindrops do not adhere on the outer face of the windshield 105, the raindrop detection image area 214 does not include information of light emitted from the light source 202.

Therefore, the recognition process of raindrop image at the raindrop detection image area 214 can be easily conducted by adjusting the threshold value set for the intensity or amount of light, emitted from the light source 202 and received by the image sensor 206. Further, the threshold value is not limited to a specific value, but can be changed depending on the surrounding conditions of the vehicle 100 having the image capture device 200. For example, the threshold value can be changed by computing a suitable value based on the exposure adjustment information of the image capture device 200.

In the example embodiment, based on the raindrop detection result, the wiper controller 106 can control the drive control of the wiper 107 and the dispensing control of washer fluid.

The above image capture device 200 may employ a single eye camera, but the image capturing device 200 can employ a stereo camera having two camera units. Each of the two camera units of the stereo camera may employ a similar configuration of the image capture device 200 of single eye camera.

In the above described detection apparatus, the light source 202 emits the light to the windshield 105, which is a transparent member such as a transparent plane, from the inner face of the windshield 105. If the substance such as raindrop adheres on the outer face of the windshield 105, which is the opposite to the inner face, the light emitted from the light source 202 reflects at the substance such as raindrop on the outer face, and then the reflection light is received by the image sensor 206 via the capture lens 204, wherein the image sensor 206 may employ a pixel array composed of the light receiving elements 206A such as the photodiodes 206A arrayed two dimensionally.

The image capture device 200 captures the image of substance on the outer face of the windshield 105. Based on the image of adhered substance captured by the image capture device 200, the substance detection processor conducts a substance detection process to detect the adhered substance.

The image capture device 200 captures images of the adhered substance via a polarization filter such as the polarized light filter 225. The polarized light filter 225 passes only polarization light component (e.g., perpendicular polarized light component P) having a polarization light direction substantially parallel to a virtual plane (or incidence plane of light source) including an optical axis of light, emitted from the light source 202 toward the windshield 105, and an optical axis of the capture lens 204. With such a configuration, the adhered-substance image can be obtained by cutting most of ambient light (i.e., S-polarized light component) such as the regular light reflected regularly on the inner face of the windshield 105, by which the detection precision of adhered substance can be enhanced.

In the above described detection apparatus, the focus of the image capture lens 204 may be set at a point in the distance beyond a planar transparent member such as the windshield 105, which may be far distance point from the windshield 105. With such a configuration, as above described, objects such as the substance on the windshield 105 become out-of-focus condition or defocused condition, by which image area of adhered substance becomes great, and thereby the recognition precision of adhered substance can be enhanced. Further, if the focus of the capture lens 204 is set at the adhered substance, the indirect light projected on the adhered substance may be also captured, and such indirect light image may be erroneously detected as adhered substance. Because an object such as substance on the windshield 105 becomes out-of-focus condition (or defocused condition), the indirect light projected on the adhered substance may not be captured, by which erroneous detection of adhered substance can be avoided.

In the above described detection apparatus, the light source 202 can be configured with a plurality of light sources, and the polarization filter includes a plurality of polarization filter areas arranged in a two dimensional direction and may have different transmission axis directions with each other. Each one of polarization filter areas may be corresponded to a unit area on the image sensor 206 such as a unit area composed by one light receiving element or a unit area composed by two or more light receiving elements. The image sensor 206 includes the pixel array composed by the light receiving elements arranged in two dimensional directions.

In such configuration, one polarization filter area receives the light from the plurality of light sources, and one of the plurality of light sources emits the greatest incidence light amount to the concerned polarization filter area among the plurality of light sources. Each one of the polarization filter areas is set with a transmission axis to pass only polarization light component having a polarization light direction parallel to a virtual plane including an optical axis of the light source inputting the greatest incidence light amount to the concerned polarization filter area, and an optical axis of the capture lens 204.

With such a configuration, compared to using only one light source, light amount of light reflected from the adhered substance and received by the image sensor 206 becomes greater, by which the detection precision of the adhered substance can be enhanced. Further, because light can be emitted to a greater area of the windshield 105, the detection area of adhered substance can be enlarged. As a result, for example, when the raindrop detection is conducted, adherence of raindrops can be detected earlier.

In the above described detection apparatus, the polarization filter can employ a wire grid structure. As above described, the wire grid structure can be manufactured by the semiconductor processing, and the polarization axis can be adjusted by changing the direction of grooves of sub-wavelength convex/concave structure, by which a polarizer pattern (or polarization filter area) having the different polarization axes can be formed for each of image capture pixels at an order of several micron meters. Further, because the wire grid structure is formed of thin metal wires, the optical filter 205 having high heat-resistance/light-resistance can be formed. The light-resistance means resistance to degradation of optical properties caused by ultraviolet or the like. By having high heat-resistance and light-resistance, the wire grid structure can be preferably used for the image capturing device installed for vehicles or other units.

In the above described detection apparatus, the light source 202 may emit the light having a given specific range of wavelength such as infra-red light wavelength. The image capture device 200 includes the polarization filter and the light separation filter such as the infra-red transmittance-filter area 212 that passes only a given specific range of wavelength to capture images of the adhered substance. With such a configuration, the adhered-substance image can be obtained by cutting ambient light coming from the light emitting object/light reflecting object, generating the light having the wavelength different from the light coming from the light source 202, by which the detection precision of adhered substance can be further enhanced.

In the above described detection apparatus, the image sensor 206 includes a first pixel array, and a second pixel array. The first pixel array corresponds to the raindrop detection image area 214 to capture images of substance on the windshield 105. The second pixel array corresponds to the vehicle detection image area 213 to capture an object such as other vehicle, lane (e.g., white line) or the like that may be present at a far distance point from the windshield 105. The object detection processor such as the image analyzer 102 is disposed to conduct a detection process of objects based on the images captured by the second pixel array. Further, based on the image captured by the first pixel array, the substance detection processor such as the image analyzer 102 conducts the detection process of the substance adhered on the windshield 105. With such a configuration, by using one image capturing device, the adhered substance and objects at a far distance point can be detected concurrently.

In the above described detection apparatus, a light source emits the light from one face (e.g., inner face) of the windshield 105 to other face (e.g., outer face) of the windshield 105. The light emitted from the light source enters the windshield 105 from the inner face, and then reflects at substance on the outer face of the windshield 105 such as a transparent plane. Then, via the image capture lens 204, the reflection light is received by the image sensor 206 composed of a pixel array having light receiving elements arrayed two dimensionally to capture images of substance on the outer face of the windshield 105. Based on the image of the captured adhered substance, the detection process of adhered substance can be conducted. The image of the adhered substance is captured via a polarization filter that passes only a polarization light component having a polarization light direction substantially parallel to a virtual plane including an optical axis of the light source that emits light toward the windshield 105, and an optical axis of the image capture lens 204. With such a configuration, the adhered-substance image can be obtained by cutting most of ambient light (i.e., S-polarized light component) such as the regular light reflected regularly on the inner face of the windshield 105, by which the detection precision of adhered substance can be enhanced.

In the above described example embodiment, light such as ambient light that reflects regularly on the inner face of a transparent member such as a transparent plane when a light source emits light to the transparent member can be reduced, and the detection precision of substance on the outer face of a transparent member, opposite to the inner face of the transparent member, can be enhanced. Such configuration can be used for the substance detection apparatus and method.

The present invention can be implemented in any convenient form, for example using dedicated hardware, or a mixture of dedicated hardware and software. The present invention may be implemented as computer software implemented by one or more networked processing apparatuses. The network can comprise any conventional terrestrial or wireless communications network, such as the Internet. The processing apparatuses can compromise any suitably programmed apparatuses such as a general purpose computer, personal digital assistant, mobile telephone (such as a Wireless Application Protocol (WAP) or 3G-compliant phone) and so on. Since the present invention can be implemented as hardware and software, each and every aspect of the present invention thus encompasses computer software implementable on a programmable device.

The computer software can be provided to the programmable device using any storage medium or carrier medium for storing processor readable code such as a flexible disk, a compact disk read only memory (CD-ROM), a digital versatile disk read only memory (DVD-ROM), DVD recording only/rewritable (DVD-R/RW), electrically erasable and programmable read only memory (EEPROM), erasable programmable read only memory (EPROM), a memory card or stick such as USB memory, a memory chip, a mini disk (MD), a magneto optical disc (MO), magnetic tape, a hard disk in a server, a solid state memory device or the like, but not limited these.

The hardware platform includes any desired kind of hardware resources including, for example, a central processing unit (CPU), a random access memory (RAM), and a hard disk drive (HDD). The CPU may be implemented by any desired kind of any desired number of processor. The RAM may be implemented by any desired kind of volatile or non-volatile memory. The HDD may be implemented by any desired kind of non-volatile memory capable of storing a large amount of data. The hardware resources may additionally include an input device, an output device, or a network device, depending on the type of the apparatus. Alternatively, the HDD may be provided outside of the apparatus as long as the HDD is accessible. In this example, the CPU, such as a cache memory of the CPU, and the RAM may function as a physical memory or a primary memory of the apparatus, while the HDD may function as a secondary memory of the apparatus.

In the above-described example embodiment, a computer can be used with a computer-readable program, described by object-oriented programming languages such as C++, Java (registered trademark), JavaScript (registered trademark), Perl, Ruby, or legacy programming languages such as machine language, assembler language to control functional units used for the apparatus or system. For example, a particular computer (e.g., personal computer, work station) may control an information processing apparatus or an image processing apparatus using a computer-readable program, which can execute the above-described processes or steps. In the above described embodiments, at least one or more of the units of apparatus can be implemented in hardware or as a combination of hardware/software combination. In example embodiment, processing units, computing units, or controllers can be configured with using various types of processors, circuits, or the like such as a programmed processor, a circuit, an application specific integrated circuit (ASIC), used singly or in combination.

Numerous additional modifications and variations are possible in light of the above teachings. It is therefore to be understood that, within the scope of the appended claims, the disclosure of the present invention may be practiced otherwise than as specifically described herein. For example, elements and/or features of different examples and illustrative embodiments may be combined each other and/or substituted for each other within the scope of this disclosure and appended claims.

What is claimed is:

1. A substance detection apparatus, comprising:
    a light source to emit light to a planar transparent member, having a proximal first face and a distal second face opposite the first face, the light from the light source first striking the first face of the planar transparent member;
    an image capture lens;
    a polarization filter including a two-dimensional array of polarization filter areas that are adjacent to each other, each dimension of the two-dimensional array having more than two polarization filter areas;
    an image sensor; and
    a substance detection processor that executes a detection process to detect a substance present on the second face of the planar transparent member based on an image of the substance captured by the image sensor,
    wherein the polarization filter, disposed after the image capture lens and before the image sensor with respect to a direction of the light entering the image sensor, passes only a polarized light component having a polarized light direction substantially parallel to a virtual plane including an optical axis of the light source that emits the light to the planar transparent member and an optical axis of the image capture lens,
    wherein the image sensor is composed of a two-dimensional array of pixels having a plurality of light receiving elements,
    wherein the light emitted from the light source is reflected at the substance present on the second face of the planar transparent member, the image sensor receives a light reflected from the substance, via the image capture lens and the polarization filter, to capture an image of the substance present on the second face of the planar transparent member; and
    wherein the focus of the image capture lens is set at a point in a distance beyond the planar transparent member and less than infinity.

2. The substance detection apparatus of claim 1, wherein the light source includes a plurality of light sub-sources,
    wherein the polarization filter areas have different transmission axes,
    each one of the polarization filter areas corresponding to a unit area on the image sensor, the unit area on the image sensor being composed of one light receiving element or two or more light receiving elements,
    wherein each one of the polarization filter areas is set with a transmission axis to pass only a polarized light component having a polarized light direction parallel to a virtual plane including an optical axis of the light source that inputs the greatest incidence light amount to a relevant polarization filter area, and an optical axis of the image capture lens.

3. The substance detection apparatus of claim 1, wherein the polarization filter employs a wire grid structure.

4. The substance detection apparatus of claim 1, further comprising a light separation filter,
wherein the light source emits the light having a specific wavelength band and the light separation filter selects only the light including the specific wavelength band emitted from the light source,
wherein the image sensor captures an image of the substance via the polarization filter and the light separation filter.

5. The substance detection apparatus of claim 1, wherein the image sensor is segmented into a first pixel array and a second pixel array,
wherein the first pixel array of the image sensor captures an image of a substance present on the planar transparent member,
wherein the second pixel array of the image sensor captures an object in the distance beyond the planar transparent member,
the substance detection apparatus further including an object detection processor to conduct a detection process of the object in the distance based on an image captured by the second pixel array of the image sensor,
wherein the substance detection processor conducts the substance detection process based on an image captured by the first pixel array of the image sensor.

6. The substance detection apparatus of claim 1, wherein the image capture lens, the polarization filter, and the image sensor are combined to form an image capture device.

7. A method of detecting a substance, comprising the steps of:
emitting light, using a light source, to a planar transparent member, having a proximal first face and distal second face opposite the first face, the light from the light source first striking the first face of the planar transparent member;
when the light emitted from the light source is reflected at a substance on the second face of the planar transparent member, receiving light reflected from the planar transparent member by an image capture lens;
passing, via a polarization filter, only a polarized light component having a polarized light direction substantially parallel to a virtual plane including an optical axis of the light source that emits the light to the planar transparent member and an optical axis of the image capture lens;
capturing an image of the substance present on the second face of the planar transparent member by using an image sensor composed of a pixel array having a plurality of light receiving elements arrayed two dimensionally, based on the light reflected from the planar transparent member and passed through the polarization filter, the polarization filter including a two-dimensional array of polarization filter areas that are adjacent to each other, each dimension of the two-dimensional array having more than two polarization filter areas; and
detecting the substance based on the image of substance captured by the image sensor;
wherein a focus of the image capture lens is set at a point in a distance beyond the planar transparent member and less than infinity.

8. A non-transitory computer-readable storage medium storing a program that, when executed by a computer, causes the computer to execute a method of detecting a substance, comprising the steps of:
emitting light, using a light source, to a planar transparent member, having a proximal first face and distal second face opposite the first face, the light from the light source first striking the first face of the planar transparent member;
when the light emitted from the light source is reflected at a substance on the second face of the planar transparent member, receiving light reflected from the planar transparent member by an image capture lens;
passing, via a polarization filter, only a polarized light component having a polarized light direction substantially parallel to a virtual plane including an optical axis of the light source that emits the light to the planar transparent member and an optical axis of the image capture lens;
capturing an image of the substance present on the second face of the planar transparent member by using an image sensor composed of a pixel array having a plurality of light receiving elements arrayed two dimensionally, based on the light reflected from the planar transparent member and passed through the polarization filter, the polarization filter including a two-dimensional array of polarization filter areas that are adjacent to each other, each dimension of the two-dimensional array having more than two polarization filter areas; and
detecting the substance based on the image of substance captured by the image sensor;
wherein a focus of the image capture lens is set at a point in a distance beyond the planar transparent member and less than infinity.

9. The substance detection apparatus of claim 1, wherein each polarization filter area is settable with a corresponding image capture pixel.

10. The method of claim 7, wherein each polarization filter area is settable with a corresponding image capture pixel.

11. The non-transitory computer-readable storage medium of claim 8, wherein each polarization filter area is settable with a corresponding image capture pixel.

* * * * *